(12) United States Patent
Laal et al.

(10) Patent No.: US 7,745,141 B2
(45) Date of Patent: Jun. 29, 2010

(54) MYCOBACTERIAL PROTEINS AS EARLY ANTIGENS FOR SERODIAGNOSIS AND VACCINES

(75) Inventors: Suman Laal, Cortlandt Manor, NY (US); Susan Zolla-Pazner, New York, NY (US)

(73) Assignee: New York University, New York, NY (US)

( * ) Notice: Subject to any disclaimer, the term of this patent is extended or adjusted under 35 U.S.C. 154(b) by 1550 days.

(21) Appl. No.: 10/481,563

(22) PCT Filed: Jun. 21, 2001

(86) PCT No.: PCT/US01/20545

§ 371 (c)(1),
(2), (4) Date: Nov. 8, 2004

(87) PCT Pub. No.: WO03/073101

PCT Pub. Date: Sep. 4, 2003

(65) Prior Publication Data

US 2005/0084904 A1    Apr. 21, 2005

(51) Int. Cl.
*G01N 33/53* (2006.01)
*A61K 39/04* (2006.01)
*A61K 39/02* (2006.01)

(52) U.S. Cl. .......................... 435/7.1; 424/9.1; 424/9.2; 424/184.1; 424/185.1; 424/190.1; 424/192.1; 424/234.1; 424/248.1; 424/278.1; 435/7.2; 530/300; 530/350

(58) Field of Classification Search .................. 424/9.1, 424/9.2, 184.1, 185.1, 190.1, 192.1, 234.1, 424/248.1, 278.1; 435/7.1, 7.2; 530/300, 530/350
See application file for complete search history.

*Primary Examiner*—Rodney P. Swartz
(74) *Attorney, Agent, or Firm*—Browdy and Neimark, PLLC

(57) ABSTRACT

A number of protein and glycoprotein antigens secreted by, or expressed on the surface of, *Mycobacterium tuberculosis* (Mtb) have been identified as "early" Mtb antigens on the basis of antibodies present in subjects infected with Mtb prior to the development of detectable clinical disease. PirG protein encoded by the Mtb gene Rv3810, PE-PGRS protein encoded by the Mtb gene Rv3367, PTRP protein encoded by the Mtb gene Rv0538) and MtrA protein encoded by the Mtb gene Rv3246c, or epitopes of these proteins, are useful in immunoassay methods or T cell assays for early, rapid detection of TB in a subject. Preferred immunoassays detect antibodies in the urine. Also provided are antigenic compositions, kits and methods useful for detecting these early Mtb antigens and early Mtb antibodies specific for them. Vaccine compositions comprising the foregoing antigens or epitopes are also disclosed.

17 Claims, 25 Drawing Sheets

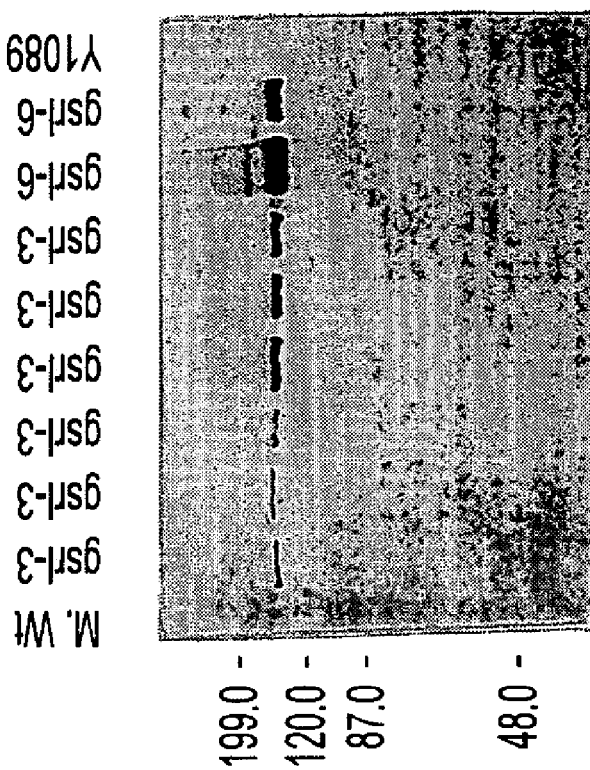
FIG. 2B GUINEA PIG SERUM POOL
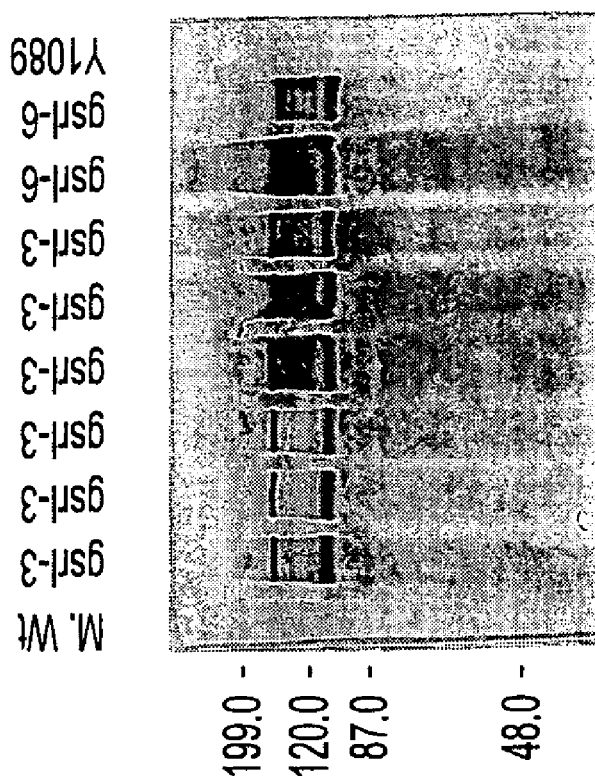
FIG. 2A ANTI-β GALACTOSIDASE ANTIBODY

ANTI-β GALACTOSIDASE ANTIBODY

GUINEA PIG SERUM POOL

ANTI-β GALACTOSIDASE ANTIBODY

GUINEA PIG SERUM

```
   1  MNFPVLPPEI NSVLMYSGAG SSPLLAAAAA WDGLAEELGS AAVSFGQVTS
  51  GLTAGVWQGA AAAAMAAAAA PYAGWLGSVA AQAVAVAGQA RAAVAAFEAA
 101  LAATVDPAAV AVNRMAMRAL AMSNLLGQNA AAIAAVEAEY ELMWAADVAA
 151  MAGYHSGASA AAAALPAFSP PAQALGGGVG AFLNALFAGP AKMLRLNAGL
 201  GNVGNYNVGL GNVGIFNLGA ANVGAQNLGA ANAGSGNFGF GNIGNANFGF
 251  GNSGLGLPPG MGNIGLGNAG SSNYGLANLG VGNIGFANTG SNNIGIGLTG
 301  DNLTGIGGLN SGTGNLGLFN SGTGNIGFFN SGTGNFGVFN SGSYNTGVGN…
..........................................................
2301  …SVTIPALTAA RAVLDMAASV GATSEIEPFI VWTSSGAIGP TWYSVGRIYN
                                                            gsrI-6
2351  AGDLFVGGNI ISGIPTLSTT GPVHAVFNAA SQAFNTPALN IHQIPLGFQ V
2401  PGSIDAITLF PGGLTFPANS LLNLDVFVGT PGATIPAITF PEIPANADGE
2451  LYVIAGDIPL INIPPTPGIG NTTTVPSSGF FNTGAGGGSG FGNFGANMSG
2501  WWNQAHTALA GAGSGIANVG TLHSGVLNLG SGLSGIYNTS TLPLGTPALV
2551  SGLGNVGDHL SGLLASNVGQ NPITIVNIGL ANVGNGNVGL GNIGNLNLGA
2601  ANIGDVNLGF GNIGDVNLGF GNIGGGNVGF GNIGDANFGF GNSGLAAGLA
2651  GMGNIGLGNA GSGNVGWANM GLGNIGFGNT GTNNLGIGLT GDNQSGIGGL
2701  NSGTGNIGLF NSGTGNIGFF NSGTANFGLF NSGSYNTGIG NSGVASTGLV
2751  NAGGFNTGVA NAGSYNTGSF NAGDTNTGGF NPGSTNTGWF NTGNANTGVA
2801  NAGNVNTGAL ITGNFSNGIL WRGNYEGLAG FSFGYPIPLF PAVGADVTGD
2851  IGPATIIPPI HIPSIPLGFA AIGHIGPISI PNIAIPSIHL GIDPTFDVGP
2901  ITVDPITLTI PGLSLDAAVS EIRMTSGSSS GFKVRPSFSF FAVGPDGMPG
2951  GEVSILQPFT VAPINLNPTT LHFPGFTIPT GPIHIGLPLS LTIPGFTIPG
3001  GTLIPQLPLG LGLSGGTPPF DLPTVVIDRI PVELHASTTI GPVSLPIFGF
3051  GGAPGFGNDT TAPSSGFFNT GGGGGSGFSN SGSGMSGVLN AISDPLLGSA
              gsrII-2
3101  SGF ANFGTQLSGILNRGAGI SGVYNTGTLG LVTSAFVSGF MNVGQQLSGL
3151  LFAGTGP
```

FIG. 4B

```
  1 MTEFDDIKNL SLPETRDAAK QLLDSVAGDL TGEAAQRFQA LTRHAEELRA
 51 EQRRRGREAE EALRRYRAGE LRVVPGAPTG GDDGDAPPGN SLRDTAFRTL
101 DSCVRDGLMS SRAAETAETL CRTGPPQSTS WAQRWLAATG SRDYLGAFVK
151 RVSNPVAGHT VWTDREAAAW REAAAVAAEQ RAMGLVDTQG GFLIPAALDP
``` gsrII-1

```
201 ⌐AILLSGDGST NPIRQVARVV QTTSEIWRGV TSEGAEARWY SEAQEVSDDS
251  PALAQPAVPN YRGSCWIPFS IELEGDAASF VGEIGKILAD SVEQLQAAAF
301  VNGSGNGEPT GFVSALTGTS DQVVVGAGSE AIVAADVYAL QSALPPRFQA
351  SAAFAANLST INTLRQAETS NGALKFPSLH DSPPMLAGKS VLEVSHMDTV
401  DSAVTATNHP LVLGDWKQFL IGDRVGSMVE LVPHLFGPNR RPTGQRGFFA
451  WFRVGSDVLV RNAFRVLKVE TTA⌐
```

FIG. 5B

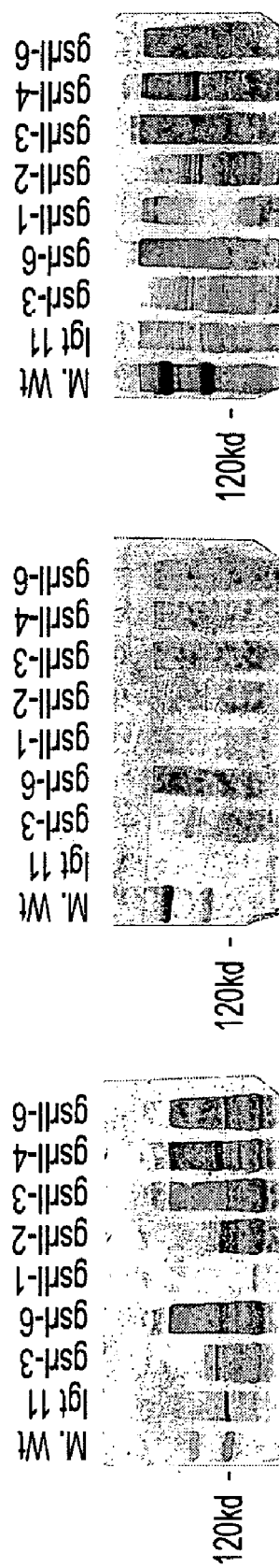

```
   1 atgtcgtttgtcgtagcagtcccggaggcattggcggcggccgcgtcggatgtggcgaac
     M  S  F  V  V  A  V  P  E  A  L  A  A  A  A  S  D  V  A  N   20
  61 atcggttctgcgctaagtgccgcgaatgcagcggcagccgccggcacaacggggctactg
     I  G  S  A  L  S  A  A  N  A  A  A  A  A  G  T  T  G  L  L   40
 121 gcagccggtgccgacgaggtctcggccgccctggcgtcgctgttttccgggcacgctgtg
     A  A  G  A  D  E  V  S  A  A  L  A  S  L  F  S  G  H  A  V   60
 181 agctaccaacaggtcgcggcccaggcgacggcgttacacgatcagtttgtccaggccttg
     S  Y  Q  Q  V  A  A  Q  A  T  A  L  H  D  Q  F  V  Q  A  L   80
 241 accggtgccggcggatcgtacgccctcaccgaggccgccaacgtccagcagaatctgctg
     T  G  A  G  G  S  Y  A  L  T  E  A  A  N  V  Q  Q  N  L  L  100
 301 aacgcaattaacgcgcccactcaggcgctgttggggcgcccgttaattggcgacggggct
     N  A  I  N  A  P  T  Q  A  L  L  G  R  P  L  I  G  D  G  A  120
 361 gtcggcaccgccagcagccccgacgggcaagatggcggtctgctgttcggcaacggggc
     V  G  T  A  S  S  P  D  G  Q  D  G  G  L  L  F  G  N  G  G  140
 421 gccggctacaacagcgccgccacgcccggaatggccggcggcaacggcggcaacgccgga
     A  G  Y  N  S  A  A  T  P  G  M  A  G  G  N  G  G  N  A  G  160
 481 ttgatcggcaacggcggtactggccgggtcggcggtgccggcgcggccggtggcgccggc
     L  I  G  N  G  G  T  G  G  S  G  G  A  G  A  A  G  G  A  G  180
 541 ggcagcggcggctggttgtacggcaacggcggaaacggcggcatcggcgggaatgcgatc
     G  S  G  G  W  L  Y  G  N  G  G  N  G  G  I  G  G  N  A  I  200
 601 gtcgcgggcggtgccggcggcaatgggggcgctggcggcgccgcggattgtggggcagt
     V  A  G  G  A  G  G  N  G  G  A  G  G  A  G  L  W  G  S  220
 661 ggcggcagcggcggccaaggcggcaacggtctgaccggcaacgacggcgtgaatccggcc
     G  G  S  G  G  Q  G  G  N  G  L  T  G  N  D  G  V  N  P  A  240
 721 cccgtcacaaaccccgcgctaaatggcgccgccggcgacagcaatatcgagccgcaaacc
     P  V  T  N  P  A  L  N  G  A  A  G  D  S  N  I  E  P  Q  T  260
 781 agcgtcctgatcggcacccaaggcggtgacggcacgcccggggggtgctggcgtcaacggc
     S  V  L  I  G  T  Q  G  G  D  G  T  P  G  G  A  G  V  N  G  280
 841 ggcaacggtggcgcgggcggagacgccaatggcaaccccgcaaacacctcgatcgccaac
     G  N  G  G  A  G  G  D  A  N  G  N  P  A  N  T  S  I  A  N  300
 901 gcaggcgccggcgggaacggcgccgccggcggtgacggcggtgccaatggcggtgcgggc
     A  G  A  G  G  N  G  A  A  G  G  D  G  G  A  N  G  G  A  G  320
 961 ggcgccggcgggcaggccgcgtccgccggtagttccgtcggcggtgacggcggcaacggc
     G  A  G  G  Q  A  A  S  A  G  S  S  V  G  G  D  G  G  N  G  340
1021 ggtgccggcggtacgggcacgaacgggcacgccggcggtgcggcggcgccggcggtgcc
     G  A  G  G  T  G  T  N  G  H  A  G  G  A  G  G  A  G  G  A  360
1081 ggtggtcgcggcgggtggctggtcggcaacggtggcaacggtggcaacggtgccgccggc
     G  G  P  G  G  W  L  V  G  N  G  G  N  G  G  N  G  A  A  G  380
1141 ggcaacggcgccatcggcggtaccggtggtgccggcggcgtccccgccaaccagggcggt
     G  N  G  A  I  G  G  T  G  G  A  G  G  V  P  A  N  Q  G  G  400
1201 aacagcgccctaggcacccagccggtcggcggcgacggcggcgacggcggcaacggggc
     N  S  A  L  G  T  Q  P  V  G  G  D  G  G  D  G  G  N  G  G  420
1261 accggaggcaccggcggcgtggcggcgacggcggatccggcggcgcggcggcgcgagc
     T  G  G  T  G  G  R  G  G  D  G  G  S  G  G  A  G  G  A  S  440
1321 ggttggttgatgggcaacggcggcaacggcggcaacggcggcaccggcggctcaggcggt
     G  W  L  M  G  N  G  G  N  G  G  N  G  G  T  G  G  S  G  G  460
1381 gtcggcggcaatggcggcatcggcggtgacggcgccggcggcggaaacgccacgagcacg
     V  G  G  N  G  G  I  G  D  G  A  G  G  N  A  T  S  T  480
```

FIG. 16A

```
1441 tcgagcatcccttcgacgcccacgggggtaacggcggcgctggtggcgacgctggtcac
     S   S  I  P  F  D  A  H [G  N][G  A][G  D ]A  G  H    500
1501 ggcggaacgggcggcgacggcggtgacgggggggcatgccggcaccggtggacgtggcgg
     [G  T][G  D][G  D][G  H]A  G  T [G  R][G  G]           520
1561 ttactggccggccagcacgccaactccggcaatggcggtggcggcggtaccggcggtgcc
     L  L  A  G  Q  H  A  N  S  G  N [G  G][G  T][G  A]     540
1621 ggggcacccatggcacccccggcagcggcaacgcaggcggcaccggcaccggtaacgct
     [G  T] H  G  T  P  G  S  G  N  A [G  T] G  T  G  N  A  560
1681 gacagcacaaacggcgggccaggcagcgacggcctcggcggggacgcgtttaacggcagt
     D  S  T  N  G  G  P  G  S  D  G  L [G  D] A  F  N  G  S  580
1741 cgcggcaccgacggcaacccggctaa
     R  G  T  D  G  N  P  G  *                              588
```

FIG. 16B

```
  1 atggacgtcgctttgggggttgcggtcacggatcgggtcgcgcgtctggcgctggtcgac
    M  D  V  A  L  G  V  A  V  T  D  R  V  A  R  L  A  L  V  D   20
 61 tcggctgcgcccggcaccgtgatcgaccagttcgtgctcgatgtggccgagcacccggtc
    S  A  A  P  G  T  V  I  D  Q  F  V  L  D  V  A  E  H  P  V   40
121 gaggtgttaaccgagaccgtggtgggcacggatcggtcattggccggcgaaaaccaccgg
    E  V  L  T  E  T  V  V  G  T  D  R  S  L  A  G  E  N  H  R   60
181 ctggtcgctacccggctgtgttggccggatcaggccaaagctgacgagctgcagcacgca
    L  V  A  T  R  L  C  W  P  D  Q  A  K  A  D  E  L  Q  H  A   80
241 ctgcaggactccggggtccacgacgttgccgtgatatccgaggcgcaggccgccacggcg
    L  Q  D  S  G  V  H  D  V  A  V  I  S  E  A  Q  A  A  T  A  100
301 ctggtcggggcggcacatgccggctctgccgtgctgttggtgggtgatgagacggcaacc
    L  V  G  A  A  H  A  G  S  A  V  L  L  V  G  D  E  T  A  T  120
361 ttatcggtggttggtgacccggacgcgccgccgacgatggtggccgtcgcgccggtggcg
    L  S  V  V  G  D  P  D  A  P  P  T  M  V  A  V  A  P  V  A  140
421 ggcgccgacgccacatcgaccgtcgatacccTgatggcccggctcggcgaccaggccctc
    G  A  D  A  T  S  T  V  D  T  L  M  A  R  L  G  D  Q  A  L  160
481 gccccgggggatgtcttcctggtggggtaggtccgccgagcacaccacggttcttgccgac
    A  P  G  D  V  F  L  V  G  R  S  A  E  H  T  T  V  L  A  D  180
541 cagctgcgcgcggcgtcgacgatgcgcgtgcagactcccgacgaccccacgttcgcgctg
    Q  L  R  A  A  S  T  M  R  V  Q  T  P  D  D  P  T  F  A  L  200
601 gcccgtggcgcggcgatggcggccggcgccgctacgatggcgcacccggccctggtcgcg
    A  R  G  A  A  M  A  A  G  A  A  T  M  A  H  P  A  L  V  A  220
661 gatgcgaccacttcgctcccccgggccgaggcggggcaatcggggttctgaaggcgagcag
    D  A  T  T  S  L  P  R  A  E  A  G  Q  S  G  S  E  G  E  Q  240
721 ctggcgtactcgcaggccagcgattacgagctgcttccggtcgacgaatatgaggaacac
    L  A  Y  S  Q  A  S  D  Y  E  L  L  P  V  D  E  Y  E  E  H  260
781 gacgaatacggggcagccgcggatcgctcggcgccgttgagccgacggtcgctgctgatc
    D  E  Y  G  A  A  A  D  R  S  A  P  L  S  R  R  S  L  L  I  280
841 ggcaacgctgtcgtggcctttgcggtgatcggtttcgcctcgctggcggtggcggtggcg
    G  N  A  V  V  A  F  A  V  I  G  F  A  S  L  A  V  A  V  A  300
901 gtcaccatccgaccgaccgcggcctcaaaaccggtagagggacaccaaaacgcccagcca
    V  T  I  R  P  T  A  A  S  K  P  V  E  G  H  Q  N  A  Q  P  320
961 gggaagttcatgccgttgttgccgacgcaacagcaggcgccggtcccgccg ctccgccc
    G  K  F  M  P  L  L  P  T  Q  Q  Q  A  P  V  P  P    P  P  P 340
1021 gatgatcccaccgctggattccagggcggcaccattccggctgtacagaacgtggtgccg
     D  D  P  T  A  G  F  Q  G  G  T  I  P  A  V  Q  N  V  V  P  360
1081 cggccgggtacctcacccggggtgggtgggacgccggcttcgcctgcgccggaagcgccg
     R  P  G  T  S  P  G  V  G  G  T  P  A  S  P  A  P  E  A  P  380
1141 gccgtgcccggtgttgtgcctgccccggtgccaatcccggtcccgatcatcattccccccg
     A  V  P  G  V  V  P  A  P  V  P  I  P  V  P  I  I  I  P  P  400
1201 ttcccggggttggcagcctggaatgccgaccatccccaccgcaccgccgacgacgccggtg
     F  P  G  W  Q  P  G  M  P  T  I  P  T  A  P  P  T  T  P  V  420
1261 accacgtcggcgacgacgccgccgaccacgccgccgaccacgccggtgaccacgccgcca
     T  T  S  A  T  T  P  P  T  T  P  P  T  T  P  V  T  T  P  P  440
1321 acgacgccgccgaccacgccggtgaccacgccgccaacgacgccgccgaccacgccggtg
     T  T  P  P  T  T  P  V  T  T  P  P  T  T  P  P  T  T  P  V  460
1381 accacgccaccaacgaccgtcgccccgacgaccgtcgccccgacgacggtcgctccgacc
     T  T  P  P  T  T  V  A  P  T  T  V  A  P  T  T  V  A  P  T  480
```

FIG. 17A

```
1441 accgtcgccccgaccacggtcgctccagccaccgccacgccgacgaccgtcgctccgcag
      T  V  A  P  T  T  V  A  P  A  T  A  T  P  T  T  V  A  P  Q  500
1501 ccgacgcagcagcccacgcaacaaccaacccaacagatgccaacccagcagcagaccgtg
      P  T  Q  Q  P  T  Q  P  T  Q  Q  M  P  T  Q  Q  Q  T  V  520
1561 gccccgcagacggtggcgccggctccgcagccgccgtccggtggccgcaacggcagcggc
      A  P  Q  T  V  A  P  A  P  Q  P  P  S  G  G  R  N  G  S  G  540
1621 gggggcgacttattcggcggggttctga
      G  G  D  L  F  G  G  F  *
```

FIG. 17B

MYCOBACTERIAL PROTEINS AS EARLY ANTIGENS FOR SERODIAGNOSIS AND VACCINES

BACKGROUND OF THE INVENTION

1. Field of the Invention

The invention in the fields of microbiology and medicine relates to methods for rapid early detection of mycobacterial disease in humans based on the presence of antibodies to particular "early" mycobacterial antigens which have not been previously recognized for this purpose. Assay of such antibodies on select partially purified or purified mycobacterial preparations containing such early antigens permits diagnosis of TB earlier than has been heretofore possible. Also provided is a surrogate marker for screening populations at risk for TB, in particular subjects infected with human immunodeficiency virus (HIV). The invention is also directed to vaccine compositions and methods useful for preventing or treating TB.

2. Description of the Background Art

The incidence of tuberculosis has shown a rapid increase in recent years, not only in the developing countries, but also in crowded urban settings in the US and in specific subsets of our society, including the homeless, IV drug users, HIV-infected individuals, immigrants and refugees from high prevalence endemic countries (Raviglione, M C et al., 1995. JAMA. 273:220-226). Studies show that these populations are at a significantly greater risk of developing tuberculosis, and also serve as the reservoir of infection for the community as a whole (Raviglione, M C et al., 1992, Bull World Health Organization. 70:515-526; Raviglione, M C et al., 1995. JAMA. 273:220-226). None of the currently used methods for diagnosis of tuberculosis identify individuals with active but sub-clinical infection, and the disease is generally detected when the individuals are already infectious. Design of new diagnostic assays requires knowledge of antigens expressed by the bacteria during their in vivo survival. Most current studies of antigens of *Mycobacterium tuberculosis* (Mtb); also abbreviated herein are focused on antigens present in the culture filtrates of bacteria replicating actively in vitro, with the presumption that the same molecules are expressed by the in vivo bacteria.

A vast majority of the Mtb infected individuals develop immune responses that arrest progression of infection to clinical TB, and also prevent the latent bacilli from reactivating to cause clinical disease, whereas about 10-15% of the infected individuals progress to developing primary or reactivation TB. Understanding the host-pathogen interactions that occur after infection, but prior to development of clinical TB (pre-clinical TB) is required both for the design of effective vaccines and for development of diagnosis of early disease.

Several studies have shown that Mtb adapts to different environments in broth media (Garbe, T R et al., 1999, Infect. Immun. 67:460-465; Lee, B-Y et al., 1995, J. Clin. Invest. 96:245-249; Wong, D K et al., 1999, Infect. Immun. 67:327-336) and during intracellular residence by altering its gene expression (8, 22, 34).

Clark-Curtiss, J E et al., 1999, p. 206-210. In Proceedings of Thirty-Fourth Tuberculosis-Leprosy Research Conference, San Francisco, Calif., Jun. 27-30.

Lee et al., supra; Smith, I et al., 1998, Tuber. Lung Dis. 79:91-97). Earlier studies from the present inventors' laboratory with cavitary and non-cavitary TB patients have also shown that the in vivo environment in which the bacilli replicate affects the profile of the antigenic proteins expressed by Mtb (Samanich, K M et al., 1998, J. Infect. Dis. 178:1534-1538; Laal et al., U.S. Pat. No. 6,245,331 (2001)).

One objective of the present invention was to identify the antigens expressed by inhaled Mtb during the pre-clinical stages of TB. There are no markers to identify non-diseased humans with an active infection with Mtb, but the rabbit model of TB closely resembles TB in immuno-competent humans in that both species are outbred, both are relatively resistant to Mtb, and in both the caseous lesions may liquify and form cavities (Converse, P J et al., 1996, Infect. Immun. 64:4776-4787). Studies have shown that on being inhaled, the bacilli are phagocytosed by (non specifically) activated alveolar macrophages (AM) which either destroy or allow them to multiply. If the bacilli multiply, the AM die and the released bacilli are phagocytosed by non activated monocyte/macrophages that emigrate from the bloodstream. Intracellular replication and host cell death continue for 3-5 weeks, when both cellular and humoral immune responses are elicited (Lurie, M B, 1964. Chapter VIII, p. 192-222, In M. B. Lurie (ed.) Resistance to tuberculosis: experimental studies in native and acquired defensive mechanisms. Harvard University Press, Cambridge, Mass.; Lurie, M B et al., 1965, Bact. Rev. 29:466-476; Dannenberg, A M., Jr., 1991, Immunol. Today. 12:228-233). Lymphocytes and macrophages enter the foci of infection, and if they become activated bacillary replication is controlled, if not, the infection progresses to clinical disease. During these initial stages of bacillary replication and immune stimulation, there are no outward signs of disease except the conversion of cutaneous reactivity to PPD. The antigens of Mtb expressed, and their interaction with the immune system during these pre-clinical stages of TB is not delineated.

SUMMARY OF THE INVENTION

In view of the paucity of human material available to study the immunological events occurring after inhalation of virulent bacilli, but prior to development of clinical TB, the present invention is based in part on studies of aerosol infected rabbits. The present inventors reasoned that by 3-5 weeks post-infection, the sera from infected rabbits would contain antibodies to the antigens being expressed by the in vivo bacteria.

Four antigens of Mtb that are expressed in vivo after aerosol infection, but prior to development of clinical TB, in rabbits were identified by immunoscreening an expression library of Mtb genomic DNA with sera obtained 5 weeks post-infection. Three of the proteins identified, PirG (Rv3810) [SEQ ID NO:1 and 2; nucleotide and amino acid], PE-PGRS (Rv3367) [SEQ ID NO:3 and 4] and PTRP (Rv0538) [SEQ ID NO:5 and 6] have multiple tandem repeats of unique amino-acid sequences, and have characteristics of surface or secreted proteins. The fourth protein, MtrA (Rv3246c) [SEQ ID NO:7 and 8], is a response regulator of a putative two-component signal transduction system, mtrA-mtrB, of Mtb. All four antigens were recognized by pooled sera from TB patients and not from healthy controls, confirming their in vivo expression during active infection in humans. Three of the antigens, (PE-PGRS, PTRP and MtrA) were also recognized by retrospective, pre-clinical TB sera obtained from HIV-TB patients prior to the clinical manifestation of TB, suggesting their utility as diagnostics for active, pre-clinical ("early") TB.

The present invention provides methods, kits and compositions directed to the detection of antibodies or T cell reactivity to any of the above early antigens or to the detection of the antigens themselves in a body fluid of a subject as a means of detecting early mycobacterial disease in the subject. In other embodiments, the invention provides, methods, kits and compositions useful for detecting antibody or T cell reactivity to, in addition to one or more of the above early antigens, to one or more of the following early Mtb antigens:
(a) an 88 kDa *M. tuberculosis* protein having the an amino acid sequence SEQ ID NO:13:

```
MTDRVSVGNL RIARVLYDFV NNEALPGTDI DPDSFWAGVD KVVADLTPQN QALLNARDEL
QAQIDKWHRR RVIEPIDMDA YRQFLTEIGY LLPEPDDFTI TTSGVDAEIT TTAGPQLVVP
VLNARFALNA ANARWGSLYD ALYGTDVIPE TDGAEKGPTY NKVRGDKVIA YARKFLDDSV
PLSSGSFGDA TGFTVQDGQL VVALPDKSTG LANPGQFAGY TGAAESPTSV LLINHGLHIE
ILIDPESQVG TTDRAGVKDV ILESAITTIM DFEDSVAAVD AADKVLGYRN WLGLNKGDLA
AAVDKDGTAF LRVLNRDRNY TAPGGGQFTL PGRSLMFVRN VGHLMTNDAI VDTDGSEVFE
GIMDALFTGL IAIHGLKASD VNGPLINSRT GSIYIVKPKM HGPAEVAFTC ELFSRVEDVL
GLPQNTMKIG IMDEERRTTV NLKACIKAAA DRVVFINTGF LDRTGDEIHT SMEAGPMVRK
GTMKSQPWIL AYEDHNVDAG LAAGFSGRAQ VGKGMWTMTE LMADMVETKI AQPRAGASTA
WVPSPTAATL HALHYHQVDV AAVQQGLAGK RRATIEQLLT IPLAKELAWA PDEIREEVDN
NCQSILGYVV RWVDQGVGCS KVPDIHDVAL MEDRATLRIS SQLLANWLRH GVITSADVRA
SLERMAPLVD RQNAGDVAYR PMAPNFDDSI AFLAAQELIL SGAQQPNGYT EPILHRRRRE
FKARAAEKPA PSDRAGDDAA R
```

(b) a 27 kDa *M. tuberculosis* protein named MPT51 having the amino acid sequence SEQ ID NO:14:

```
APYENLMVPS PSMGRDIPVA FLAGGPHAVY LLDAFNAGPD VSNWVTAGNA
NTLAGKGIS VVAPAGGAYS MYTNWEQDGS KQWDTFLSAE LPDWLAANRG
AAQGGYGAMA AAFHPDRFG FAGSMSGFLY PSNTTTNGAI AAGMQQFGGV
DTNGMWGAPQ LGRWKWHDPW HASLLAQNN TRVWVWSPTN PGASDPAAMI
GQTAEAMGNS RMFYNQYRSV GGHNGHFDFP SGDNGWGSW APQLGAMSGD IVGAIR;
```

(c) a protein characterized as *M. tuberculosis* antigen 85C; or (d) a glycoprotein characterized as *M. tuberculosis* antigen MPT32.

In yet another embodiment, the invention provides methods, kits and compositions useful for the detection of antibodies or T cell reactivity to any of the above early antigens or to one or more of the following early antigens:

(i) a 28 kDa protein corresponding to the spot identified as Ref. No. 77 in Table 2.

(ii) a 29/30 kDa protein corresponding to the spot identified as Ref No. 69 or 59 in Table 2;

(iii) a 31 kDa protein corresponding to the spot identified as Ref. No. 103 in Table 2;

(iv) a 35 kDa protein corresponding to the spot identified as Ref. No. 66 in Table 2 and reacting with monoclonal antibody IT-23;

(v) a 42 kDa protein corresponding to the spot identified as Ref. No. 68 or 80 in Table 2;

(vi) a 48 kDa protein corresponding to the spot identified as Ref. No. 24 in Table 2; and (vii) a 104 kDa protein corresponding to the spot identified as Ref. No. 111 in Table 2, which spots are obtained by 2-dimensional electrophoretic separation of *M. tuberculosis* lipoarabinomannan-free culture filtrate proteins as follows:

(A) incubating 3 hours at 20° C. in 9M urea, 2% Nonidet P-40, 5% β-mercaptoethanol, and 5% ampholytes at pH 3-10;

(B) isoelectric focusing on 6% polyacrylamide isoelectric focusing tube gel of 1.5 mm×6.5 cm, said gel containing 5% ampholytes in a 1:4 ratio of pH 3-10 ampholytes to pH 4-6.5 ampholytes for 3 hours at 1 kV using 10 mM $H_3PO_4$ as catholyte and 20 mM NaOH as anolyte, to obtain a focused gel;

(C) subjecting the focused gel to SDS PAGE in the second dimension by placement on a preparative SDS-polyacrylamide gel of 7.5×10 cm×1.5 mm containing a 6% stack over a 15% resolving gel and electrophoresing at 20 mA per gel for 0.3 hours followed by 30 mA per gel for 1.8 hours.

In yet other embodiments, the present invention provides vaccines compositions and methods for treating or preventing mycobacterial disease in a subject. The vaccine composition may comprise any one or more of the early antigens noted above or an epitope thereof. Preferred vaccine epitopes are T helper epitopes, more preferably T helper epitopes that stimualte Th1 cells.

BRIEF DESCRIPTION OF THE DRAWINGS

FIG. 1 shows reactivity of guinea pig serum pool with antigen for Mtb (see description below figure)

FIGS. 2*a*-2*d* show reactivity of fusion proteins from individual colonies of gsrI-3, I-6, II-1 and II-1 (see description below figure)

FIG. 4b shows the amino acid sequence of protein encoded by MTV-=004.03. Peptides encoded by clones gsr I-6 and gsr II-2 are shown in bold. The 6 copies of the repeat motif in gsr I-6 are underlined.

Figure 5A:
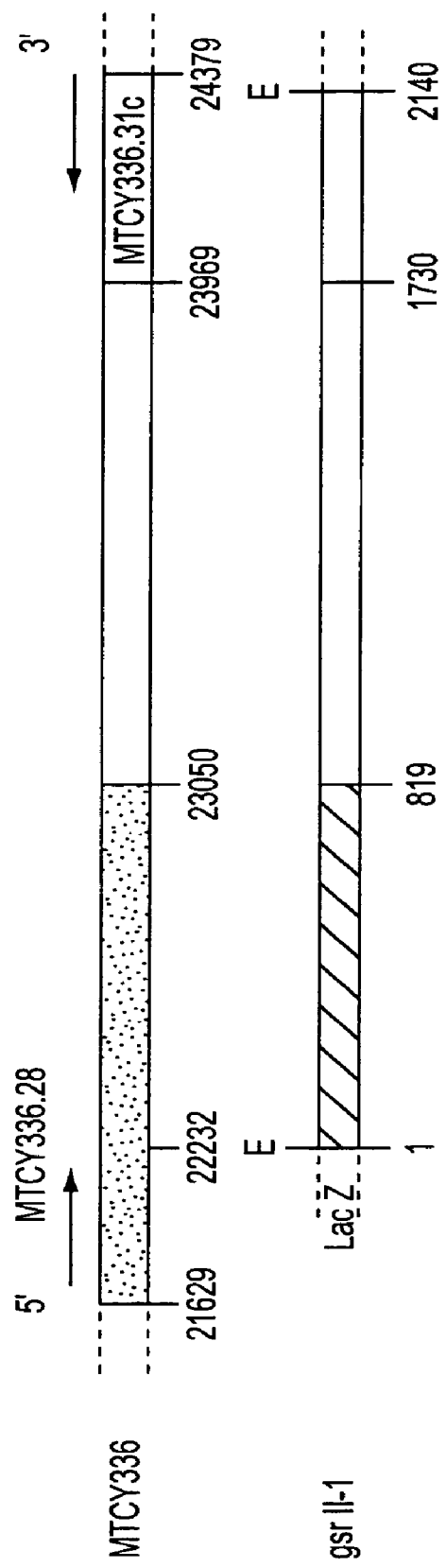

FIG. 5a shows sequence alignment of clone gsr II-1 with cosmid MTCY336.

FIG. 5b shows amino acid sequence of MTCY336.28. Peptide encoded by clone gsr II-2 is shown in bold.

Figures 6A, 6B, 6C:
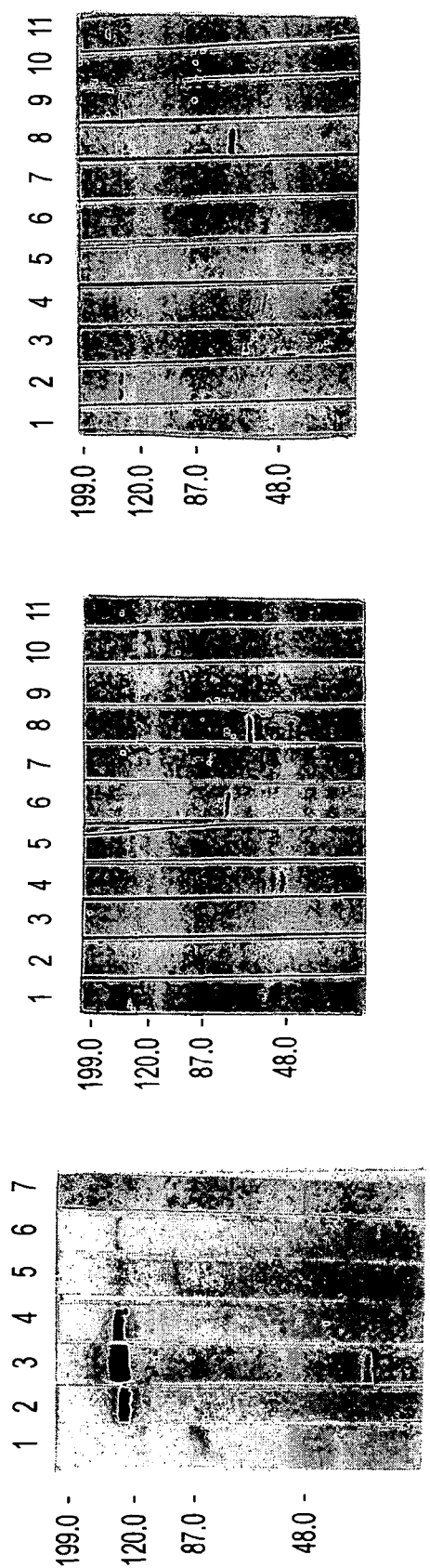

FIGS. 6A, 6B and 6C shows reactivity of fusion proteins of gsrI-6, II-1 and II-1 with sera from individual guinea pigs (see description below figures).

Figure 7B:
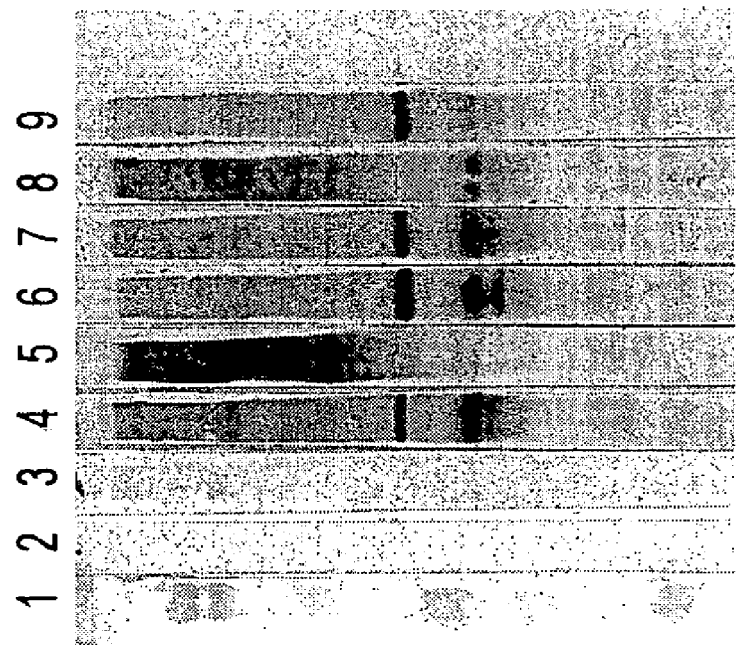
Figure 7A:
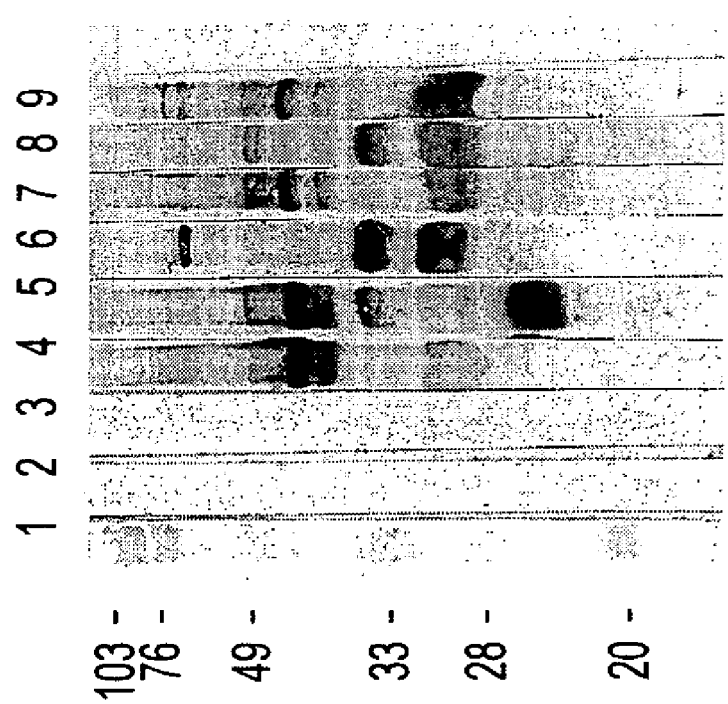

FIGS. 7A and 7B show a comparison of reactivity of Mtb infected guinea pig and human sera with culture filtrate proteins (7A) and SDS-soluble cell wall proteins (7B) of Mtb (see description below figure).

Figures 8A, 8B:
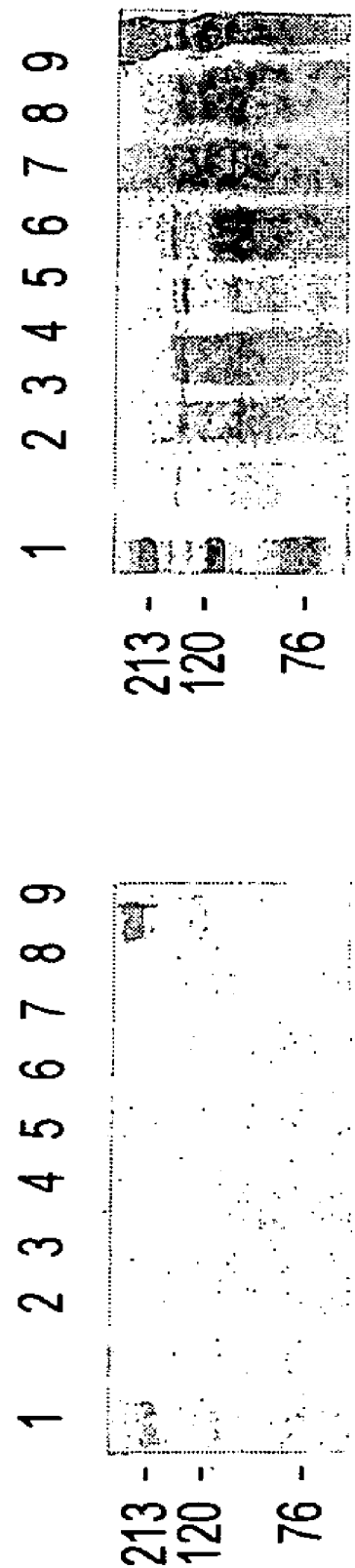

FIGS. 8A and 8B shows reactivity of a pool of sera from PPD+ healthy individuals (8A) or from TB patients (8B) (see description below figure)

Figure 9:
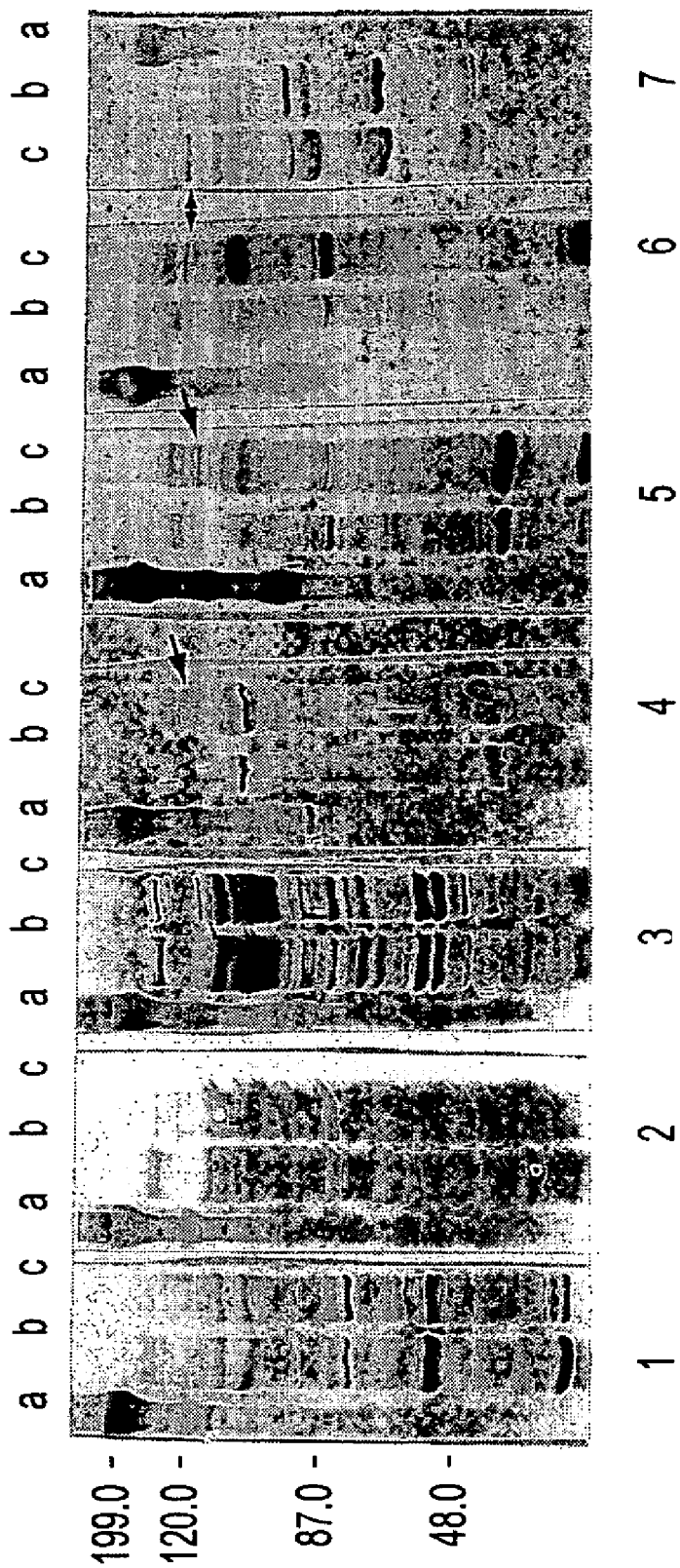
Figure 11C:
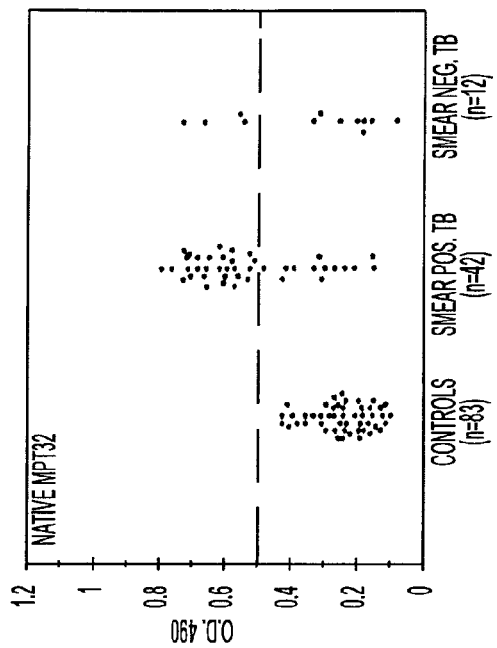
Figure 11D:
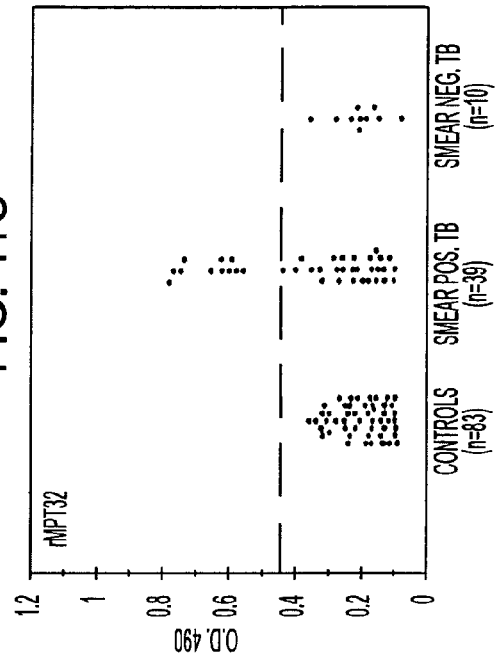
Figure 11A:
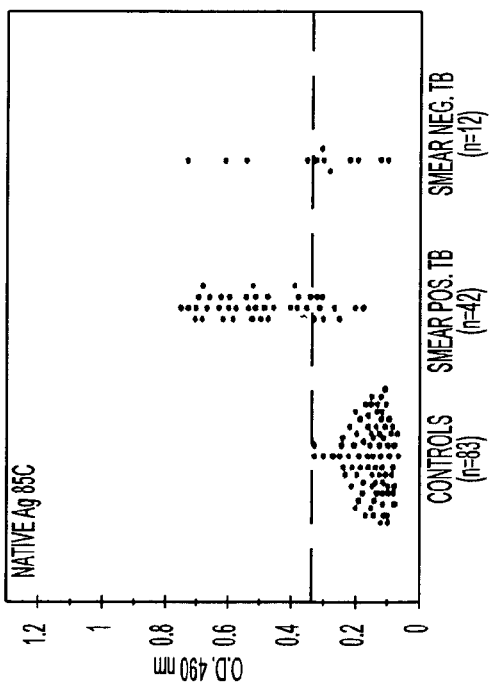
Figure 11B:
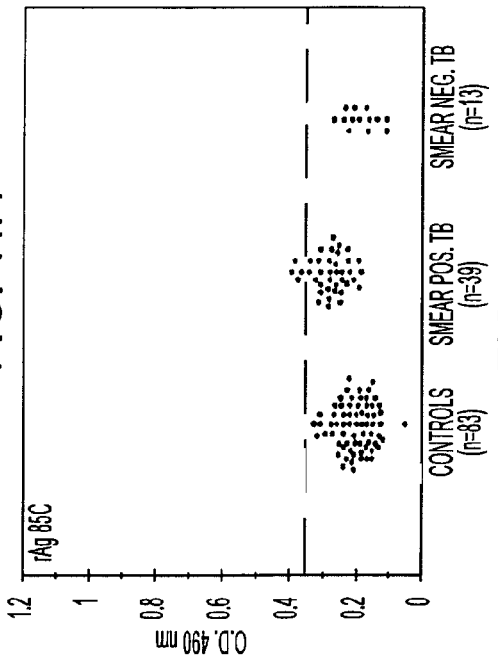

FIG. 9 shows reactivity of sera from PPD+ individuals and TB patients with gsr I-6 lysates (see description below figure)

FIG. 10 (shows reactivity of HIV pre-TB serum pool with fusion proteins expressed by the various gsr clones (see description below figure).

FIG. 11 shows a comparison of reactivity of TB sera with native and recombinant Mtb antigens (see description below figure).

Figure 12B:
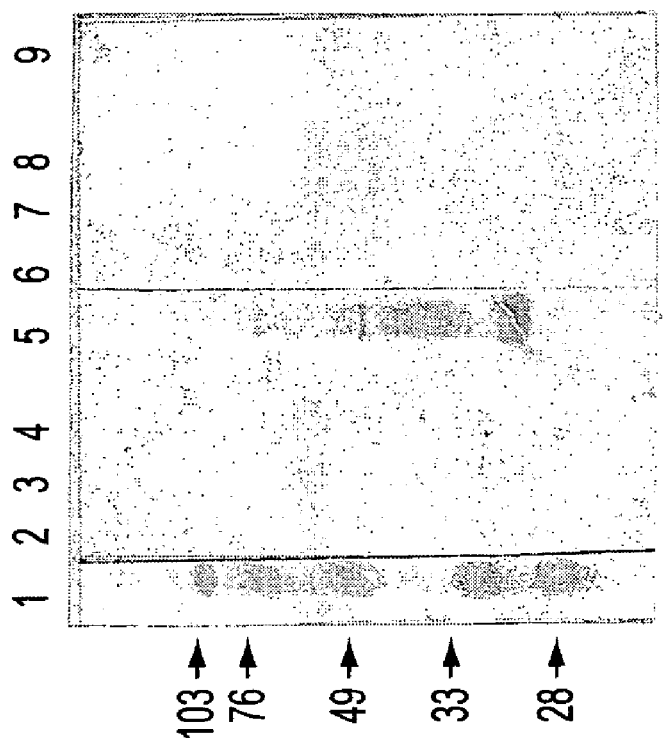
Figure 12A:
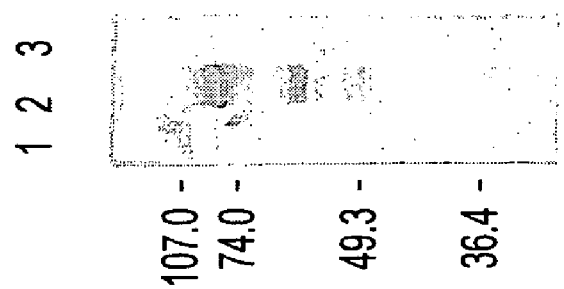

FIG. 12A shows expression of the 88 kDa seroreactive antigen in *M. smegmatis* (see description below figure).

FIG. 12B shows reactivity of sera form a TB patient and a PPD+ healthy control with 30-fold concentrated culture filtrate of *M. smegmatis* (see description below figure).

Figure 13:
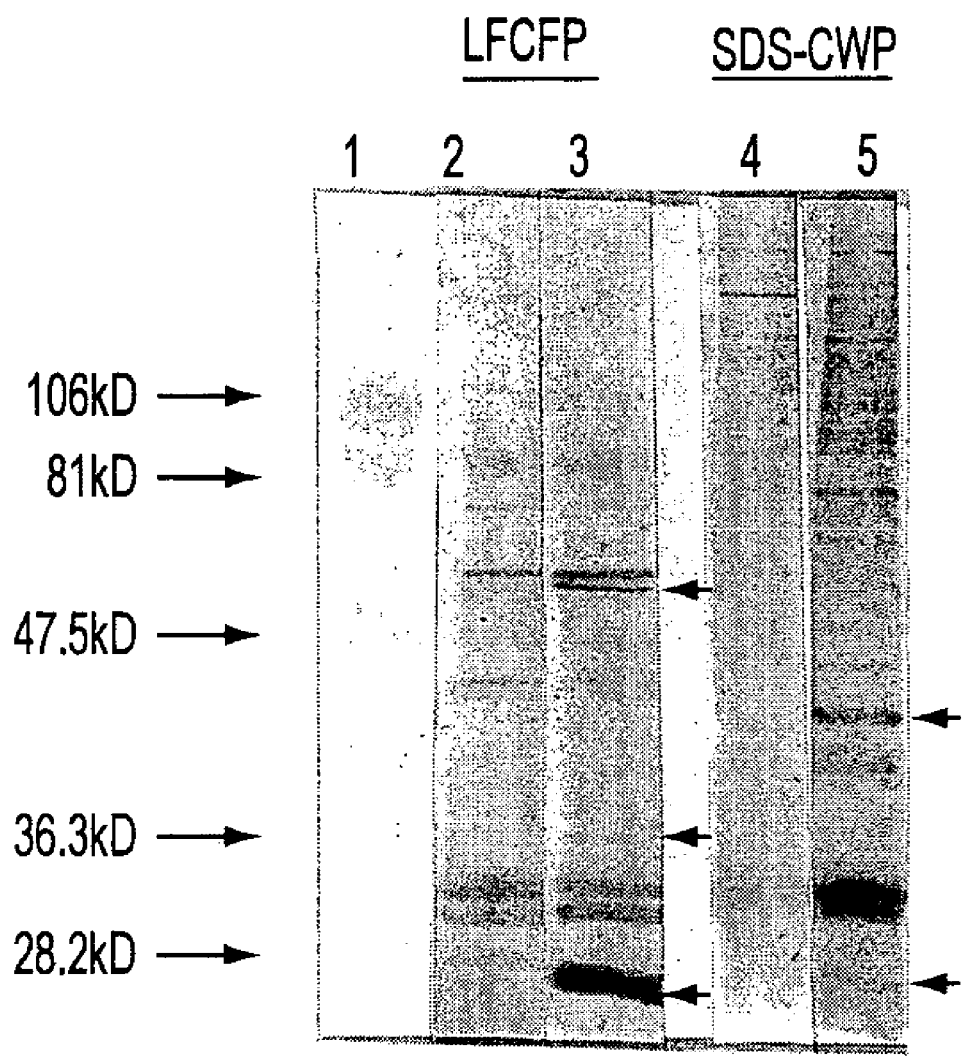

FIG. 13 Reactivity of Mtb antigens with pooled sera from rabbits. LFCFP (lanes 2 & 3 and SDS-CWP (lanes 4 & 5) proteins of Mtb were fractionated on 10% SDS-PA gels, and western blots probed with pooled sera from uninfected (lanes 2 & 4) and Mtb infected (lanes 3 & 5) rabbits. Lane 1 contains molecular weight markers.

Figure 14:
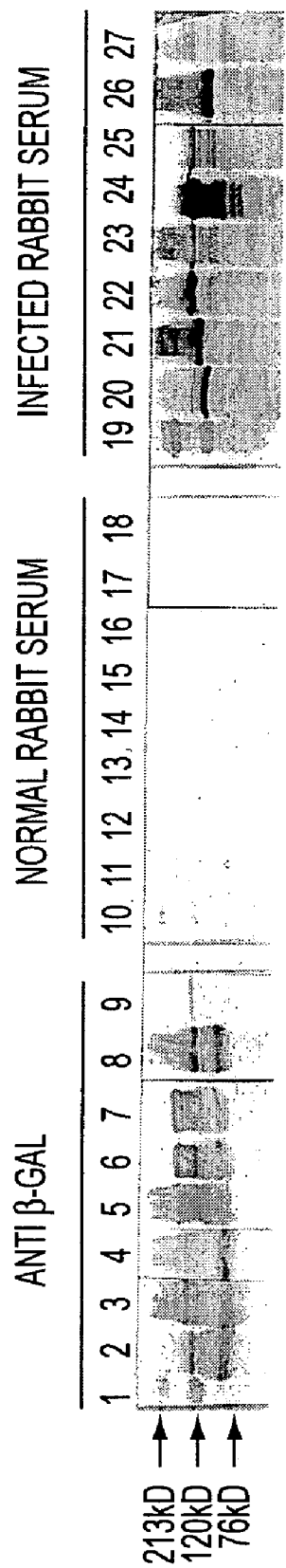

FIG. 14: Reactivity of β-gal fusion proteins of AD clones with anti β-gal antibody and sera from Mtb infected rabbits. Lysates of AD lysogens and λgt11 vector lysogen were separated on 10% SDS-PA gels and probed with anti-β-gal antibody (lanes 2-9), uninfected rabbit sera (lanes 11-18) and infected rabbit sera (lanes 19-27). Lanes; 1, 10 & 19 contain molecular weight markers; lanes 2, 11 & 20: lysates from clone AD 1; lanes 3, 12 & 21: clone AD2, lanes 4; 13 &22: clone AD4; lanes 5, 14 & 23: clone AD9; lanes 6, 15 & 24: clone AD10; lanes 7, 16 & 25: clone AD7; lanes 8, 17 & 26: clone AD16 and lanes 9, 18 & 27: λgt11 vector.

FIG. 15: Schematic maps showing position of AD clones on cosmids of Mtb H37Rv. A: map of clones AD1 & AD2 on cosmid MTV026 and MTCY409. B: clone AD9 on cosmid MTV004. C: clone AD10 on cosmid MTY25D10. D: clone AD16 on cosmid MTY20B11. Black bar represents the gene on the cosmid. Hatched bar shows regions expressed as β-gal fusion protein in AD clones. Arrow indicates direction of translation. E denotes EcoRI site.

FIG. 16: Nucleotide and deduced amino acid sequence of gene Rv3367 (PE_PGRS) (SEQ ID NO: 3 and 4, respectively). The signal peptide sequence is shown in italics, hollow arrow between aa 44 & 45 indicates signal peptidase cleavage site. The repetitive sequences are shown in boxes. The motif PE is underlined. Solid arrow at aa 230 indicates the start of fusion with β-gal in clone AD9. The transmembrane helices sequences are shown in bold. The asterisk indicates the termination codon.

FIG. 17: Nucleotide and deduced amino acid sequence of gene Rv0538 (PTRP) (SEQ ID NO: 5 and 6, respectively). The repetitive motifs are shown in boxes. Arrow indicates the initiation of fusion with β-gal in clone AD10. The transmembrane helices sequences are shown in bold. The asterisk indicates the termination codon.

FIG. 18: Reactivity of β-gal fusion proteins with human sera. Blot A: clone AD9 (PE_PGRS), B: clone AD10 (PTRP), C: clone AD2 (pirG) and D: clone AD16 (MtrA). Lanes 1, 4, 7, 10 & 13: molecular weight markers; lanes 2, 5, 8, 11 & 14: lysates form lysogens of respective AD clones; lanes 3, 6, 9, 12 & 15: lysogen of λgt11 vector. Lanes 2 & 3 probed with anti β-gal antibody, lanes 5 & 6 with pooled sera from PPD positive healthy individuals, lanes 8 & 9 with pooled sera from HIV pre-TB individuals, lanes 11 & 12 with pooled sera from non-cavitary TB individuals and lanes 14 & 15 with pooled sera from cavitary TB individuals.

Figure 19A:
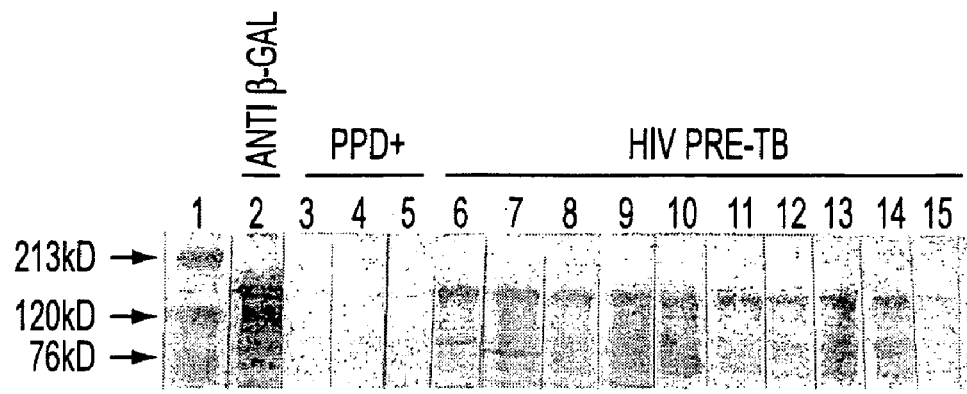
Figure 19B:
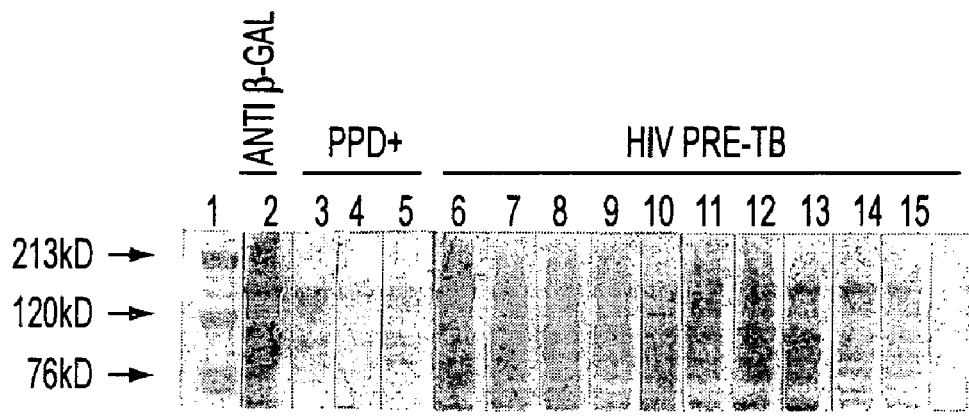

FIG. 19: Reactivity of β-gal fusion proteins of AD clones with sera from HIV pre-TB individuals. A: clone AD9 (PE_PGRS), B: clone AD10 (PTRP) and C: clone AD16 (MtrA). Lane 1; molecular weight marker; lanes 2-15: lysates from lysogens of respective AD clones. Lane 2 is probed with anti β-gal antibody in each case, lanes 3-5 with sera from three PPD positive healthy individuals and lanes 6-15 with sera from 10 HIV pre-TB individuals.

DESCRIPTION OF THE PREFERRED EMBODIMENTS

This Application incorporates by reference, in their entirety, U.S. Pat. No. 6,245,331 (12 Jun. 2001) and U.S. Pat. No. 6,506,384. Also incorporated by reference are all references cited therein.

In the following description, reference will be made to various methodologies known to those of skill in the art of immunology. Publications and other materials setting forth such known methodologies to which reference is made are incorporated herein by reference in their entireties as though set forth in full. Standard reference works setting forth the general principles of immunology include Roitt, I., *Essential Immunology*, 6th Ed., Blackwell Scientific Publications, Oxford (1988); Roitt, I. et al., *Immunology*, C. V. Mosby Co., St. Louis, Mo. (1985); Klein, J., Immunology, Blackwell Scientific Publications, Inc., Cambridge, Mass., (1990); Klein, J., *Immunology: The Science of Self-Nonself Discrimination*, John Wiley & Sons, New York, N.Y. (1982)); and Eisen, H. N., (In: *Microbiology,* 3rd Ed. (Davis, B. D., et al., Harper & Row, Philadelphia (1980)); A standard work setting forth details of mAb production and characterization, and immunoassay procedures, is Hartlow, E. et al., *Antibodies: A Laboratory Manual*, Cold Spring Harbor Laboratory Press, Cold Spring Harbor, N.Y., 1988.

As used herein, the term "early" and "late" in reference to (1) Mtb infection or disease, or the subject having the infection or disease, (2) the antibody response to an Mtb antigen, (3) an Mtb antigen itself or (4) a diagnostic assay, are defined in terms of the stage of development of TB. Early and late (or advanced) TB are defined in the table below.

Thus, a subject with early TB is asymptomatic or, more typically, has one or more "constitutional symptoms" (e.g., fever, cough, weight loss). In early TB, Mtb bacilli are too few to be detectable as acid-fast bacilli in smears of sputum or other body fluid, primarily those fluids associated with the lungs (such as bronchial washings, bronchoalveolar lavage, pleural effusion). However, in these subjects, Mtb bacilli are present and culturable, i.e., can be grown in culture from the above body fluids. Finally, early TB subjects may have radiographically evident pulmonary lesions which may include infiltration but without cavitation. Any antibody present in such early stages is termed an "early antibody" and any Mtb antigen recognized by such antibodies is termed an "early antigen." The fact that an antibody is characterized as "early" does not mean that this antibody is absent in advanced TB. Rather, such antibodies are expected to persist across the progression of early TB to the advanced stage.

| Early TB | 1. Smear of sputum, bronchial washing, bronchoalveolar lavage or pleural effusion is negative for acid fast bacilli<br>2. Direct culture of sputum, bronchial washing, bronchoalveolar lavage or pleural effusion is positive for acid fast bacilli<br>3. Chest x-ray is normal or shows Infiltration in the lungs<br>4. Constitutional symptoms are present (fever, cough, appetite and weight loss) |
|---|---|
| Late/ Advanced TB | 1. Smear of sputum, bronchial washing, bronchoalveolar lavage or pleural effusion is positive (with possible hemoptysis)<br>2. Direct culture of sputum, bronchial washing, bronchoalveolar lavage or pleural effusion is positive<br>3. Chest x-ray shows cavitary lesions in the lungs<br>4. Constitutional symptoms are present (see above) |

Accordingly, the term "late" or "advanced" is characterized in that the subject has frank clinical disease and more advanced cavitary lesions in the lungs. In late TB, Mtb bacilli are not only culturable from smears of sputum and/or the other body fluids noted above, but also present in sufficient numbers to be detectable as acid-fast bacilli in smears of these fluids. Again, "late TB" or "late mycobacterial disease" is used interchangeably with "advanced TB" or "advanced mycobacterial disease." An antibody that first appears after the onset of diagnostic clinical and other characterizing symptoms (including cavity pulmonary lesions) is a late antibody, and an antigen recognized by a late antibody (but not by an early antibody) is a late antigen.

To be useful in accordance with this invention, an early diagnostic assay must permit rapid diagnosis of Mtb disease at a stage earlier than that which could have been diagnosed by conventional clinical diagnostic methods, namely, by radiologic examination and bacterial smear and culture or by other laboratory methods available prior to this invention. (Culture positivity is the final confirmatory test but takes two weeks and more)

An objective of the invention is to define, obtain and characterize the antigens of Mtb expressed by the bacterium in vivo during early tuberculosis. These antigens are evaluated for their utility as markers of early disease that may be used to monitor suspected or high-risk individuals to identify those with active, subclinical infection.

Mycobacterial Antigen Compositions

The preferred mycobacterial antigen composition may be a substantially purified or recombinantly produced preparation of one or more Mtb proteins. Alternatively, the antigen composition may be a partially purified or substantially pure preparation containing one or more Mtb epitopes which are capable of being bound by antibodies or T lymphocytes of an infected subject Such epitopes may be in the form of peptide fragments of the early antigen proteins or other "functional derivatives" of Mtb proteins as described below.

By "functional derivative" is meant a "fragment," "variant," "analogue," or "chemical derivative" of an early antigen protein, which terms are defined below. A functional derivative retains at least a portion of the function of the protein which permits its utility in accordance with the present invention—primarily the capacity to bind to an early antibody. A "fragment" refers to any subset of the molecule, that is, a shorter peptide. A "variant" refers to a molecule substantially similar to either the entire protein or fragment thereof A variant peptide may be conveniently prepared by direct chemical synthesis or by recombinant means. An "analogue" of the protein or peptide refers to a non-natural molecule substantially similar to either the entire molecule or a fragment thereof. A "chemical derivative" of the antigenic protein or peptide contains additional chemical moieties not normally part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Several proteins or glycoproteins, identified in culture filtrates of Mt, or on the surface of Mtb organisms are the preferred early Mtb antigens of the present invention. The secreted proteins may also be present in cellular preparations of the bacilli. Thus, these early antigens are not intended to be limited to the secreted protein form. The proteins are characterized at various places below.

Preferred diagnostic epitopes are those recognized by antibodies or by T cells, preferably Th1 cells of "early" TB patients as defined above. This does not exclude the possibility that such epitopes are bound by antibodies or recognized by T cells present later in the infectious process. In fact, some of the present proteins or epitopes thereof my detect infection in subjects whose infectious state is not detected by antibodies against the 88 kDa protein (malate synthase) described in U.S. Pat. Nos. 6,245,331 and 6,506,384, and their respective file histories.

Preferred vaccine epitopes (see below) are epitopes which stimulate naïve human Th1 cells or Th1 cells or infected subjects to proliferate or to secrete cytokines. Assays for Th1 cytokines, preferably interferon-$\gamma$ (IFN$\gamma$). IL-12 and IL-18 are well-known in the art.

The present immunoassay typically comprises incubating a biological fluid, preferably serum or urine, from a subject suspected of having TB, in the presence of an Mtb antigen-containing reagent which includes one or more Mtb early antigens, and detecting the binding of antibodies in the sample to the mycobacterial antigen(s). By the term "biological fluid" is intended any fluid derived from the body of a normal or diseased subject which may contain antibodies, such as blood, serum, plasma, lymph, urine, saliva, sputum, tears, cerebrospinal fluid, bronchioalveolar lavage fluid, pleural fluid, bile, ascites fluid, pus and the like. Also included within the meaning of this term as used herein is a tissue extract, or the culture fluid in which cells or tissue from the subject have been incubated.

In a preferred embodiment, the mycobacterial antigen composition is brought in contact with, and allowed to bind to, a solid support or carrier, such as nitrocellulose or polystyrene, allowing the antigen composition to adsorb and become immobilized to the solid support. This immobilized antigen is then allowed to interact with the biological fluid sample which is being tested for the presence of anti-Mtb antibodies, such that any antibodies in the sample will bind to the immobilized antigen. The support to which the antibody is now bound may then be washed with suitable buffers after which a detectably labeled binding partner for the antibody is introduced. The binding partner binds to the immobilized antibody. Detection of the label is a measure of the immobilized antibody.

A preferred binding partner for this assay is an anti-immunoglobulin antibody ("second antibody") produced in a different species. Thus to detect a human antibody, a detectably labeled goat anti-human immunoglobulin "second" antibody may be used. The solid phase support may then be washed with the buffer a second time to remove unbound antibody.

The amount of bound label on the solid support may then be detected by conventional means appropriate to the type of label used (see below).

Such a "second antibody" may be specific for epitopes characteristic of a particular human immunoglobulin isotype, for example IgM, $IgG_1$, $IgG_{2a}$, IgA and the like, thus permitting identification of the isotype or isotypes of antibodies in the sample which are specific for the mycobacterial antigen. Alternatively, the second antibody may be specific for an idiotype of the anti-Mtb antibody of the sample.

As alternative binding partners for detection of the sample antibody, other known binding partners for human immunoglobulins may be used. Examples are the staphylococcal immunoglobulin binding proteins, the best known of which is protein A. Also intended is staphylococcal protein G, or a recombinant fusion protein between protein A and protein G. Protein G of group G and group C streptococci binds to the Fc portion of Ig molecules as well as to IgG Fab fragment at the $V_H3$ domain. Protein C of *Peptococcus magnus* binds to the Fab region of the immunoglobulin molecule. Any other microbial immunoglobulin binding proteins, for example from Streptococci, are also intended (for example, Langone, J. J., *Adv. Immunol.* 32:157 (1982)).

In another embodiment of this invention, a biological fluid suspected of containing antibodies specific for a Mtb antigen may be brought into contact with a solid support or carrier which is capable of immobilizing soluble proteins. The support may then be washed with suitable buffers followed by treatment with a mycobacterial antigen reagent, which may be detectably labeled. Bound antigen is then measured by measuring the immobilized detectable label. If the mycobacterial antigen reagent is not directly detectably labeled, a second reagent comprising a detectably labeled binding partner for the Mtb antigen, generally a second anti-Mtb antibody such as a murine mAb, is allowed to bind to any immobilized antigen. The solid phase support may then be washed with buffer a second time to remove unbound antibody. The amount of bound label on said solid support may then be detected by conventional means.

By "solid phase support" is intended any support capable of binding a proteinaceous antigen or antibody molecules or other binding partners according to the present invention. Well-known supports, or carriers, include glass, polystyrene, polypropylene, polyethylene, polyvinylidene difluoride, dextran, nylon, magnetic beads, amylases, natural and modified celluloses, polyacrylamides, agaroses, and magnetite. The nature of the carrier can be either soluble to some extent or insoluble for the purposes of the present invention. The support material may have virtually any possible structural configuration so long as it is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads, 96-well polystyrene microplates and test strips, all well-known in the art. Those skilled in the art will know many other suitable carriers for binding antibody or antigen, or will be able to ascertain the same by use of routine experimentation.

Using any of the assays described herein, those skilled in the art will be able to determine operative and optimal assay conditions for each determination by employing routine experimentation. Furthermore, other steps as washing, stirring, shaking, filtering and the like may be added to the assays as is customary or necessary for the particular situation.

A preferred type of immunoassay to detect an antibody specific for a mycobacterial antigen according to the present invention is an enzyme-linked immunosorbent assay (ELISA) or more generically termed an enzyme immunoassay (EIA). In such assays, a detectable label bound to either an antibody-binding or antigen-binding reagent is an enzyme. When exposed to its substrate, this enzyme will react in such a manner as to produce a chemical moiety which can be detected, for example, by spectrophotometric, fluorometric or visual means. Enzymes which can be used to detectably label the reagents useful in the present invention include, but are not limited to, horseradish peroxidase, alkaline phosphatase, glucose oxidase, β-galactosidase, ribonuclease, urease, catalase, malate dehydrogenase, staphylococcal nuclease, asparaginase, Δ-5-steroid isomerase, yeast alcohol dehydrogenase, α-glycerophosphate dehydrogenase, triose phosphate isomerase, glucose-6-phosphate dehydrogenase, glucoamylase and acetylcholinesterase. For descriptions of EIA procedures, see Voller, A. et al., *J. Clin. Pathol.* 31:507-520 (1978); Butler, J. E., *Meth. Enzymol.* 73:482-523 (1981); Maggio, E. (ed.), *Enzyme Immunoassay*, CRC Press, Boca Raton, 1980; Butler, J. E., In: *Structure of Antigens*, Vol. 1 (Van Regenmortel, M., CRC Press, Boca Raton, 1992, pp. 209-259; Butler, J. E., In: van Oss, C. J. et al., (eds), *Immunochemistry*, Marcel Dekker, Inc., New York, 1994, pp. 759-803; Butler, J. E. (ed.), *Immunochemistry of Solid-Phase Immunoassay*, CRC Press, Boca Raton, 1991)

In another embodiment, the detectable label may be a radiolabel, and the assay termed a radioimmunoassay (RIA), as is well known in the art. See, for example, Yalow, R. et al., Nature 184:1648 (1959); Work, T. S., et al., *Laboratory Techniques and Biochemistry in Molecular Biology*, North Holland Publishing Company, NY, 1978, incorporated by reference herein. The radioisotope can be detected by a gamma counter, a scintillation counter or by autoradiography. Isotopes which are particularly useful for the purpose of the present invention are $^{125}I$, $^{131}I$, $^{35}S$, $^{3}H$ and $^{14}C$.

It is also possible to label the antigen or antibody reagents with a fluorophore. When the fluorescently labeled antibody is exposed to light of the proper wave length, its presence can then be detected due to fluorescence of the fluorophore. Among the most commonly used fluorophores are fluorescein isothiocyanate, rhodamine, phycoerythrin, phycocyanin, allophycocyanin, o-phthaldehyde, fluorescamine or fluorescence-emitting metals such as $^{152}Eu$ or other lanthanides. These metals are attached to antibodies using metal chelators.

The antigen or antibody reagents useful in the present invention also can be detectably labeled by coupling to a chemiluminescent compound. The presence of a chemiluminescent-tagged antibody or antigen is then determined by detecting the luminescence that arises during the course of a chemical reaction. Examples of useful chemiluminescent labeling compounds are luminol, isoluminol, theromatic acridinium ester, imidazole, acridinium salt and oxalate ester. Likewise, a bioluminescent compound such as a bioluminescent protein may be used to label the antigen or antibody reagent useful in the present invention. Binding is measured by detecting the luminescence. Useful bioluminescent compounds include luciferin, luciferase and aequorin.

Detection of the detectably labeled reagent according to the present invention may be accomplished by a scintillation counter, for example, if the detectable label is a radioactive gamma emitter, or by a fluorometer, for example, if the label is a fluorophore. In the case of an enzyme label, the detection is accomplished by colorimetry to measure the colored product produced by conversion of a chromogenic substrate by the enzyme. Detection may also be accomplished by visual comparison of the colored product of the enzymatic reaction in comparison with appropriate standards or controls.

The immunoassay of this invention may be a "two-site" or "sandwich" assay. The fluid containing the antibody being assayed is allowed to contact a solid support. After addition of the mycobacterial antigen(s), a quantity of detectably labeled soluble antibody is added to permit detection and/or quantitation of the ternary complex formed between solid-phase antibody, antigen, and labeled antibody. Sandwich assays are described by Wide, *Radioimmune Assay Method*, Kirkham et aL, Eds., E. & S. Livingstone, Edinburgh, 1970, pp 199-206.

Alternatives to the RIA and EIA are various types of agglutination assays, both direct and indirect, which are well known in the art. In these assays, the agglutination of particles containing the antigen (either naturally or by chemical coupling) indicates the presence or absence of the corresponding antibody. Any of a variety of particles, including latex, charcoal, kaolinite, or bentonite, as well as microbial cells or red blood cells, may be used as agglutinable carriers (Mochida, U.S. Pat. No. 4,308,026; Gupta et al., J. Immunol. Meth. 80:177-187 (1985); Castelan et al., J. Clin. Pathol. 21:638 (1968); Singer et al., Amer. J. Med.(December 1956, 888; Molinaro, U.S. Pat. No. 4,130,634). Traditional particle agglutination or hemagglutination assays are generally faster, but much less sensitive than RIA or EIA. However, agglutination assays have advantages under field conditions and in less developed countries.

In addition to detection of antibodies, the present invention provides methods to detect and enumerate cells secreting an antibody specific for a mycobacterial antigen. Thus, for example, any of a number of plaque or spot assays may be used wherein a sample containing lymphocytes, such as peripheral blood lymphocytes, is mixed with a reagent containing the antigen of interest. As the antibody secreting cells of the sample secrete their antibodies, the antibodies react with the antigen, and the reaction is visualized in such a way that the number of antibody secreting cells (or plaque forming cells) may be determined. The antigen may be coupled to indicator particles, such as erythrocytes, preferably sheep erytirocytes, arranged in a layer. As antibodies are secreted from a single cell, they attach to the surrounding antigen-bearing erythrocytes. By adding complement components, lysis of the erythrocytes to which the antibodies have attached is achieved, resulting in a "hole" or "plaque" in the erythrocyte layer. Each plaque corresponds to a single antibody-secreting cell. In a different embodiment, the sample containing antibody-secreting cells is added to a surface coated with an antigen-bearing reagent, for example, a mycobacterial antigen alone or conjugated to bovine serum albumin, attached to polystyrene. After the cells are allowed to secrete the antibody which binds to the immobilized antigen, the cells are gently washed away. The presence of a colored "spot" of bound antibody, surrounding the site where the cell had been, can be revealed using modified EIA or other staining methods well-known in the art. (See, for example, Sedgwick, J. D. et aL, J. Immunol. Meth. 57:301-309 (1983); Czerkinsky, C. C. et al., J. Immunol. Meth. 65:109-121 (1983); Logtenberg, T. et al., Immunol. Lett. 9:343-347 (1985); Walker, A. G. et al., J. Immunol. Meth. 104:281-283 (1987).

The present invention is also directed to a kit or reagent system useful for practicing the methods described herein. Such a kit will contain a reagent combination comprising the essential elements required to conduct an assay according to the disclosed methods. The reagent system is presented in a commercially packaged form, as a composition or admixture (where the compatibility of the reagents allow), in a test device configuration, or more typically as a test kit. A test kit is a packaged combination of one or more containers, devices, or the like holding the necessary reagents, and usually including written instructions for the performance of assays. The kit may include containers to hold the materials during storage, use or both. The kit of the present invention may include any configurations and compositions for performing the various assay formats described herein.

For example, a kit for determining the presence of anti-Mtb early antibodies may contain one or more early Mtb antigens, either in immobilizable form or already immobilized to a solid support, and a detectably labeled binding partner capable of recognizing the sample anti-Mtb early antibody to be detected, for example. a labeled anti-human Ig or anti-human Fab antibody. A kit for determining the presence of an early Mtb antigen may contain an immobilizable or immobilized "capture" antibody which reacts with one epitope of an early Mtb antigen, and a detectably labeled second ("detection") antibody which reacts with a different epitope of the Mtb antigen than that recognized by the (capture) antibody. Any conventional tag or detectable label may be part of the kit, such as a radioisotope, an enzyme, a chromophore or a fluorophore. The kit may also contain a reagent capable of precipitating immune complexes.

A kit according to the present invention can additionally include ancillary chemicals such as the buffers and components of the solution in which binding of antigen and antibody takes place.

The present invention permits isolation of an Mtb early antigen which is then used to produce one or more epitope-specific mAbs, preferably in mice. Screening of these putative early Mtb-specific mAbs is done using known patient sera which have been characterized for their reactivity with the early antigen of interest. The murine mAbs produced in this way are then employed in a highly sensitive epitope-specific competition immunoassay for early detection of TB. Thus, a patient sample is tested for the presence of antibody specific for an early epitope of Mtb by its ability to compete with a known mAb for binding to a purified early antigen. For such an assay, the mycobacterial preparation may be less than pure because, under the competitive assay conditions, the mAb provides the requisite specificity for detection of patient antibodies to the epitope of choice (for which the mAb is specific).

In addition to the detection of early Mtb antigens or early antibodies, the present invention provides a method to detect immune complexes containing early Mtb antigens in a subject using an EIA as described above. Circulating immune complexes have been suggested to be of diagnostic value in TB. (See, for example, Mehta, P. K. et al, 1989, *Med. Microbiol. Immunol.* 178:229-233; Radhakrishnan, V. V. et al., 1992, *J. Med. Microbiol.* 36:128-131). Methods for detection of immune complexes are well-known in the art. Complexes may be dissociated under acid conditions and the resultant antigens and antibodies detected by immunoassay. See, for example, Bollinger, R. C. et al, 1992, *J. Infec. Dis.* 165:913-916. Immune complexes may be precipitated for direct analysis or for dissociation using known methods such as polyethylene glycol precipitation.

Purified Mtb early antigens as described herein are preferably produced using recombinant methods. See Examples. Conventional bacterial expression systems utilize Gram negative bacteria such as *E. coli* or *Salmonella* species. However, it is believed that such systems are not ideally suited for production of Mtb antigens (Burlein, J. E., In: *Tuberculosis: Pathogenesis, Protection and Control*, B. Bloom, ed., Amer. Soc. Microbiol., Washington, D.C., 1994, pp. 239-252). Rather, it is preferred to utilize homologous mycobacterial hosts for recombinant production of early Mtb antigenic proteins or glycoproteins. Methods for such manipulation and gene expression are provided in Burlein, supra. Expression in mycobacterial hosts, in particular *M. bovis* (strain BCG) or *M. smegmatis* are well-known in the art. Two examples, one of mycobacterial genes (Rouse, D. A. et al., 1996, *Mol. Microbiol.* 22:583-592) and the other of non mycobacterial genes, such as HIV-1 genes (Winter, N. et al., 1992, *Vaccines* 92, Cold Spring Harbor Press, pp. 373-378) expressed in mycobacterial hosts are cited herein as an example of the state of the art. The foregoing three references are hereby incorporated by reference in their entirety.

Urine-Based Antibody Assay

The present invention also provides a urine based diagnostic method for TB that can be used either as a stand-alone test, or as an adjunct to the serodiagnostic methods described herein. Such a method enables the practitioner to (1) determine the presence of anti-mycobacterial antibodies in urine from TB patients with early disease (non-cavitary, smear negative TB patients) and from HIV-infected TB patients; (2) determine the profile of specific mycobacterial antigens, such as those in the culture filtrate, that are consistently and strongly reactive with the urine antibodies; and (3) obtain the antigens that are recognized by the urine antibodies.

Smear positive (=late) cases constitute only about 50% of the TB cases, and patients with relatively early disease are generally defined as being smear negative. Moreover, as the HIV-epidemic spreads in developing countries, the numbers and proportions of HIV-infected TB patients increases.

Serum and urine samples from non-cavitary and/or smear negative, culture positive TB patients and from HIV-infected TB patients are obtained Cohorts comprising PPD-positive and PPD-negative healthy individuals, non-tuberculous HIV-infected individuals, or close contacts of TB patients can serve as negative controls.

The reactivity of the serum samples with culture filtrate proteins of Mtb, and the purified antigens (as described herein) is preferably determined by ELISA as described herein. All sera are preferably depleted of cross-reactive antibodies prior to use in ELISA.

The following description is of a preferred assay method and approach, and is not intended to be limiting to the particular steps (or their sequence), conditions, reagents and amounts of materials.

Briefly, 200 µl of E. coli lysates (suspended at 500 µg/ml) are coated onto wells of ELISA plates (Immulon 2, Dynex, Chantilly, Va.) and the wells are blocked with 5% bovine serum albumin (BSA). The serum samples (diluted 1:10 in PBS-Tween-20) are exposed to 8 cycles of absorption against the E. coli lysates. The adsorbed sera are then used in the ELISA assays.

Fifty µl of the individual antigens, suspended at 2 µg/ml in coating buffer (except for the total culture filtrate proteins which is used at 5 µg/ml), are allowed to bind overnight to wells of ELISA plates. After 3 washes with PBS (phosphate buffered saline), the wells are blocked with 7.5% FBS (fetal bovine serum, Hyclone, Logan, Utah) and 2.5% BSA in PBS for 2.5 hr at 37° C. Fifty µl of each serum sample are added per well at predetermined optimal dilutions (e.g., dilutions of about 1:50-1:200). The antigen-antibody binding is allowed to proceed for 90 min at 37° C. The plates are washed 6 times with PBS-Tween 20 (0.05%) and 50 µl/well of alkaline phosphatase-conjugated goat anti-human IgG (Zymed, Calif.), diluted 1:2000 in PBS/Tween 20 is added. After 60 min the plates are washed 6 times with Tris buffered saline (50 mM Tris, 150 mM NaCl) and the Gibco BRL Amplification System (Life Technologies, Gaithersburg, Md.) used for development of color. The absorbance is read at 490 nm after stopping the reaction with 50 µl of 0.3M $H_2SO_4$. The cutoff in all ELISA assays is determined by using mean absorbance (=Optical Density O.D.) +3 standard deviations (SD) of the negative control group comprising PPD positive and PPD negative healthy individuals.

The reactivity of the urine samples with the various antigens is determined initially with undiluted urine samples as described above. For the urine ELISA, results obtained by the present inventors showed that the optimal concentration of the culture filtrate protein preparation is about 125 µl/well of 4 µg/ml suspension, and for certain proteins, 125 µl/well of about 2 µg/ml. Also, the urine is left overnight in the antigen coated wells. However, if urine antibody titers of smear-negative and HIV-infected patients are lower than those observed in smear positive patients, it may be necessary to first concentrate the urine samples. For concentration, Amicon concentrators with a molecular weight cut off of 30 kDa is preferred. Concentrated urine samples are evaluated for the presence of antibodies to the above mentioned antigens. Optimal conditions for these assays are determined readily. The sensitivity and specificity of antibody detection by use of one or more of the antigens, with both urine and serum samples is also readily determined.

Vaccines

The present disclosure and Examples prove that human subjects infected with Mtb indeed do respond immunologically to early Mtb antigens, including the four surface proteins described more thoroughly herein. Thus the antigens are available to the immune system and are immunogenic. It is believed that these are stage-specific proteins that play some critical role in the microorganisms life cycle at relatively early stages of the infectious process. Hence, the vaccine compositions and methods described herein are designed to augment this immunity, and preferably, to induce it a stage wherein the bacterial infection can be prevented or curtailed.

The vaccine compositions are particularly useful in preventing Mtb infection in subjects at high risk for such an infection, as discussed above. The vaccine compositions and methods are also applicable to veterinary uses for infections with other mycobacterial species such as M. bovis which infects cattle, particularly because these proteins are conserved among mycobacterial species.

Thus, this invention includes a vaccine composition for immunizing a subject against Mtb infection. An Mtb early antigen preferably one of the proteins described herein in more detail, is prepared as the active ingredient in a vaccine composition. The vaccine may also comprises one or more of the proteins described herein, peptides thereof or functional derivatives as described, or DNA encoding the protein, and a pharmaceutically acceptable vehicle or carrier. In one embodiment, the vaccine comprises a fusion protein which includes an Mtb early antigen. The vaccine composition may further comprise an adjuvant or other immune stimulating agent. For use in vaccines, the Mtb early antigen protein or epitope-bearing peptide thereof is preferably produced recombinantly, preferably in prokaryotic cells.

Full length proteins or longer epitope-bearing fragments of the Mtb early antigen proteins are preferred immunogens, in particular, those reactive with early antibodies or T cells. If a shorter epitope-bearing fragment, for example containing 20 amino acids or less, is the active ingredient of the vaccine, it is advantageous to couple the peptide to an immunogenic carrier to enhance its immunogenicity. Such coupling techniques are well known in the art, and include standard chemical coupling techniques using linker moieties such as those available from Pierce Chemical Company, Rockford, Ill. Suitable carriers are proteins such as keyhole limpet hemocyanin (KLH), E. coli pilin protein k99, BSA, or rotavirus VP6 protein.

Another embodiment is a fusion protein which comprise the Mtb early antigen protein or epitope-bearing peptide region fused linearly to an additional amino acid sequence. Because of the ease with which recombinant materials can be manipulated, multiple copies a selected epitope-bearing region may be included in a single fusion protein molecule. Alternatively, several different epitope-bearing regions can be "mixed and matched" in a single fusion protein.

The active ingredient such, preferably a recombinant product, is preferably administered as a protein or peptide vaccine. The vaccine composition may also comprise a DNA vaccine (e.g., Hoffman, S L et al., 1995, *Ann N Y Acad Sci* 772:88-94; Donnelly, J J et al., 1997, *Annu Rev Immunol* 15:617-48; Robinson, H L, 1997, Vaccine. 15: 785-787, 1997; Wang, R et al., 1998, Science. 282: 476-480, 1998; Gurunathan, S et al., 2000, *Annu Rev Immunol* 18:927-74; Restifo, N P et al., 2000, Gene Ther. 7: 89-92). The DNA preferably encodes the protein or epitope(s), optionally linked to a protein that promotes expression of the Mtb protein in the host after immunization. Examples known in the art include heat shock protein 70 (HSP70) (Srivastava, P K et al., 1994. *Immunogenetics* 39:93-8; Suto, R et al., 1995, *Science* 269:1585-8; Arnold-Schild, D et al., 1999, *J Immunol* 162:3757-60; Binder, R J et al., 2000, *Nature Immunology* 2:151-155; Chen, C H et al., 2000, *Cancer Res* 60:1035-42) or translocation proteins such herpesvirus protein VP22 (Elliott, G, and O'Hare, P., 1997. *Cell* 88:223-33; Phelan, A et al., 1998, *Nat Biotechnol* 16:440-3; Dilber, M S et al., 1999. *Gene Ther* 6:12-21) or domain II of *Pseudomonas aeruginosa* exotoxin A (ETA) (Jinno, Y et aL, J Biol Chem. 264: 15953-15959, 1989; Siegall, C B et al., Biochemistry. 30: 7154-7159, 1991; Prior, T I et al., Biochemistry. 31: 3555-3559, 1992; Fominaya, J et al., J Biol Chem. 271: 10560-10568, 1996; Fominaya, J et al., Gene Ther. 5: 521-530, 1998; Goletz, T J et al., Hum Immunol. 54: 129-136, 1997).

In another embodiment, the vaccine is in the form of a strain of bacteria (preferably a known "vaccine strain") which has been genetically transformed to express the protein or epitope-bearing peptide. Some known vaccine strains of *Salmonella* are described below. *Salmonella dublin* live vaccine strain SL5928 aroA148 fliC(i)::Tn10 and *S. typhimurium* LB5000 hsdSB121 leu-3121 (Newton S. M. et al., *Science* 1989, 244: 70

A *Salmonella* strain expressing the Mtb protein or fragment of this invention may be constructed using known methods. Thus, a plasmid encoding the protein or peptide. The plasmid may first be selected in an appropriate host, e.g., *E. coli* strain MC1061. The purified plasmid is then introduced into *S. typhimurium* strain LB5000 so that the plasmid DNA is be properly modified for introduction into *Salmonella* vaccine strains. Plasmid DNA isolated from LB5000 is introduced into, e.g., *S. dublin* strain SL5928 by electroporation. Expression of the Mtb protein or fragment encoded by the plasmid in SL5928 can be verified by Western blots of bacterial lysates and antibodies specific for the relevant antigen or epitope.

The active ingredient, or mixture of active ingredients, in protein or peptide vaccine composition is formulated conventionally using methods well-known for formulation of such vaccines. The active ingredient is generally dissolved or suspended in an acceptable carrier such as phosphate buffered saline. Vaccine compositions may include an immunostimulant or adjuvant such as complete or incomplete Freund's adjuvant, aluminum hydroxide, liposomes, beads such as latex or gold beads, ISCOMs, and the like. For example, 0.5 ml of Freund's complete adjuvant or a synthetic adjuvant with less undesirable side effects is used for intramuscular or subcutaneous injections, preferably for all initial immunizations; this can be followed with Freund's incomplete adjuvant for booster injections. General methods to prepare vaccines are described in *Remington's Pharmaceutical Science*; Mack Publishing Company Easton, Pa. (latest edition).

Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

Adjuvants, including liposomes, are discussed in the following references, incorporated herein by reference: Gregoriades, G. et al., *Immunological Adjuvants and Vaccines*, Plenum Press, New York, 1989 Michalek, S. M. et al., "Liposomes as Oral Adjuvants," *Curr. Top. Microbiol. Immunol.* 146:51-58 (1989).

The vaccine compositions preferably contain (1) an effective amount of the active ingredient, that is, the protein or peptide together with (2) a suitable amount of a carrier molecule or, optionally a carrier vehicle, and, if desired, (3) preservatives, buffers, and the like. Descriptions of vaccine formulations are found in Voller, A. et al., *New Trends and Developments in Vaccines*, University Park Press, Baltimore, Md. (1978).

As with all immunogenic compositions for eliciting antibodies or cell-mediated immunity, the immunogenically effective amounts of the proteins or peptides or other vaccine compositions of the invention must be determined empirically. Factors to be considered include the immunogenicity of the native peptide, whether or not the peptide will be complexed with or covalently attached to an adjuvant or carrier protein or other carrier and the route of administration for the composition, i.e., intravenous, intramuscular, subcutaneous, etc., and the number of immunizing doses to be administered. Such factors are known in the vaccine art, and it is well within the skill of the immunologists to make such determinations without undue experimentation.

The vaccines are administered as is generally understood in the art. Ordinarily, systemic administration is by injection; however, other effective means of administration are known. With suitable formulation, peptide vaccines may be administered across the mucus membrane using penetrants such as bile salts or fusidic acids in combination, usually, with a surfactant. Transcutaneous administration of peptides is also known. Oral formulations can also be used. Dosage levels depend on the mode of administration, the nature of the subject, and the nature of carrier/adjuvant formulation. Preferably, an effective amount of the protein or peptide is between about 0.01 μg/kg-1 mg/kg body weight. Subjects may be immunized systemically by injection or orally by feeding, e.g., in the case of vaccine strains of bacteria, $10^8$-$10^{10}$ bacteria on one or multiple occasions. In general, multiple administrations of the vaccine in a standard immunization protocol are used, as is standard in the art. For example, the vaccines can be administered at approximately two to six week intervals, preferably monthly, for a period of from one to four inoculations in order to provide protection.

Vaccination with the vaccine composition will result in an immune response, either or both of an antibody response and a cell-mediated response, which will block one or more steps in the Mtb bacterium's infective cycle, preferably the steps of binding to and entry into host cells in which it grows.

T Cell Responses

Human (or animal model) peripheral blood lymphocytes (PBL) or lymphocytes from another source (e.g., lymph node) are incubated in complete culture medium (as are well known in the art) at appropriate cell concentrations. A preferred medium is RPMI 1640, supplemented with 10% (vol/vol) fetal bovine serum, 50 units/ml penicillin/streptomycin, 2 mM L-glutamine, 1 mM sodium pyruvate, 2 mM nonessential amino acids)

Cells are stimulated for an appropriate period, e.g., 2-4 days with an Mtb protein or peptide fragment thereof antigen at concentrations readily ascertainable by those of skill in the art. Interleukin 2 (IL-2) can be added to promote expansion of antigen-specific cells if it is desired to generate antigen-specific lines or clones.

T cells from a PPD+ normal individual or from a patient being tested are cultured with varying concentrations of an Mtb protein or peptide being evaluated for its T cell stimulatory capacity. T cell reactivity is measured in any of a number of conventional assays, for example T cell proliferation which can be measured by radiolabeled thymidine or iododeoxyuridine, or by colorimetric assay of cell number. Alternatively, stimulation of T cell activity can be measured by secretion of cytokines or by ELISPOT assays that enumerate cytokine secreting cells.

The enzyme-linked immunospot (ELISPOT) assay described (e.g. Miyahira, Y et al., J Immunol Methods. 181: 45-54, 1995) utilizes 96-well filtration plates (Millipore, Bedford, Mass.) coated with about 10 µg/ml of an antibody (commercially available) specific for a cytokine being assayed in 50 µl PBS. After overnight incubation at 4° C., the wells are washed and blocked with culture medium containing 10% fetal bovine serum. Different concentrations of fresh isolated lymphocytes being assayed starting from $1 \times 10^6$/well, are added to the well along with 15 international units/ml interleukin-2 (IL-2). Cells are incubated at 37° C. for 24 hours either with or without a stimulatory amount of the Mtb protein or peptide thereof. After culture, the plate is washed and then followed by incubation with 5 µg/ml biotinylated antibody specific for the cytokine being assayed (e.g., IFN-γ) in 50 µl in PBS at 4° C. overnight. After washing six times, 1.25 µg/ml avidin-alkaline phosphatase (Sigma, St. Louis, Mo.) in 50 µl PBS are added and incubated for 2 hours at room temperature. After washing, spots are developed by adding 50 µl BCIP/NBT solution (Boehringer Mannheim, Indianapolis, Ind.) and incubated at room temperature for 1 hr. The spots are counted using a dissecting microscope.

Intracytoplasmic Cytokine Staining and Flow Cytometry Analysis

Lymphocytes are incubated either with the Mtb protein or peptide at an appropriate concentration for about 20 hours. Golgistop (Pharmingen, San Diego, Calif.) is added 6 hours before harvesting the cells from the culture. Cells are then washed once in an appropriate buffer for flow cytometry and stained with appropriately labeled (e.g., phycoerythrin-conjugated) anti CD8 or anti-CD4 antibody. Cells are subjected to intracellular cytokine staining using the Cytofix/Cytoperm kit according to the manufacturer's instructions (e.g., from Pharmingen). FITC-conjugated anti-cytokine antibodies and the immunoglobulin isotype control antibody are used. Analysis was done on a flow cytometer ELISA for Cytokines Lymphocytes (e.g., $4 \times 10^6$) are obtained from subjects or from culture and are incubated in culture medium with Mtb protein or peptide in a total volume of 2 ml of medium in a 24-well tissue culture plate for 72 hours. The supernatants are harvested and assayed for the presence of cytokine, e.g., IFN-γ or IL12 or IL18 using commercial ELISA kits according to manufacturer's protocol.

Antibody Responses to Mt

The humoral responses to Mtb in TB patients have been the subject of investigation for several decades, primarily for the purpose of devising serodiagnosis for TB (reviewed in Grange, J M, 1984, Adv Tuberc Res. 21:1-78). The earlier studies of humoral responses in TB patients were mostly based on use of crude mixtures of antigens like PPD, bacterial sonicates, Ag A60 etc. These antigen preparations provided unsatisfactory results, because although a majority of TB patients were antibody positive, often-healthy individuals also had antibodies that showed cross-reactivity with these preparations. A variety of approaches, both biochemical and recombinant, were then used by different labs to obtain individual, purified antigens of Mtb (Young, D B et al., Mol. Microbiol. 6:133-145). Studies of purified antigens showed that many of the Mtb antigens are conserved, prokaryotic proteins which have significant homology with analogous proteins in other mycobacterial and non-mycobacterial organisms (the 65 kDa GroEL, 70 kDa DNA K, 47 kDa elongation factor Tu, 44 kDa Pst A homolog, 40 kDa L-alanine dehydrogenase, 23 kDa superoxide dismutase, 23 kDa outer membrane protein, 14 kDa GroES, enzymes of metabolic pathways etc (Young et al., supra). Studies also showed that healthy individuals often have antibodies to epitopes on conserved regions of such ubiquitous prokaryotic proteins, resulting in the observed cross-reactivity of the healthy sera with mycobacterial antigens. Some of the purified mycobacterial antigens were evaluated for their use in serodiagnosis of TB, and one of them, a 38-kDa protein provided promising results. This antigen provided very high specificity (>98%). However, extensive studies with the 38 kDa protein in different populations showed that anti-38 kDa antibodies are present only in individuals with chronic, recurrent, cavitary TB, limiting its utility in diagnosis of TB (Bothamley, G H et al., 1992, Thorax. 47:270-275; Daniels, T M, 1996, p. 223-231. In W. R. Rom and S. Garay (ed.), In: *Tuberculosis*. Little, Brown and Company, Inc, Boston, Mass.).

Most of the purified antigens that were evaluated for their utility for serodiagnosis were either proteins that were immunodominant in mice that were immunized with killed preparations/sonicates of Mtb or BCG for the purpose of producing monoclonal antibodies (Engers, H D et al., 1986, Infect. Immun. 51:718-720), or were antigens that were relatively easy to purify by biochemical procedures (Sada, E et al., 1990, J. Clin Microbiol. 28:2587-2590; Sada, E et al., 1990, J. Infec. Dis. 162:928-931). Based on the rationale that there may be differences in antigens expressed by in vivo replicating bacteria, and inactivated antigen preparations, our approach was to perform a direct analysis of antibody responses in patients with active TB.

We developed a unique approach to address the issue of cross-reactivity described above, and have provided evidence that adsorption of sera with lysates of *E. coli*, which contain many of the ubiquitous prokaryotic proteins, results in significant depletion of the cross-reactive antibodies. Using cross-reactive antibody depleted sera, we have systematically dissected the antibody responses of both HIV-infected and non-HIV TB patients at different stages of disease progression. Our studies show that the culture filtrate antigens are targets of humoral responses during active infection in humans, and that antibodies to the culture filtrate proteins are present in individuals with active TB, and not in PPD positive healthy individuals. We have defined the repertoire of antigens in culture filtrates of Mtb that elicit antibodies in TB patients by using 2-D fractionated proteins and immunoblotting. Our studies show that of the >100 different proteins released by extracellularly growing Mtb, antibodies to only a small number of proteins (18 antigens) are present in non-HIV TB patients with non-cavitary disease. HIV-infected TB patients, a majority of whom also has non-cavitary disease, have antibodies to the same small subset of culture filtrate antigens. In contrast, a majority of the advanced cavitary TB patients have antibodies to the above 18 antigens, and several additional antigens. These studies make several important points.

First, the reactivity of TB sera with the culture filtrate proteins, and the lack of reactivity of sera from PPD positive healthy individuals with the same antigens suggest that antibodies to these antigens are associated with active TB infection.

Second, the sera from TB patients with only a minority of the culture filtrate proteins of Mtb suggests that many of the culture filtrate proteins may not be expressed in significant amounts by the in vivo replicating bacteria.

Third, the differences in the antigen profiles recognized by the non-cavitary and cavitary TB patients suggests that the local milieu (intracellular vs. extracellular, extent of liquification, cavitation, etc.) in which the in vivo bacteria exist affects the antigen profiles expressed. We also showed that 3 of these 26 culture filtrate proteins, identified on the basis of their reactivity with TB sera, are useful for serodiagnosis for pulmonary TB.

Although the culture filtrates have yielded important molecules for diagnosis of TB, they would only contain antigens that are expressed by Mtb replicating in vitro in bacteriological media. Other antigens that are expressed by the bacteria during in vivo growth may be poorly expressed or even absent in these preparations. Recently at least 3 antigens of Mtb that are expressed/upregulated in intracellular conditions, or in vivo, or in granulomas have been reported. In fact, the ability of bacteria to respond to environmental changes is a key feature in their ability to survive, and differential expression of proteins in vivo and in vitro, and of different proteins during different stages of disease progression has been reported for several pathogens. The importance of the effect of the immune system components on bacterial survival and growth is also emphasized by the opportunistic pathogens that cause disease only in individuals with compromised immune systems. A multitude of factors—cytokine levels, iron availability, pH, osmolarity etc can affect the gene expression, and therefore the gene products, expressed by the bacteria in vivo. The search for molecules that may be useful for early diagnosis of TB should ideally be focused on antigens expressed by the in vivo bacteria during the earliest stages of infection. Yet, most current studies have focused either on antigens expressed by the bacteria growing in vitro in bacteriological media or on antigens recognized by sera of patients with clinical disease.

Recent experiments with increasing doses of BCG as a vaccine in mice showed that regardless of the route of immunization, high doses of BCG activated Th2 responses (Power, C A et al., 1998, Infect. Immun. 66:5743-5750). Other studies in which humoral, cellular and protective immune responses were monitored in individual animals immunized with DNA vaccines encoding several different Mtb antigens have shown that antibody concentrations reflected the levels of antigenic expression (Li, Z et al., 1999, Infect. Immun. 67:4780-4786). These studies suggested that the presence of antibodies to any protein can serve as an excellent marker of expression of high levels of that protein in vivo. Since the exact in vivo environment is impossible to replicate in vitro or in culture, the studies described herein are based on using antibodies as tools to identify antigens that are expressed by Mtb in vivo during the early stages of disease progression. Other investigators (Amara, R R et al., 1996, Infect. Immun. 64:3765-3771) used antibodies from TB patients to identify antigens of Mtb expressed in vivo and have identified several novel antigens. However, these antigens are those that were recognized by sera from patients with chronic, culture-positive TB, and represent antigens expressed in an environment where there is marked caseous necrosis, liquification of caseous material and cavity formation—an environment that allows extensive extracellular replication of the in vivo bacteria. In contrast, prior to the development of extensive pulmonary lesions, the bacteria are believed to be primarily intracellular, an environment that is different from the cavity environment.

Whether the same antigens are expressed by the in vivo Mtb during the early and the late stages of active disease is not known. Our own studies with non-cavitary and cavitary TB patients have shown that cavitary patients have antibodies to several antigens that are not recognized in non-cavitary patients, suggesting that the antigen profile expressed in vivo is altered with disease progression as the environment in which the bacteria survive changes. Thus, sera from advanced TB patients are likely to be enriched for antibodies to antigens expressed by the bacteria replicating extracellularly in cavitary lesions. The present invention focuses on identifying and obtaining antigens of Mtb that are expressed in vivo, and elicit immune responses during the early, pre-clinical stages of an active infection with Mtb. Sera from patients with active, early TB cannot be obtained from humans because the lifetime risk of a latently infected individual (PPD positive) developing active clinical TB is so small that the size of the cohort of PPD positive individuals that would have to be studied for their lifetimes, to identify some individuals who may develop disease is not possible at the practical level. Yet, the antigens expressed during the early stages of disease may play an important role in determining the outcome of infection and may prove useful in serodiagnostic assays for diagnosis of early, active infection with Mtb.

To identify the antigens expressed by in vivo replicating Mtb during the early stages of disease progression, studies were done with antibodies from guinea pigs infected by virulent airborne organisms. The guinea pig model is considered especially relevant to humans, clinically, immunologically and pathologically (Smith, D W et al., 1989. Reviews of Infect. Dis. 2:s385-s393). In contrast to the mouse and rat, but like the humans, guinea pigs are susceptible to low doses of airborne Mtb, have a strong cutaneous DTH to tuberculin, and display langans giant cells and caseation in pulmonary lesions. Earlier studies of the course of infection in guinea pigs following low dose, pulmonary infection with Mtb have revealed that the mycobacteria replicate exponentially in the lungs during the first 3-21 days post-infection in the lungs (Smith, D W et al., 1970, Am Rev. Respir Dis 102:937-949). Dissemination via the lymphatics to the lymph nodes draining the lung fields occurs at about 8-10 days post-infection, with organisms reaching the spleen via the bloodstream between 14 and 20 days. Within 4 weeks following initiation of the pulmonary infection, there is seeding of mycobacteria into so-called secondary foci throughout the lungs via hematogenous dissemination. Clinical signs of TB in these guinea pigs, such as weight loss and respiratory distress, usually occur at 8-10 weeks post-infection, with mortality observed at 14-18 weeks (Wiegeshaus, E H et al., 1970, Am. Rev. Respir. Dis. 102:422-429). For studies of antigens that are expressed during the early stages of bacterial replication and dissemination by in vivo growing bacteria, serum samples were obtained from guinea pigs infected with airborne virulent Mtb. These sera, obtained at 1, 3, 4, 5 and 6 weeks post infection were provided by Dr. David McMurray, Texas A & M University. One serum sample, obtained from a guinea pig 8 weeks post infection was obtained from Dr. John Belisle, Colorado State University. Thus, the period of time during which the sera used in this study were collected reflects the early post-infection period during which rapid bacillary multiplication and dissemination is known to occur in the lung and elsewhere. These sera would contain antibodies directed against antigens expressed by the bacteria replicating and disseminating in vivo and were therefore used to screen a λgt11 expression library of Mtb to obtain the clones expressing these antigens (Young, R A et al., 1985, Proc. Natl. Acad. Sci. USA. 82:2583-2587). These are the proteins expressed during the early stages of disease progression by in vivo growing bacteria. Our initial studies showed that these antigens were also recognized during infection with Mtb in humans. These antigens, therefore, are useful as diagnostic reagents The following examples are directed to the discovery of four novel repetitive proteins that are immunodominant as Mtb antigens during early tuberculosis To identify antigens of Mtb expressed during early TB, rabbits were infected by aerosols of Mtb H37Rv or a clinical isolate CDC1551, and bled 5 weeks post-infection. These sera were used to immunoscreen a λgt11 genomic DNA expression library of Mtb. Seven positive clones were obtained, five of which were sequenced. Clones AD1 and AD2 express overlapping portions of C-terminal of the protein PirG (Rv 3810). The product of the PirG has previously been shown to be a cell surface exposed protein associated with virulence of Mtb (Berthet, F.-X. et al., 1998, Science. 282:759-762). Clones AD9, AD10 and AD16 express the C-terminal portion of a PE_PGRS (Rv3367) glycine rich protein; a proline and threonine rich protein PTRP (Rv 0538) and the protein MtrA (Rv 3246c) respectively. Three of the proteins, PirG, PE_PGRS and PTRP are repetitive proteins, and have multiple tandem repeats of unique amino acid motifs while the fourth protein, MtrA is a response regulator of a putative two component signal transduction system mtrA-mtrB of Mtb, which has been shown to be upregulated on intracellular entry and residence of Mtb in macrophages (44). All four antigens were recognized by pooled sera from cavitary TB patients confirming their in vivo expression in human TB. Three of the antigens, (PE_PGRS, PTRP and MtrA) were also reactive with sera from non-cavitary TB and HIV pre-TB individuals suggesting that these proteins are expressed in vivo early during an active infection.

Studies performed by the present inventors' laboratory identifying the antigens in culture filtrates of Mtb recognized by antibodies from non-cavitary and/or cavitary TB patients are published (described supra). Studies with sera from the aerosol-infected guinea pigs are presented below in Examples I-V. A list of references following Examples I-V contains the references cited by parenthetical number in these Examples.

Subsequent Examples VI-XIII are directed to the discovery of four novel repetitive proteins that are immunodominant as Mtb antigens during early tuberculosis To identify antigens of Mtb expressed during early TB, rabbits were infected by aerosols of Mtb H37Rv or a clinical isolate CDC1551, and bled 5 weeks post-infection. These sera were used to immunoscreen a λgt11 genomic DNA expression library of Mtb. Seven positive clones were obtained, five of which were sequenced. Clones AD1 and AD2 express overlapping portions of C-terminal of the protein PirG (Rv 3810). The product of the PirG has previously been shown to be a cell surface exposed protein associated with virulence of Mtb (Berthet, F.-X. et al., 1998, Science. 282:759-762). Clones AD9, AD10 and AD16 express the C-terminal portion of a PE_PGRS (Rv3367) glycine rich protein; a proline and threonine rich protein PTRP (Rv 0538) and the protein MtrA (Rv 3246c) respectively. Three of the proteins, PirG, PE_PGRS and PTRP are repetitive proteins, and have multiple tandem repeats of unique amino acid motifs while the fourth protein, MtrA is a response regulator of a putative two component signal transduction system mtrA-mtrB of Mtb, which has been shown to be upregulated on intracellular entry and residence of Mtb in macrophages (Via, L et al., 1996, J. Bacteriology. 178:3314-21). All four antigens were recognized by pooled sera from cavitary TB patients confirming their in vivo expression in human TB. Three of the antigens, (PE_PGRS, PTRP and MtrA) were also reactive with sera from non-cavitary TB and HIV pre-TB individuals suggesting that these proteins are expressed in vivo early during an active infection.

Example I

Examination of Sera of Infected Guinea Pigs

Serum samples: Sera obtained from 2 uninfected guinea pigs and 20 guinea pigs infected with 4-10 cfu, airborne, virulent Mtb H37Rv, and bled at 1,3,4,5, and 6 weeks post-infection, were provided by Dr. David McMurray. Serum from one guinea pig infected for 8 weeks was obtained from Dr. John Belisle. A serum pool containing one serum each from guinea pigs bled 1, 3-6 weeks post-infection and 8 weeks post infection sample was absorbed against an E. coli lysate and used at a dilution of 1:100 for probing the western blots (described below) and for immunoscreening the expression library.

Reactivity of guinea-pig serum pool with antigens of Mtb: The reactivity of the above serum pool was assessed with the following antigen preparations of Mtb (provided by Dr. John Belisle, Colorado State University) by western blot analyses:

a) Bacterial cell sonicate (CS): the cell pellet of organisms harvested by centrifugation, sonicated extensively, and subjected to high speed centrifugation to get rid of the cell-wall fragments. This preparation contains primarily cytoplasmic proteins of Mtb.

b) SDS-soluble cell-wall proteins (SDS-CW): the proteins associated with the bacterial cell wall, extracted as described in (Laal, S et al., 1997, J. Infect. Dis. 176:133-143).

c) Lipoarabinomannan-free culture filtrate proteins (LAM-free CFP) from log phase Mtb: This preparation contains the proteins secreted by bacteria replicating in vitro (in bacteriological media) (Sonnenberg, M G et al., 1997, Infect. Immun. 65:4515-4524).

The preparation of these antigens has been described before (Laal et al., supra). Western blots prepared after SDS-PA gel fractionation of these antigens were probed with the guinea-pig serum pool at a dilution of 1:100. The filters were washed, exposed to 1:1000 dilution of alkaline phosphatase conjugated anti-guinea-pig IgG, washed and developed with BCIP-NBT substrate.

Figure 1:
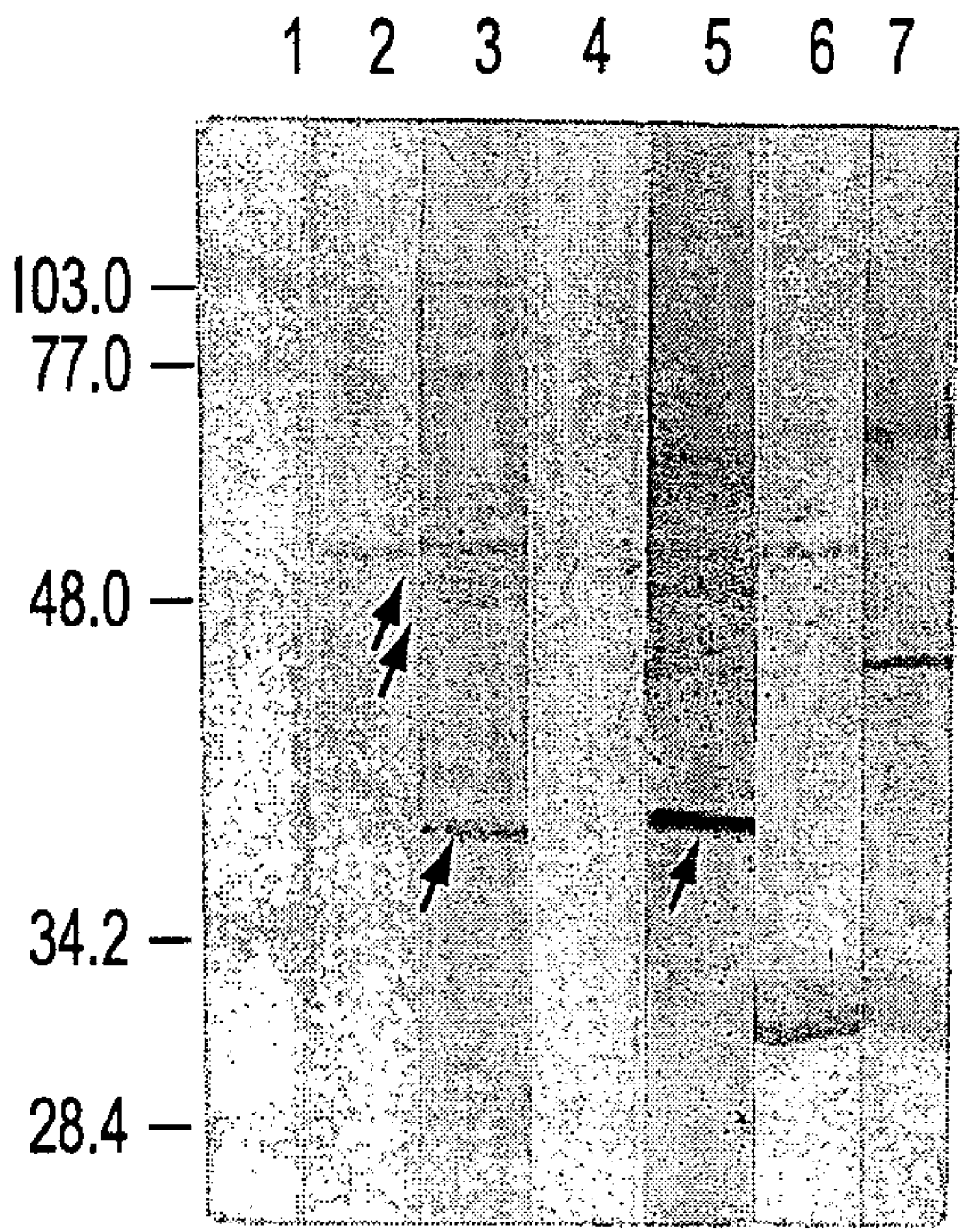
Figure 2C:
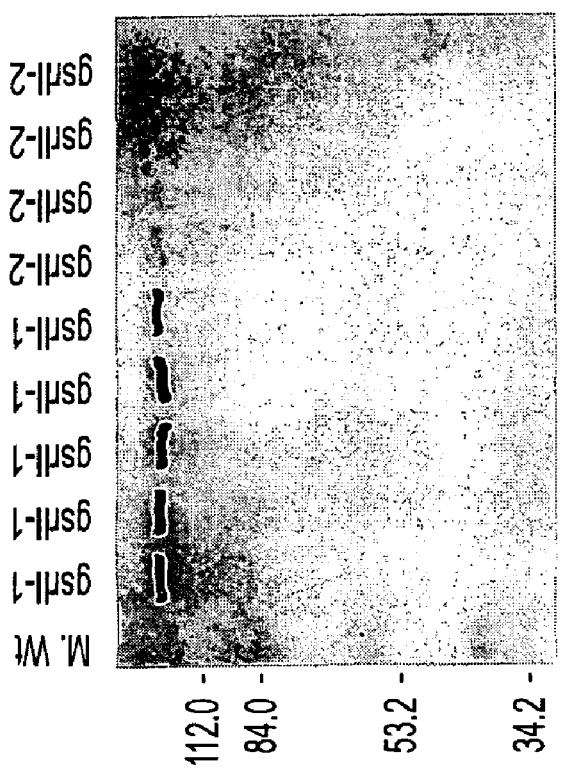
Figure 2D:
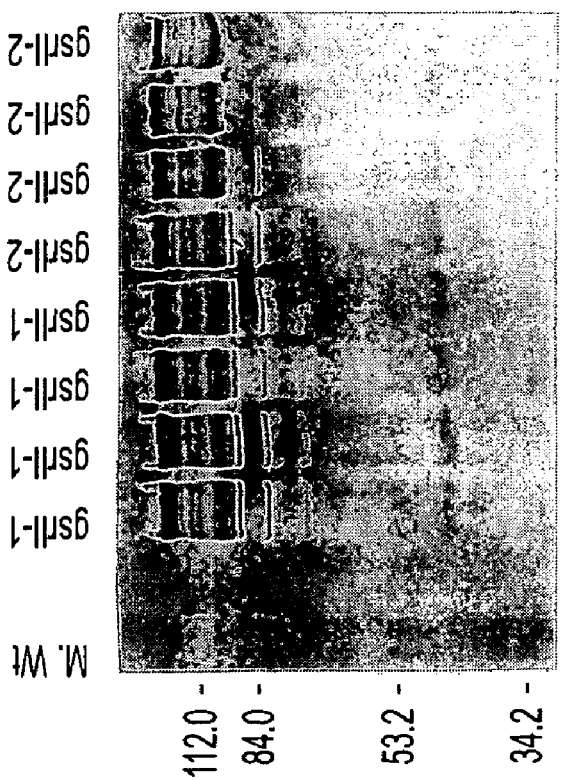

Only the serum pool from Mtb infected guinea pigs reacted strongly with a ~40 kDa protein present in the total CS of Mtb (FIG. 1, lane 3). Weaker reactivity was also seen with a doublet at ~50-52 kDa (lane 3). Several other proteins reacted strongly with the infected guinea pig serum pool (lane 3) and weakly with the uninfected guinea pig serum pool (lane 2). A ~40 kDa protein was also identified only by the serum pool from infected animals in the SDS-CW preparation, as were several weakly reactive bands ranging from 48-103 kDa (lane 5). None of the antigens in the LAM-free CFP preparation showed any specific reactivity with the serum pool from the infected animals.

Screening of the Mtb λgt11 expression library with guinea pig sera: To obtain the antigens recognized by the sera from the aerosol infected guinea-pigs, the above serum pool was used to screen a λgt11 expression library of Mtb DNA (World Health Organization) (Young, R A et al., 1985, Proc. Natl. Acad. Sci. USA. 82:2583-2587). The details of the library and the methods for screening are described in the Experimental Design section. Several recombinant phages, 10 of which could be cloned by several rounds of screening, were obtained. These are referred to as gsr I-3, and I-6, which were obtained during preliminary screening, and gsr II-1, II-2, II-3, II-4, II-6, II-14, II-15 and II-20 which were obtained during the second round of screening.

Characterization of the recombinant proteins: Lysogens of the gsr-clones were established in E. coli Y1089. Single colonies from lysogens were used to obtain the recombinant proteins (35). The E. coli lysates containing the recombinant proteins were fractionated on 10% SDS-PA gels and electroblotted onto nitrocellulose membranes. Lysates from several individual colonies from each of the lysogens were tested. The blots were probed with the guinea-pig serum pool and separate blots were also probed with a commercially available murine mAb against β-galactosidase. Lysates from E. coli Y1089 alone were used as controls. FIGS. 2a-d and 3a show the results of these experiments. β-gal-fusion proteins were present in the lysates of lysogens from all the 10 recombinant phages obtained from the library.

Figures 2, 3A:
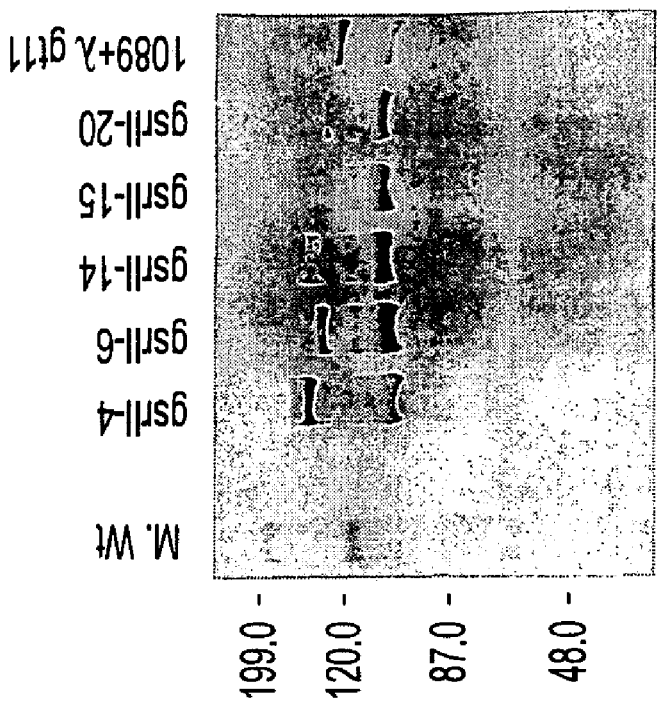
FIG. 3a shows Western blots of fusion proteins with antibodies to β-galactosidase (see description below figure)
Figures 1, 3A:
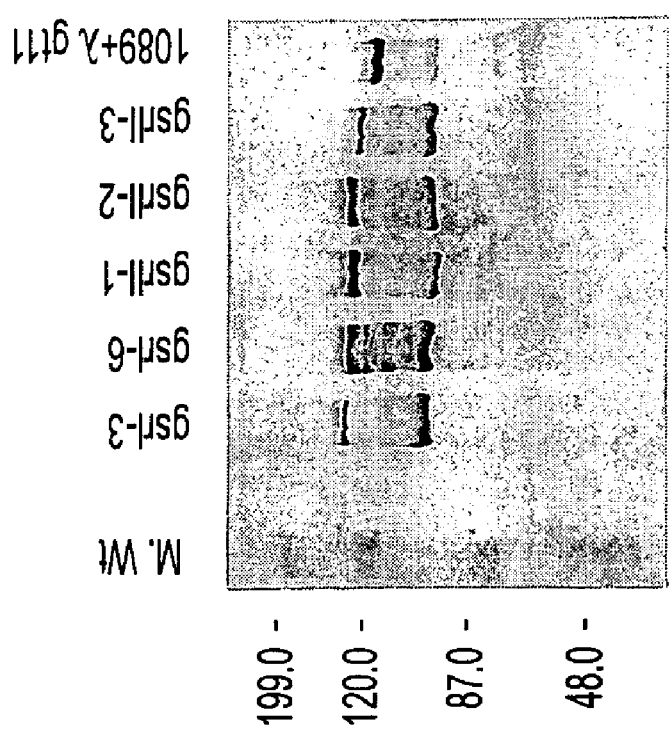
Figures 2, 3B:
FIG. 3b shows reactivity of sera from Mtb-infected guinea pigs and ant-β-gal antibody with fractionated lysates (see description below figure).
Figures 1, 3B:
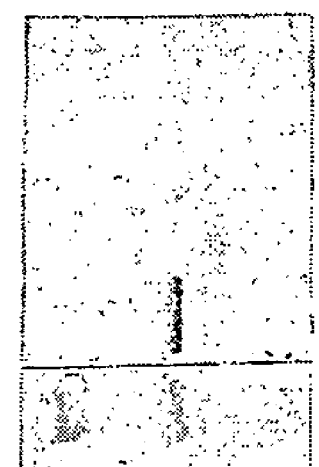

Further studies were performed to confirm that the reactivity of the sera from the infected animals with the fusion proteins was with the mycobacterial fragment, and not the β-galactosidase portion of the fusion protein (FIG. 3b). E coli Y 1089 was lysogenized with the empty λgt11 vector, induced to express the β-galactosidase, and the blots probed with the anti-β-gal antibody, or the guinea-pig serum pool. Only the former antibody showed significant reactivity with the β-galactosidase band in the induced lysate (FIG. 3b).

Cross hybridization between the 10 clones: DNA from 9/10 gsr clones was isolated by the commercial Wizard L Preps DNA Purification system (Promega), and digested with EcoR1 to determine the insert size. To determine if some of the gsr clones were related to the others, the insert DNA from 9/10 clones was isolated, and labeled with $^{32}P$ by a random priming DNA labeling. The DNA from all the gsr clones (except gsr II-14 and II-20) was digested with EcoR1, transferred from the agarose gels to a Nytran Plus filters (Schleicher & Schuell, Keene, N.H.) and the filters subjected to Southern blot analysis using the labeled insert DNA from the gsr clones. The hybridization pattern revealed that insert DNA from clones gsr I-3, II-3 and II-6 cross hybridized, while inserts of gsr I-6, II-1, II-2, II-4 and II-15 hybridized only with the parent clone. The status of clones gsr II-14 and gsr II-20 remains to be determined. Thus, at least six of the eight clones are independent clones. Clones gsr I-6, gsr II-1 and gsr II-2 were randomly selected for initial studies.

DNA Sequence Analyses: λDNA from clones gsr I-6, II-1 and II-2 was digested with EcoR1 and the insert subcloned into vector pGEMEX-1 (Promega) whose reading frame at the EcoR1 cloning site is identical to λgt11. Competent E. coli JM 109 cells were transformed with the recombinant plasmid (pGEMEX plus insert from gsr clones). Plasmid DNA was isolated using Wizard Plus Minipreps (Promega), and used for automated sequencing with SP6 and T3 promoter specific primers flanking the multiple cloning site in the pGEMEX-1 followed by primer walking. The sequencing was performed by the NYU Medical Center core sequencing facility. The nucleotide sequences obtained were used in homology searches using the NCBI BLAST search (1). Nucleotide sequences for all 3 clones shared homology to known Mtb sequences.

Figure 4A:
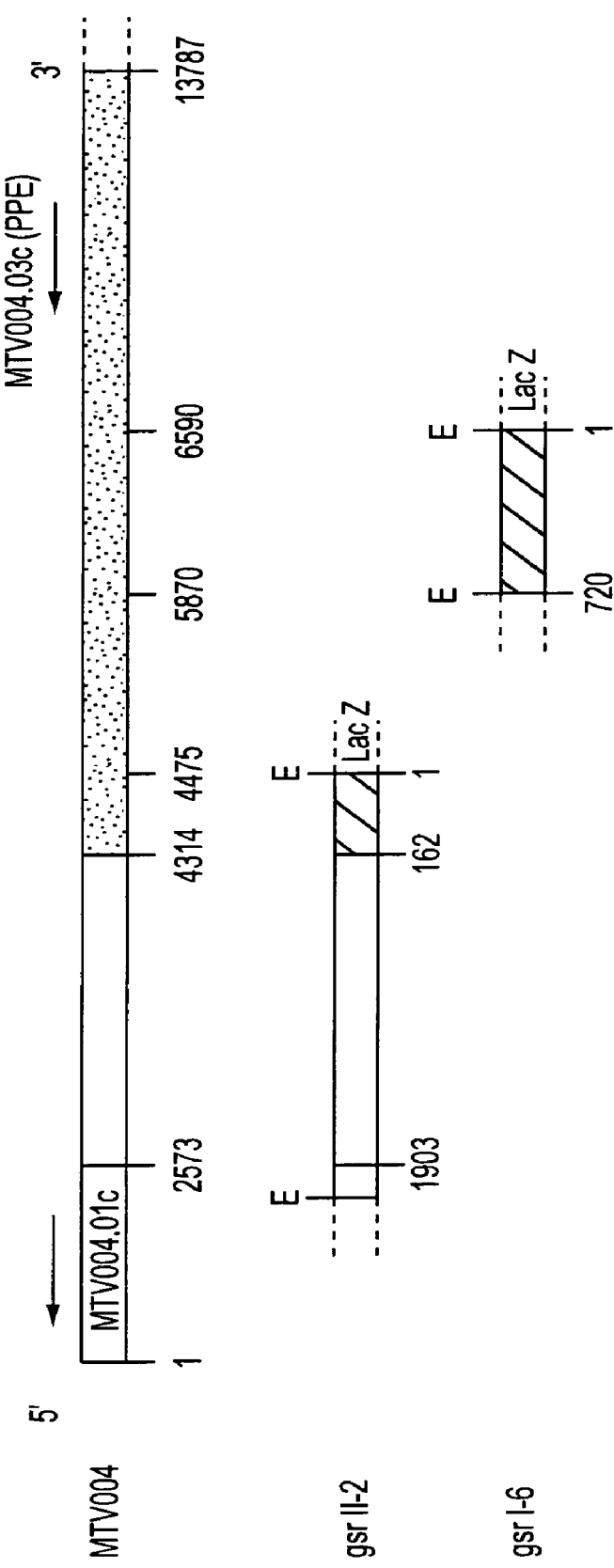
FIG. 4a shows sequence alignment of clones gsr II-2 and I-6 with cosmid MTV004.

DNA sequence analyses of clones gsr I-6 (0.7 kb) and gsr II-2 (2.1 kb) showed 98% and 99% homology respectively to different regions of the same gene (Mtb cosmid MTV004.03c: nu 4314-13787, FIG. 4a). Clone gsr I-6 (nu 1-720) and gsr II-2 (nu 1-1903) showed homology to nu 5870-6590 and nu 2573-4476 of MTV004 respectively. A DNA fragment (152 bp) at the 3' end of gsr II-2 showed only 60% homology to MTV004 (and several other regions on the mycobacterial genome) indicating that scrambling might have occurred during construction of the library. The gene product of MTV004.03 is a 3175 aa (309 kDa) member of the recently described PPE family of Gly-, Ala-, Asn-rich proteins (FIG. 4b). The peptides expressed in gsr I-6 and gsr II-2 represent aa 2400-2639 and 3104-3157 respectively in the C-terminal half of the MTV004.03 gene product (FIG. 4b).

The PPE family of acidic proteins was described recently when the genome sequence of Mtb was analyzed (5). This family of proteins has 68 members, all of who possess a conserved N-terminal domain of 180 aa, and a ProProGlu (PPE) motif at positions 7,8 and 9. Based on the characteristics of the C-terminal portion, the PPE proteins fall into 3 groups, one of which (MPTR family) is characterized by the presence of multiple copies of the AsnXGlyXGlyXAsnXGly motif (5). Analyses of the protein encoded by MTV004.03 by FINDPATTERN revealed the presence of 65 tandem copies of this motif spanning the entire length of the protein in 5 clusters. The motif is repeated 6 times in the region encoded by clone gsr I-6. The sequence of gsr II-2 did not contain this motif (FIG. 4b).

Clone gsr II-1 (2.14 kb) nucleotide sequence showed homology to Mtb cosmid Y336 (A# Z95586) region 22232-24371. Nucleotides 1-819 (273 aa) of gsr II-1 showed 96% homology to nu 22232-23050 (ORF MTCY336.28) of MTCY336 (FIG. 5a). This clone also showed homology to the RD3 region of M. bovis (24) which is represented by sequences with accession numbers U35017 (MBDR3S1) and U35018 (MBDR3S2). Nucleotides 1-819 of gsr II-1 showed 99% homology to nu 8370-9189 (ORF 3H) of MBDR3S1. The orientation of the sequence was established by restriction analysis. The gene product of MTCY336.28 is a 50 kDa protein with unknown function (FIG. 5b). The RD3 region has been described to be present in Mtb Erdman and M. bovis, but absent from BCG and BCG substrains Connaught, Pasteur and Brazil.

Reactivity of the fusion proteins with sera from guinea-pigs with early TB: To determine the earliest time point post-infection at which these antigens are recognized by the infected animals, reactivity of the recombinant proteins of clones gsr I-6, II-1 and II-2 with individual guinea pig sera were tested. Western blots prepared from lysate from clone gsr I-6 were probed with the individual sera that were included in the pool used for immunoscreening of the library. The fusion protein band was strongly reactive with the sera obtained 1,3 and 4 weeks post-infection, and weakly reactive with the sera obtained 5 and 6 weeks post-infection. A pool of these sera failed to identify a corresponding sized protein in the control E. coli lysate. (FIG. 6a).

The reactivity of lysate from clone gsr II-1 was evaluated with serum samples from 4 animals each, obtained at 1 and 3 weeks post-infection. (FIG. 6b). Three of the 4 sera at 1 week post-infection and 3 of the 4 sera at 4 weeks post-infection (total 6 out of 8 animals) showed reactivity with the fusion protein in the gsr II-1 lysate. The same sera were also tested for reactivity with the lysate of clone gsr II-2 (FIG. 6c). Three of the 4 sera obtained 1 week post-infection and all 4 samples at weeks 3 post-infection (total 7 out of 8 animals) showed reactivity with the fusion protein. Sera from 2 uninfected guinea pigs showed no corresponding reactivity with either of the lysates. Thus, the antigens encoded by all 3 clones tested showed reactivity with serum samples from animals bled during the early stages of disease progression (1-3 weeks post-infection).

The same 8 sera from weeks 1 and 3 post infection were evaluated for reactivity with the 3 antigen preparations: (CS, SDS-CW and LAM-free CFP). In contrast to the results obtained with the serum pool comprising of sera from animals bled 1-8 weeks post-infection (used for library screening, FIG. 1), all 8 sera from animals bled 1 and 3 weeks post-infection failed to show reactivity with any antigen in the above preparations. However, some of the sera obtained 4-6 weeks post-infection, and the serum obtained 8 weeks post-infection showed reactivity with the three antigen preparations (data not shown).

Validation of the guinea pig as model system for human TB: There are no markers to identify humans who have an active but subclinical infection with Mtb, which may be considered equivalent to the first few weeks post-infection stage of aerosol infected guinea pigs. Therefore, in order to validate the use of these proteins in studies of human immune responses, the following studies have been done:

a. Comparison of antibody reactivity of tuberculous guinea pigs and pulmonary TB patients: Sera from 2 guinea pigs who were infected with aerosolized, virulent Mtb, and bled at 15 weeks post-infection, when they have advanced TB, were obtained from Dr. McMurray. The reactivity of these sera with the culture filtrate and cell-wall associated proteins of Mtb was assessed, and compared to reactivity of sera from 4 patients with confirmed pulmonary TB. Culture filtrate proteins and cell-wall associated proteins of Mtb were fractionated on SDS-PA gels, and the western blots probed with the human TB and guinea pig TB sera at a dilution of 1:100. As seen in FIG. 7, the protein bands in the two antigen preparations recognized by the human and animal TB sera were remarkably similar. Thus, at the advanced stage of active infection, tuberculous humans and guinea pigs have antibodies to the same antigens. While sera from only four TB patients have been studied to date, the finding that 4/4 patients showed similar reactivity to the reactivity observed with sera from tuberculous guinea pigs suggests that our hypothesis that the guinea pig is adequate as a model system relevant to human TB is tenable and worthy of further studies.

b. Reactivity of human TB sera with gsr recombinant proteins: The reactivity of the fusion proteins from seven gsr clones with a pool of sera from 6 PPD positive, healthy individuals, and a pool from 6 TB patients was evaluated. (FIG. 8). Fusion proteins expressed in 5/7 clones were reactive with the pooled TB sera, but not the PPD pool. These results suggest that human TB patients have antibodies to the fusion proteins recognized by the guinea-pig sera. Individual sera from various cohorts have not been evaluated for reactivity with the fusion proteins because each of these β-gal-fusion proteins contains only a small fragment of the original mycobacterial protein, and these small fragments may not account for the immune response to this protein in every diseased individual. For example, the mycobacterial DNA fragment in gsr I-6 expresses only 240 aa of the total 3147 aa long PPE protein, and gsr II-2 expressed only 74 aa of the same protein. Thus, the two clones express ~7.5% and 1.7% respectively, of the parent molecule. Positive reactivity of any fusion protein with human TB sera would indicate that the antigen is relevant to human TB. However, the small fragment of the mycobacterial antigen in the fusion protein lacks most of the regions/epitopes/conformations expressed by the parent molecules, and to which the patients are exposed. The absence of a significant portion of the original protein could provide false negative results when studying individual sera. Moreover, serum samples, especially the pre-clinical TB sera, are available in small amounts (100-200 µl). Thus, it would be unwise and premature to use these valuable sera to test reactivity with the fusion proteins. These sera are being saved for testing with the complete recombinant proteins once they are produced (EXAMPLE 3). This is the reason that more preliminary data with the serum panels available has not been generated. Nevertheless, the reactivity of the fusion protein in gsr1-6 was tested with individual sera from 3 PPD positive individuals, and 4 TB patients. Although the number of individuals tested is small, the reactivity of sera from several TB patients confirms that this protein is recognized during TB in humans (FIG. 9).

In order to determine if these fusion proteins are also recognized during the early stages of disease progression, the reactivity of the fusion proteins from seven gsr clones with a pool of sera from 6 PPD positive, healthy individuals, and a pool from 6 HIV-pre TB sera was also evaluated. These pre-TB sera are retrospective, stored serum samples that were obtained from HIV-infected individuals prior to their developing clinical TB (cohort described in EXAMPLE 4) and represent the earliest stage of TB that can be diagnosed in humans. Fusion proteins from 2 clones (PPE protein encoded by gsr II-2 and the fusion protein encoded by clone gsrII-4) showed reactivity with the pool of the pre-TB sera, and not the pool of PPD control sera Whether the protein expressed by the remaining clones are genuinely not recognized by the pre-TB sera remains to be confirmed since this experiment was done at one serum dilution (1:200) (HIV-infected patients may have lower titers of antibodies) and will be repeated with more concenrated sera, and with complete proteins to confirm the negative results. The volumes of pre-TB sera available are very small (100-200 µl), and studies with individual pre-TB sera are performed only after the full-length proteins are expressed and purified. Such well defined sera are difficult to obtain, and we know of no other cohort that exists.

Ongoing studies with the PPE protein: In order to determine the distribution of the PPE protein encoded by gsr I-6, genomic DNA from Mtb H37Rv, Mtb H37Ra, Mtb Erdman, clinical isolates CSU 11, CSU 17, CSU 19, CSU 22, CSU 25, CSU 26 and CSU 27, *M. bovis*, *M. bovis* BCG, *M. africanum*, *M. microti*, *M. smegmatis*, *M. vaccae*, *M. phlei*, *M. chelonae*, and *M. xenopii* was digested with Eco R1 and southern blofted. A PCR product corresponding to a 481 bp sequence of gene MTV004.03c was used to probe the southern blot. The gene for this PPE protein is present in all members of the TB complex, and all the clinical isolates tested but not in the non-TB mycobacterial species tested (FIG. 10). Currently more clinical isolates and non-TB mycobacterial species are being evaluated to confirm the specificity of this gene. This is continued and expanded as part of EXAMPLE 2.

Several unsuccessful efforts have been made to detect the 309 kDa protein in the culture filtrates or cell wall preparations or sonicates of Mtb. Either this protein is not expressed/very poorly expressed during in vitro growth of Mtb, or is expressed by the bacteria but destroyed by the purification procedures used. Thus, in the case of the PPE protein, the hydrophobic nature (30% LVIFM) of the total protein could result in its being insoluble in aqueous solvents leading to its loss during antigen preparations. To localize the protein in the bacterial cell, high titer antibodies directed against the PPE protein are obtained. For this, the amino-acid sequence of the peptide from gsr I-6 and gsr II-2 has been subjected to Kyte and Doolittle analyses and two amino acid sequences with a high antigenic index identified.

Summary of results: Sera from guinea pigs infected with airborne, virulent Mtb H37Rv, and bled within the first few weeks post-infection have been used to screen an expression library of Mtb DNA. Eight clones have been obtained by the immunoscreening. Of the 3 clones sequenced, two (gsr I-6 and gsr II-1) code for different portions of the same PPE protein, and clone gsr II-2 codes for a protein on the RD3 region of Mtb H37Rv. Thus, we have identified at-least 2 novel antigens that are expressed by the bacteria in vivo during the time when bacterial replication and dissemination is known to occur in this animal model. Preliminary studies suggest that sera from human TB patients have antibodies against the fusion proteins expressed by a majority of these clones.

Example II

Identification of Mtb Antigens that are Expressed in vivo During Early Stages of the Disease In guinea pigs infected by aerosolized virulent Mtb, the in vivo replicating organisms express molecules which are recognized by the humoral immune system of the animals, resulting in antibody production. These antibodies, present in the sera of aerosol infected guinea pigs can be used to identify and obtain the antigens from the expression library.

The approach was to obtain antigens expressed during the early stages of disease progression, sera from Mtb infected guinea pigs, obtained prior to the development of clinical disease. These sera are expected to provide information on the GC content, presence of leader peptides (peptides with high content of hydrophobic amino acids that are often associated with secreted proteins), organization of the genetic loci, etc and will enable the identification of at least some of the genes being expressed.

Example III

Confirmation that Antigens Identified in Example II are Specific to Mtb, or Mtb Complex, and are Widely Present in Clinical Isolates The antigens identified by the immunoscreening may be specific to Mtb, to all members of the Mtb complex, to mycobacteria, or may be products of genes conserved in prokaryotes.

Mtb possesses genes encoding proteins involved in housekeeping fimctions like general metabolism, signal transduction, enzymes, heat shock proteins etc that are conserved in prokaryotes. Mtb will also have genes encoding proteins that are also present in other mycobacteria, for example those involved in novel biosynthetic pathways that generate mycobacterial cell-wall components like mycolic acids (Ag 85 complex), lipoarabinomannans, mycocerosic acid etc. In addition the presence of genes encoding proteins specific to Mtb is likely. The sequencing of the Mtb H37Rv genome has revealed that of the ~4000 open reading frames present, ~20% of the encoded proteins resemble no other known proteins (5). Such specific antigens are likely to be important for diagnostic assays.

Recent studies have reported that there can be genetic differences between clinical isolates of Mtb. Thus, the gene for mtp40 protein of Mtb was recently reported to be present in only some of the clinical isolates tested (42). Similarly, the gene encoding the antigen expressed by the clone gsr II-1 in the studies presented in the progress report has been reported to be present in only 16% of the clinical isolates of Mtb tested (24). Only antigens that are specific to Mtb or Mtb complex, yet are widely present in clinical isolates, are likely to be useful for diagnostic or vaccination purposes. It is therefore important to confirm that the gene for any immunogenic protein identified in EXAMPLE II is a) specific to Mtb or Mtb complex, and b) conserved in Mtb isolates from different geographical isolates. These studies are done by 2 approaches:

a) Genomic DNA from members of the Mtb complex, clinical isolates of Mtb from different geographical locations, and other mycobacterial species are probed with genes identified in EXAMPLE II.

Materials and Methods: Clinical isolates of Mtb from 25 patients from the V.A. Medical Center, Manhattan, 10 patients from the Lala Ram Sarup TB Hospital, New Delhi, India, and 15 patients from the Laboratoire De Sante Hygiene Mobile, Yaounde, Cameroon, Africa have been obtained. Efforts to obtain clinical isolates from patients in additional countries are on going. Thus, isolates from several different geographical regions are used in our studies. Other mycobacterial species (*M. smegmatis, M. gordonae, M. chelonie, M. bovis* BCG, *M. xenopii, M. kansasi, M. fortuitum, M. africanum, M. microti* etc.) have been obtained from the ATCC. 15-20 patient isolates of MATS are obtained from the mycobacteriology laboratory at the VAMC, Manhattan. Non mycobacterial prokaryotes (*E. coli, staphylococcus*, streptococci, *nocardia* etc) are obtained either from the clinical microbiology laboratory at the VAMC, or from the ATCC. Genomic DNA from non-mycobacterial species are isolated by routine methods (35). For isolation of genomic DNA from mycobacterial species, standardized, published methods are used (3). Mycobacteria grown in Middlebrook 7H9 broth are harvested from cultures (2-3 days old for fast growers, 14-21 days for slow growers) and the pellet frozen overnight at −20° C., then thawed and suspended in TE buffer. An equal volume of chloroform/methanol (2:1) are added to the bacterial pellet for 5 min. to remove the cell wall lipids. The suspension is centrifuged, and the bacteria at the organic-aqueous interphase collected. These bacteria are then suspended in TE buffer, followed by 1M Tris-HCl to raise the pH before addition of lysozyme and incubation overnight. This is followed by addition of an appropriate amount of 10% SDS and proteinase K to the cell lysate. The proteins are extracted by Phenol/chloroform/Isoamyl alcohol extraction, the phenol removed by chloroform/isoamyl alcohol extraction, and the DNA precipitated by use of sodium acetate and Isopropanol.

Hybridization and detection methods as per the 'DIG System User's Guide for Filter Hybridization' (Boehringer Manheim) are currently in use in the lab. The genomic DNA is digested with an appropriate restriction enzyme to completion and electrophoresed on agarose gels. The separated DNA fragments are transferred to Hybond-N positively charged membrane (Amersham) and the DNA crosslinked to the membrane by U.V. Specific fragments are obtained from the sequence of the relevant genes (from the Mtb genomic database) from genomic DNA of H37Rv by PCR, labeled with DIG and used to probe the blots prepared from the genomic DNA. Hybridization and washing conditions are optimized for each probe, and the chemiluminescent substrate CSPD used to detect hybridization.

b) Antibodies raised against the mycobacterial peptides from antigens identified in EXAMPLE II are used to probe lysates of the same strains of bacteria by western blotting since it is possible that although the homology at the DNA level is not strong, the expressed proteins may be cross-reactive.

To confirm that further studies are performed only with proteins that are specific to Mtb (or *M. tb* complex), and are conserved amongst clinical isolates of Mtb, the amino-acid sequence of the mycobacterial fragment in the β-gal fusion protein(s) are analyzed for regions that have high antigenicity. A mixture of chemically synthesized peptides representing 2-4 epitopes on each fusion protein are used obtain anti-peptide antibodies from rabbits (commercially). Anti-peptide antibodies are purified from the polyclonal rabbit serum by affinity purification and the antibodies tested to ensure that they recognize the parent fusion protein. Lysates of bacterial strains that were included in the DNA hybridization studies are fractionated by SDS-PAG electrophoresis and western blots probed with the anti-peptide antibodies. These experiments enable us to confirm that there are no cross-reactive proteins in the other bacterial species.

These studies will enable us to identify the antigens of Mtb or Mtb complex, that are conserved in clinical isolates from different sources. As mentioned in the progress report, the methods involved in the completion of this aim are already being used in the lab and no problems are expected. The inclusion of *M. smegnatis* in the studies in EXAMPLE III is crucial because we intend to use this as the host for expression of the full genes of proteins of interest (see EXAMPLE 3)

Example IV

Expression in a Mycobacterial Host of the Antigens Identified in the Screening of Examples II & III Expression cloning of the complete genes will provide the proteins that can be used for immunological studies.

The recombinant clones obtained in EXAMPLE II all express β-gal fusion proteins (FIGS. 2 and 3) which contain only a fragment of the original mycobacterial protein. For immunological studies, complete genes of these proteins will have to be expressed. There is increasing evidence that proteins of Mtb expressed in the *E. coli* host may show differences from the native counterparts. Thus, Mtb super-oxide dismutase expressed in *E. coli* was enzymatically inactive, whereas the same molecule expressed in *M. smegnatis* was enzymatically active (12). Reduced reactivity of human antibodies with recombinant 38 kDa protein, and 10 and 16 kDa proteins has been observed (41). We compared the reactivity of sera from the same TB patients with native Ag 85C and MPT 32 purified from culture filtrates of Mtb, and with the corresponding recombinant molecules expressed in the *E. coli* host (FIG. 11). Our studies showed that human antibodies to MPT 32 and Ag 85C, that were elicited by native antigens during natural disease show lower reactivity with the same proteins expressed in *E. coli* host (FIG. 11). Recent studies have shown that deglycosylation of MPT 32 decreases its capacity to elicit in vitro or in vivo cellular immune responses (32). That glycosylation has a role in proteolytic cleavage of proteins has also been shown for the 19 kDa antigen of Mtb, (17). Also, rMBP 64, expressed in *E. coli* was unable to elicit DTH in sensitized animals whereas the same protein expressed in *M. smegmatis* mimicked the native protein (31). The reasons underlying the differences in the immunological reactivity of native Mtb, and *E. coli* expressed recombinant molecules are not understood, but experience from several labs shows that mycobacterium proteins expressed in a mycobacterial host are immunologically more competent, probably because proteins expressed in *E. coli* lack the post-translational modifications often present on native Mtb antigens (15). Since vectors for efficient expression in *M. smegmatis* or *M. vaccae* have now been constructed and used successfully (11, 12, 15), and since the recombinant proteins obtained in EXAMPLE II are to be used for immunological studies with human sera, the antigens identified by the screening of the library are expressed in mycobacterial hosts to enhance the probability of obtaining proteins that are immunologically similar to the native antigens. Since we intend to express only those antigens that are specific to Mtb, the studies in EXAMPLE III will ensure that *M. smegmatis* does not have cross-reactive proteins or genes, the use of this organism as a host will not be a problem.

Materials and Methods: Two vectors that have been used successfully to express Mtb proteins successfully in *M. smegmatis* have been obtained. Vector pVV16 has been obtained from Dr. John Belisle, CSU. This vector has the origin of replication from pAL5000, the hygromycin resistance gene, the hsp60 promoter, and, in addition, has 6 His-tag sequences at the C terminal end of the expressed protein. The 88 kDa protein, identified in our lab to be a potential candidate for serodiagnosis of TB has successfully been cloned into pVV16 and expressed in *M. smegmatis* (FIG. 12 A). The advantage with this vector is that the hsp60 promoter is a strong promoter resulting in high level constitutive expression of the cloned gene. Also, the His-tag allows the use of commercially available Nickel-Agarose columns (Qiagen) for purification of the cloned protein. The basic method for cloning specific genes into any expression vector is described (11). Briefly, PCR amplification of the target gene are performed using primers that contain restriction sites to generate in-frame fusions. The PCR product are purified and digested with the appropriate restriction enzymes and purified again. The vector DNA will also be cut with the appropriate restriction enzymes and purified. The PCR product and the vector are ligated, electroporated into DH5 and plated onto hygromycin containing plates overnight. Several antibiotic resistant colonies are grown in small volumes of medium, and the plasmid DNA isolated by miniprep. The size of the insert is checked in these colonies. Inserts from one or more colonies are sequenced to ensure fidelity of the amplified gene.

For electroporation into *M. smegmatis*, the bacteria are grown shaking in 7H9 medium till an OD of 0.8-1.0 is obtained. The bacteria are harvested, washed twice with water, once with 10% glycerol and suspended in the same. An aliquot of the *M. smegmatis* cells is electroporated with the plasmid DNA from the colony whose insert was sequenced. The electroporated cells are grown for 3-4 hrs in 7H9, and plated on antibiotic containing plates. Several resistant colonies are grown in minimal media for 48-72 hrs. The bacterial cells are collected, frozen in liquid nitrogen overnight, thawed, suspended in PBS containing protease inhibitors, and sonicated in ice for 5 mins. After centrifuging the lysate for 30 mins at 5000 rpm, the supernatants are aliquoted and frozen. Five-10 ul of the lysate is fractionated on 10% SDS-PA gels, and western blots prepared from these gels are probed with anti-His antibodies to confirm the expression of the protein.

The protein(s) are purified from the lysates by use of commercial Nickel-chelate-nitrilotriacetic acid (Ni-NTA) columns (Quiagen, Inc) (19). These columns allow the purification of proteins constituting <1% of the total cellular protein to >95% homogeneity in one step. Briefly, the *M. smegmatis* containing the cloned genes are grown in Middlebrook 7H9 medium for 72 hrs, after which the bacteria are pelleted by centrifugation and resuspended (1/100 volume) in PBS containing protease inhibitors (PMSF, DTT, EDTA). The bacterial cell pellet is frozen overnight in liquid nitrogen overnight, thawed and exposed to 1 mg/ml lysozyme for 30 mins (in ice). The pellet will then be sonicated and the lysate treated with RNase and DNase for 30 mins. The lysate will then be subjected to high speed centrifugation (>10,000 g for 20 mins) and the supernatant mixed with an equal volume of slurry of Ni-NTA agarose in the appropriate buffer. The His-tagged protein is allowed to bind to the agarose for 60-90 mins in ice, the mix is loaded onto a column, and washed 2-3 times with buffer to get rid of unbound material. The bound protein will then be eluted by use of appropriate elution buffer. The purification procedures for His-tagged proteins may need to be modified for different proteins (19, 20), and the specific conditions for each protein is developed and optimized in consultation with Dr. John Belisle.

As mentioned above, the 88 kDa protein of Mtb has been successfully cloned into this vector (FIG. 12A). Lysates of *M. smegmatis* mc2 alone and mc2 with the 88 kDa-pVV16 (10 μg/lane) were fractionated by SDS-PAGE and western blots probed with anti-His antibodies. The His-tagged 88 kDa recombinant protein is well expressed and easily detectable.

One possible problem that may be encountered with one or more of the proteins cloned in this vector is that accumulation of foreign proteins can sometimes lead to toxicity to the host cell, or the recombinant protein forms inclusion bodies which necessitates denaturation of the protein for purification. An alternative vector, pDE 22 has been obtained from Dr. Douglas Young, Imperial College, London. This vector is derived from a vector pSMT3 which has been used successfully for expression of 4 different Mtb proteins (11, 15), and also contains the pAL5000 origin of replication, the gene for hygromycin resistance, the hsp60 promoter and has the signal sequence from BCG alpha gene. In this case, the recombinant protein is secreted out of the host, and so toxicity to the host or inclusion body formation is not a problem. Moreover, this vector can also be used for expression in *M. vaccae* if required. The proteins cloned into pDE 22 are secreted out of the host, and the recombinant protein is present in the culture supernatants. One problem that may be encountered in the use of this plasmid is that the *M. smegmatis* host itself may express proteins that cross-react with the Mtb protein. To determine if cross-reacting extracellular antigens are present in culture filtrates of *M. smegmatis*, the organisms were grown in minimal media. The culture supernatants obtained after 24, 48 and 72 hrs of growth were concentrated 30-fold by Amicon filtration (10 kDa cut-off), 10 μgs fractionated on a 10% SDS-PA gel and 2 identical blots containing fractionated, concentrated culture filtrate proteins and LAM-free CFP (as positive control) probed with TB sera or healthy control sera. The TB sera recognized several proteins in the LAM-free CFP preparation, but no specific bands in the concentrated *M. smegmatis* culture filtrate (FIG. 12B). The healthy control sera showed no reactivity with either of the antigen preparations. These results show that *M. smegmatis* itself does not produce any extracellular proteins that cross-react with sera from TB patients.

Example V

Assessing the Role of the Recombinant Proteins in Humoral Responses

Antibodies to the recombinant antigens identified in EXAMPLES II and III are present in the sera of individuals with clinical and/or subclinical active TB.

Scant information is available on the Mtb antigens that are expressed by the in vivo bacteria and are recognized by the human immune system during the early stages of disease progression. The guinea-pig sera used to obtain the antigens was from animals that had been infected with aerosolized, virulent, Mtb and bled before they developed the disease. The antibodies in the sera of the animals at this stage are directed against antigens that are expressed by the bacteria during this pre-clinical period of bacterial replication and dissemination. The profile of antigens of Mtb recognized by tuberculous guinea pigs and humans is very similar (FIG. 7). Moreover, human TB serum pools show reactivity with fusion proteins from several clones (FIG. 8). The fusion protein encoded by clone gsr 1-6 is recognized by sera from TB patients but not by sera from healthy controls (FIG. 9). The HIV-pre TB serum pool recognizes at least 2 of the antigens (FIG. 10). Together these results support the hypothesis that the antigens identified by guinea pig sera will also be recognized by the human TB sera. Evaluation of reactivity of proteins identified in this study with sera from patients at different stages of disease will enable us to determine which of these antigens is recognized by humans during early TB.

Materials and methods: In order to determine the stage of TB infection at which antibodies to these antigens are present in humans, and their utility in serving as markers of active infection, antibodies to them are assessed in serum samples in the already existing cohorts in the lab. Sera from the following cohorts are available in the PI's laboratory.

Sera from non-TB controls: Sera from 40 PPD positive and 60 PPD negative healthy controls are available in the laboratory. These sera are used as negative controls for assessment of antibodies to the recombinant antigens in the sera from TB patients at different stages of disease progression. Sera from ~50 HIV-infected, asymptomatic individuals are also available, and are included as additional controls.

Pre-TB and TB sera from HIV-infected individuals: We currently have sera from >50 HIV-infected patients who developed clinical TB {and >200 serum specimens from the same subjects that were obtained prior to their developing TB (pre-clinical TB)}. These are HIV-infected individuals who were being regularly monitored for their T cell profiles, and developed clinical TB during the course of the HIV disease progression. Serum/plasma samples from each time when the T cell profiles were evaluated was saved, providing us with retrospective sera that were obtained prior to clinical manifestations of TB, that is, during pre-clinical disease (21). Chest X-ray reports, and microbiological data from these patients are also available. This is the earliest stage of active infection that can be recognized in humans. Since these sera are from pre-clinical stages of tuberculosis, they should contain antibodies to the antigens expressed during early stages of tuberculosis disease progression. This is a unique, well-characterized and extremely valuable set of specimens which, to the best of our knowledge, does not exist anywhere else. Only with such a specimen bank could these studies be undertaken.

Sera from minimal TB patients: Serum samples from 20 patients with non-cavitary TB are available in the laboratory. A majority of these patients are also smear negative for Acid Fast Bacilli. These patients are at a relatively early stage of disease progression, defined as "early TB" or "early infection." These patients are from the Manhattan Va. Medical Center. Sera from additional patients with a similar clinical profile are obtained with informed consent, during the course of the studies.

Sera from advanced TB patients: Serum samples from 60 cavitary, smear positive patients have been obtained from India and from about 20 similar patients from the Manhattan VA medical center. These sera represent samples obtained at an advanced stage of disease progression.

Sera from HIV-infected individuals with *M. avium* bacteremia: The pre-TB sera are derived from HIV-infected patients. These patients are also at high risk for having *M. avium* infection. To further ensure the specificity of the antibody responses to the recombinant antigens, sera from 20 HIV-infected individuals who developed *M. avium* bacteremia, obtained at the time of disease manifestation, and in the months or years prior to the bacteremia (equivalent to the pre-TB and at-TB sera from HIV-TB patients) have also been obtained. These sera will also be used as negative controls.

The sera in the above cohorts represent sera obtained at different stages of disease progression in humans. Reactivity of these sera with the purified proteins are assessed by ELISA. The method used is the same as described in our previous publications. Briefly, the recombinant antigens purified from *M. smegmatis* supernatants or lysates are used to coat the ELISA plates at a predetermined optimal antigen concentration overnight. Next morning, the plates are washed, blocked with PBS containing 5% BSA and 2.5% FCS for 2.5 hrs. This is followed by the addition of a predetermined optimal dilution(s) of the serum samples to the antigen-coated wells. After incubating the antigen coated wells with antibody containing sera for 90 mins, the plates are washed with PBS containing 0.05% Triton-X and then exposed to alkaline phosphatase-conjugated anti-human IgG, followed by the substrate for the enzyme. We routinely use the GIBCO-BRL amplification system as the substrate since it increases the sensitivity of antibody detection. Checkerboard titration is used to determine the optimal antigen concentration, and serum dilution for each antigen. For MPT 32 and Ag 85C, as little as 50 μls per well of a 2 μg/ml suspension of the purified protein was required for optimal results. Mean optical density plus 2.5-3 SD with the sera from the healthy individuals is used as the cut-off to determine positive reactivity of patients. Reactivity with the guinea pig sera which were used for the initial immunoscreening of the λgt11 library is included as positive control.

Studies with the above cohorts of sera will help to identify the antigens that are expressed by the in vivo *M. tb*, and recognized by the immune system during different stages of disease progression in humans. We expect that some antigens (that are expressed by the in vivo bacteria at all stages of disease progression) are reactive with antibodies from patients at all different stages of TB described in the cohorts above. Antibodies to these antigens are absent in various groups of negative controls (including the PPD+ healthy individuals). Such antigens are very useful for devising diagnostic tests since a single test could then be used to diagnose TB at any stage of the disease progression. However, the in vivo bacteria may express some antigens only during early stages of TB, and not during advanced TB. Such antigens would be recognized only by antibodies obtained during early TB, for example by the pre-TB sera from the HIV-infected individuals. Such antigens are useful for devising tests for identification of individuals who are at high risk of developing infectious TB.

Reactivity of sera from a cohort of individuals at high risk of developing TB: Dr. J. J. Ellner, TB Research Unit (TBRU), Case Western Reserve University, had initiated studies with a cohort comprising of families with one or more index cases of confirmed TB during the last 2 years in Uganda. Three hundred and two families with at least one smear positive TB case are included in the study, with approximately 1200 household contacts. All contacts were evaluated for clinical TB, TB infection and underlying diseases that may predispose to TB at the time of inclusion into the study.

Over the past year, 14 of the household contacts who did not initially have any signs and symptoms of TB have developed TB during follow up. Baseline sera (obtained at the time of inclusion into the study), and sera obtained during follow up from contacts who developed TB during the course of the study are evaluated for reactivity with the antigens obtained in EXAMPLE IV. An equal number of household contacts who did not develop TB, and are members of the same families are included in this testing as negative controls. Any additional contacts who develop TB during the course of the study will also be included in these studies. This longitudinal study is designed to determine which antigens can be used as surrogate markers for identification of individuals who are at a risk of developing TB in high-risk populations. The selection of the individuals and the sera, the number and appropriateness of the controls and the analysis of the data is done in consultation with Dr. Christopher Whalen, Epidemiology leader for the TB Research Unit.

Cohort of recent converters of PPD reactivity: The VA assesses the PPD skin test reactivity of all employees and volunteers (~1500 individuals) on an annual basis. Of these, ~500 are baseline positive. All individuals working in the emergency room, medical intensive care unit and those involved in taking care of the TB patients are tested every six months. About 5-10 individuals convert to positive reactivity every year. The testing is done with 5 US units/test, of tuberculin obtained from Pasteur-Meriuex Corporation, and 10 mm or greater induration is considered positive. Sera from recent converters of PPD skin test are obtained with their informed consent. The reactivity of the sera obtained from recent converters with the recombinant antigens is determined by the above described methods, and compared to the reactivity with an equal number of long term PPD positive individuals. Since these individuals are employees of the hospital, both male and female individuals are included in the cohort.

Summary: This study focuses on identifying, obtaining and studying the antigens of Mtb which are expressed by the bacterium during in vivo replication. No such antigens that are associated with early TB have been described before. The fact that one of the antigens we identified is a PPE protein is interesting, since other pathogens have similar proteins, which elicit cellular and humoral immune responses in their hosts, and also contribute to immune evasion by antigenic variation The studies of humoral responses elicited by these antigens contribute to the development of diagnostic assays. If, as in guinea-pigs, humans also recognize one or more of these proteins prior to clinical manifestation of TB, these antigens can be included in tests that can be used to screen large numbers of suspect individuals quickly. The detection of individuals with early, subclinical disease will enable clinicians to institute treatment to patients before they develop disease and become infectious. This will benefit not only the individuals themselves, but also contribute significantly to decreasing the transmission of the infection in the community.

Literature References Cited in Examples I-V

1 Altschul, S. F., W. Gish, W. Miller, E. W. Myers, and D. J. Lipman. 1990. Basic Local Alignment Search Tool. J. Molecular Biology. 215:403-410.

2 Amara, R. R., and V. Satchidanadam 1996. Analysis of a genomic DNA expression library of mycobacterium tuberculosis using tuberculosis patient sera: evidence for modulation of host immune response. Infect. Immun. 64:3765-3771.

3 Belisle, J., and M. Sonnenberg. 1999. Isolation of genomic DNA from Mycobacteria, p. 31-44. In T. Parish and N. Stoker (ed.), Methods in Molecular Biology: Mycobacteria Protocols, vol. 101. Humana Press, London, UK.

4 Bothamley, G. H., R. Rudd, F. Festenstein, and J. Ivanyi. 1992. Clinical value of the measurement of *Mycobacterium tuberculosis* specific antibody in pulmonary tuberculosis. Thorax. 47:270-275.

5 Cole, S. T., R. Brosch, J. Parkhill, T. Garnier, C. Churcher, D. Harris, S. V. Gordon, K. Eiglneier, S. Gas, C. E. Barry III, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, A. Krogh, J. McLean, S. Moule, L. Murphy, K. Oliver, J. Osborne, M. A. Quail, M. A. Rajandream, J. Rogers, S. Rutter, K. Seegar, J. Skelton, R. Squares, S. squares, J. E. Sulston, K. Taylor, S. Whitehead, and B. G. Barell. 1998. Deciphering the biology of *Mycobacterium tuberculosis* from the complete genome sequence. Nature. 393:537-544.

6 Converse, P. J., J. Arthur M. Dannenberg, J. E. Estep, K. Sugisaki, Y. Abe, B. H. Schofield, and M. L. M. Pitt. 1996. Cavitary tuberculosis produced in rabbits by aerosolized virulent tubercle bacilli. Infect. Immun. 64:4776-4787.

7 Daniels, T. M. 1996. Immunodiagnosis of Tuberculosis, p. 223-231. In W. R. Rom and S. Garay (ed.), In: Tuberculosis. Little, Brown and Company, Inc, Boston, Mass.

8 Dannenberg, A. M., Jr. 1991. Delayed-type hypersensitivity and cell mediated immunity in the pathogenesis of immunity. Immunol. Today. 12:228-233.

9 Engers, H. D., J. Bennedsen, T. M. Buchanan, S. D. Chaparas, D. Kadival, O. Closs, J. R. David, J. D. A. Van Embden, T. Godal, S. A. Mustafa, J. Ivanyi, D. B. Young, S. H. E. Kaufman, A. G. Khomenko, A. H. J. Kolk, M. Kubin, J. A. Louis, P. Minden, T. M. Shinnick, L. Trnka, and R. A. Young. 1986. Results of a World Health Organization-sponsored workshop to characterize antigens recognized by mycobacterium-specific monoclonal antibodies. Infect. Immun. 51:718-720.

10 Espitia, C., J. P. Laclette, M. Mondragon-Palomino, A. Amador, J. Campuzano, A. Martens, M. Singh, R. Cicero, Y. Zhang, and C. Moreno. 1999. The PE-PGRS glycine-rich proteins of *Mycobacterium tuberculosis*: a new family of fibronectin-binding proteins. Microbiology. 145:3487-3495.

11 Gaora, P. 1998. Expression of genes in mycobacteria, p. 261-273. In T. Parish and N. G. Stoker (ed.), Methods in Molecular Biology:Mycobacteria Protocols, vol. 101. Humana Press.

12 Garbe, T., D. Harris, M. Vordermeier, R. Lathigra, J. Ivanyi, and D. Young. 1992. Expression of the *Mycobacterium tuberculosis* 19-kilodalton antigen in *Mycobacterium* smegmatis:Immunological analysis and evidence of glycosylation. Infect. Immun. 61:260-267.
13 Grange, J. M. 1984. The humoral immune response in tuberculosis: its nature, biological role and diagnostic usefulness. Adv Tuberc Res. 21:1-78.
14 Grange, J. M. 1996. The natural history of tuberculosis, Mycobacteria and Human Disease, Second Edition ed. Oxford University Press, New York.
15 Harth, G., B.-Y. Lee, and M. A. Horwitz. 1997. High-Level Heterologous Expression and Secretion in Rapidly Growing Nonpathogenic Mycobacteria of Four Major *Mycobacterium tuberculosis* Extracellular Proteins Considered To Be Leading Vaccine Candidates and Drug Targets. Infect Immun. 65:2321-28.
16 Headley, V. L., and S. H. Payne. 1990. Differential protein expression by *Shigella flexneri* in intracellular and extracellular environments. Proc Natl Acad Sci USA. 87:4179-4183.
17 Herrmann, J., P. O'Gaora, A. Gallagher, J. Thole, and D. Young. 1996. Bacterial glycoproteins: a link between glycosylation and proteoltic cleavage of a 19 kDa antigen from *Mycobacterium tuberculosis*. EMBO J. 15:3547-3554.
18 Ho, R. S., J. S. Fok, G. E. Harding, and D. W. Smith. 1978. Host-parasite relationships in experimental airborne tuberculosis. VII. Fate of *Mycobacterium tuberculosis* in primary lung lesions and in primary lesion-free lung tissue infected as a result of bacillemia. J. Infect. Dis. 138:237-241.
19 Kneusel, R. E., J. Crowe, M. Wulbeck, and J. Ribbe. 1999. Procedures for the Analysis and Purification of His-Tagged Proteins. Methods in Molecular medicine. 13:293-308.
20 Kneusel, R. E., M. Wulbeck, and J. Ribbe. 1999. Detection and Immobilization of Proteins Containing the 6×His Tag. methods in Molecular medicine. 13:309-321.
21 Laal, S., K. M. Samanich, M. G. Sonnenberg, J. T. Belisle, J. O'Leary, M. S. Simberkoff, and S. Zolla-Pazner. 1997. Surrogate marker of preclinical tuberculosis in human immunodeficiency virus infection: antibodies to an 88 kDa secreted antigen of *Mycobacterium tuberculosis*. J. Infect. Dis. 176:133-143.
22 Laal, S., K. M. Samanich, M. G. Sonnenberg, S. Zolla-Pazner, J. M. Phadtare, and J. T. Belisle. 1996. Human humoral responses to antigens of *Mycobacterium tuberculosis*:immunodominance of high molecular weight antigens. Clin. Diag. Lab. Immunnol. 4:49-56.
23 Li, Z., A. Howard, C. Kelley, G. Delogu, F. Collins, and S. Morris. 1999. Immunogenicity of DNA vaccines expressing tuberculosis proteins fused to tissue plasminogen activator signal sequences. Infect. Immun. 67:4780-4786.
24 Mahairas, G. G., P. J. SAbo, M. J. Hickey, D. C. Singh, and C. K. Stover. 1996. Molecular Analysis of genetic differences between *Mycobacterium bovis* BCG and Virulent *M. bovis*. J. Bacteriol. 178:1274-1282.
25 Mekalanos, J. J. 1992. Environmental signals controlling expression of virulence deterninants in bacteria. J. Bacteriol. 174:1-7.
26 Modun, B., P. Williams, W. J. Pike, A. Cockayne, J. P. Arbuthnott, R. Finch, and S. P. Denyer. 1992. Cell envelope proteins of *Staphylococcus epidermis* grown in vivo in a peritoneal chamber implant Infect Immun. 60:2551-2553.
27 Power, C. A., G. Wei, and P. A. Bretscher. 1998. Mycobacterial dose defines the Th1/Th2 nature of the immune response independently of whether immunization is administered by the intravenous, subcutaneous, or intradermal route. Infect. Immun. 66:5743-5750.
28 Ramakrishnan, L., N. A. Federspiel, and S. Falkow. 2000. Granuloma-Specific Expression of Mycobacterium Virulence proteins from the glycine-rich PE-PGRS family. Science. 288:1436-1439.
29 Raviglione, M. C., J. P. Narain, and A. Kochi. 1992. HIV-associated tuberculosis in developing countries: clinical features, diagnosis, and treatment. Bull World Health Organization. 70:515-526.
30 Raviglione, M. C., D. E. Snider, and A. Kochi. 1995. Global epidemiology of Tuberculosis: Morbidity and mortality of a worldwide epidemic. Jama. 273:220-226.
31 Roche, P. W., N. Winter, J. A. Triccas, C. G. Feng, and W. J. Britton. 1996. Expression of *Mycobacterium tuberculosis* MPT64 in recombinant *Mycobacterium smegmatis*: purification, immunogenicity and application of skin tests for tuberculosis. Clin. Exp. Imunnol. 103:226-232.
32 Romain, F., C. Horn, P. Pescher, A. Namane, M. Riviere, G. Puzo, 0. Barzu, and G. Marchal. 1999. Deglycosylation of the 45/47-Kilodalton Antigen Complex of mycobacterium tuberculosis Decreases It;s capacity To Elicit In Vivo or in Vitro Cellular Inimunce Responses. Infect. Immun. 67:5567-5572.
33 Sada, E., P. J. Brennan, T. Herrera, and M. Torres. 1990. Evaluation of lipoarabinomannan for the serological diagnosis of tuberculosis. J. Clin Microbiol. 28:2587-2590.
34 Sada, E., L. E. Ferguson, and T. M. Daniel. 1990. An ELISA for the serodiagnosis of tuberculosis using a 30,000-Da native antigen of *Mycobacterium tuberculosis*. J. Inf Dis. 162:928-931.
35 Sambrook, J., E. F. Fritsch, and T. Maniatis. 1989. Molecular cloning: a laboratory manual. Cold Spring Harbor Laboratory Press, Cold Spring Harbor, N.Y.
36 Skurnik, M., and P. Toivanen. 1993. Yersinia entercolitica lipopolysaccharide: genetics and virulence. Trends Microbiol. 1:148-152.
37 Smith, D. W., D. N. McMurray, E. H. Wiegeshaus, A. A. Grover, and G. E. Harding. 1970. Host parasite relationships in experimental airborne tuberculosis IV. Early events in the course of infection in vaccinated and nonvaccinated guinea pigs. American Rev. of Respiratory Disease. 102:937-949.
38 Smith, D. W., and E. H. Wiegenshaus. 1989. What Animal Models Can Teach Us About the Pathogenesis of Tuberculosis in Humans. Reviews of Infect. Dis. 2:s385-s393.
39 Sonnenberg, M. G., and J. T. Belisle. 1997. Definition of *Mycobacterium tuberculosis* culture filtrate proteins by two-dimensional polyacrylarnide gel electrophoresis, N-terminal amino acid sequencing and electrospray mass spectrometry. Infect. Immun. 65:4515-4524.
40 Triccas, J. A., F.-X. Berthet, V. Pelicic, and B. Gicquel. 199. Use of fluorescence induction and sucrose counterselection to identify *Mycobacterium tuberculosis* genes expressed within host cells. Microbiology. 145:2923-2930.
41 Verbon, A. 1994. Development of a serological test for tuberculosis. Trop Geo Med. 46:275-279.
42 Weil, A., B. Pikaytis, W. Butler, C. Woodley, and T. Shinnick. 1996. The mtp40 gene is not present in all strains of *Mycobacterium tuberculosis*. J. Clin. Microbiol.:2309-2311.
43 Wiegeshaus, E. H., D. N. McMurray, A. A. Grover, G. E. Harding, and D. W. Smith. 1970. Host-parasite relationships in experimental airborne tuberculosis III. Revelance of microbial enumeration to acquired resistance in guinea pigs. Am. Rev. Respir. Dis. 102:422-429.

44 Young, D. B., S. H. E. Kaufinann, P. W. M. Hermans, and J. E. R. Thole. 1992. Mycobacterial protein antigens: a compilation. Mol. Microbiol. 6:133-145.

45 Young, R. A., B. R. Bloom, C. M. Grosskinsky, J. Ivannyi, D. Thomas, and R. W. Davis. 1985. Dissection of *Mycobacterium tuberculosis* antigens using recombinant DNA. Proc. Natl. Acad. Sci. USA. 82:2583-2587.

Examples VI-XIII

Parts of the studies described in Examples VI-XIII below were also published in K. K. Singh, X. Zhang, A. Sai Patibandla, P. Chien and S. Laal: Antigens of Mtb Expressed During Pre-Clinical TB: Serological Immunodominance of Proteins with Repetitive Amino Acid Sequences, *Infec. Immun.* 69:4185-4191 (1991), which is incorporated by reference in its entirety. References cited in these Examples as numbers in parentheses are listed following Example XIII.

Example VI

Materials and Methods

Serum samples from rabbits: Six pathogen-free rabbits (2.5 to 2.7 kg, Covance Research Products, Inc., Denver, Pa.) were infected by aerosols of Mtb H37Rv and another six were similarly infected by aerosol of Mtb CDC 1551 at the US Army Medical Research Institute of infectious Diseases, F. Detrick, Frederick, Md. (10). After infection, the rabbits were maintained in the BL3 facility at George Washington University, Washington, D.C. The infected rabbits were bled 5 weeks post-infection when they were euthanized for determination of tubercles in their lungs (6). All 12 rabbits showed the presence of tubercles, confirming that all animals had been successfully infected. Also, there was no significant difference in the numbers of tubercles, or in the bacterial loads in the tubercles, between the rabbits infected by the H37Rv or CDC1551 strains (6). Sera from 3 normal (uninfected) rabbits was obtained as controls.

Serum samples from Humans: Sera were obtained from the following groups of individuals:

a) 5 PPD sldn test positive, healthy individuals. Three of the 5 individuals were BCG vaccinated, and all 5 would also be potentially exposed to the bacteria since they were individuals working in the laboratory or were clinicians working in the VA Infectious Disease Clinic.

b) 10 HIV-infected patients: This patient cohort has been described earlier (24). Briefly, these were HIV-infected individuals who were routinely being monitored for their CD4 numbers, and developed TB during the course of HIV disease progression. At each time point when they were bled for evaluation of the T cell numbers, plasma from these patients had been saved and frozen. Thus, when they developed TB, it was possible to identify and obtain the retrospective, pre-TB sera. Multiple samples from each individual are available, but for the current study, one randomly chosen pre-TB serum obtained around 6 months prior to clinical TB was used for each individual.

c) 2 TB patients with early disease: These were smear negative, culture positive TB patients with infiltration in their lungs but no radiological evidence of cavitary lesions.

d) 5 TB patients with advanced disease: These were smear positive TB patients with extensive cavitary lesions.

Mtb H37Rv antigen preparations: Two antigen preparations of Mtb H37Rv, lipoarabinomannan (LAM)-free culture filtrate proteins (LFCFP), and SDS-soluble cell-wall proteins (SDS-CWP) were tested in the study. The preparation of these antigens has been described previously (25). The former antigen preparation contains >100 different proteins, some of which (~30%) have been mapped on the basis of reactivity with murine monoclonal antibodies or peptide sequencing (41). The latter preparation contains~estimate different proteins but these have not been mapped as yet.

Immunoscreening of Mtb λgt11 library: Mtb λgt11 expression library was obtained from the World Health Organization (47). The library contains random sheared fragments of Mtb H37Rv DNA cloned into λgt11 phage that expresses the foreign insert DNA as *E. coli* β-galactosidase (β-gal) fusion protein. Immunoscreening of expression library was performed by standard methods (47). Briefly, *E. coli* Y1090 was infected with phage from the library and plated in top agar on LB plates. After 2.5 h incubation at 42° C., expression of recombinant proteins was induced by overlaying the plates with Isopropyl β-D thiogalactoside (IPTG, Sigma) saturated nitrocellulose filters for 2.5 h at 37° C. The filters were removed, washed and probed with 1:50 dilution of a serum pool from the above described 12 infected rabbits. The serum pool was absorbed extensively with an *E. coli* lysate before use. The recombinant phages producing positive signals were cloned and designated as AD clones.

Western Blot analysis: This was used both for evaluating reactivity of the rabbit sera with the LFCFP and the SDS-CWP preparations, as well as characterization of the recombinant proteins expressed by the AD clones. Briefly, the Mtb antigen preparations were fractionated on 10% SDS-PA gels, and the western blots probed with serum pools from Mtb infected or uninfected rabbits. The blots were washed with PBS, and blocked with PBS containing 3% BSA for 2 h. After washing the blots with PBS-2% Tween 20 (PBST), they were incubated overnight with the rabbit pools described at a dilution of 1:60 in PBST-1% BSA at 4° C. after which they were washed with PBST and exposed to 1:2000 dilution of alkaline phosphatase-conjugated goat anti-rabbit IgG (Sigma, St Louis, Mo.) for 1.5 h. Extensively washed blots were developed with BCIP-NBT substrate (Kirkegard & Perry Labs, Gaithersburg, Md.).

For the recombinant protein studies, lysogenic strains were prepared from phage clones in *E. coli* Y1089 (37). Single colonies from lysogens were grown in LB medium at 32° C. till midlog (optical density of 0.5 at 600 nm), induced at 45° C. for 20 min and followed by addition of IPTG (10 mM) and further incubation at 37° C. for 1 h. The bacterial pellets obtained were sonicated in a small volume of PBS containing 1 mM of DTT, EDTA and PMSF, and the lysates fractionated on 10% SDS-PAGE gels. The western blots were probed as described above with the serum pool from infected rabbits (1:200), or with a pool of sera from uninfected rabbits (1:200) or with murine anti-β-gal monoclonal antibody (1:10,000) (Promega), or with human sera (1:100-1:700) and the appropriate alkaline phosphatase-conjugated IgG secondary antibody. Lysates from *E. coli* Y1089 lysogenized with λgt11 phage without insert were included as controls.

Isolation, sequencing and computer analysis of DNA from recombinant λgt11 clones: DNA from recombinant λgt11 clones was isolated by using Qiagen λ DNA purification kit (Qiagen, Valencia, Calif.), digested with EcoRI for release of mycobacterial DNA insert, and the insert DNA purified by extracting from low melting agarose gel with QIAquick gel extraction kit (Qiagen,). The purified EcoRI insert DNA was subcloned into vector pGEMEX-1 (Promega, Madison, Wis.) at the EcoRI site and the recombinant plasmid transformed into JM 109 competent cells. The recombinant plasmid DNA was isolated using Wizard plus minipreps kit (Promega), and used for sequencing with SP6 and T3 promoter primers flanking the multiple cloning site in pGEMEX-1. The sequence similarity analysis of the DNA sequences was performed by BLAST using the National Center for Biotechnology Information site (NCBL USA). The repetitive structures in the protein were analyzed by using Statistical Analyses of Protein sequences (SAPS). Prediction of trans-membrane helices was performed by TMpred software using ISREC server at European Molecular Biology Research network-Swiss node site. The prediction of signal peptide and signal peptidase cleavage sites were performed by the SignalP V2.0 software using neural networks (NN) and hidden Markov models (HMM) trained on gram positive bacteria, available from Center for Biological Sequence Analyses (CBSA, Denmark). The glycosylation sites were predicted by using the NetOGlyc 2.0 software also available from the CBSA. The Kyte & Doolittle hydrophobicity plot and theoretical molecular weight and pI of the proteins were performed by using software from ExPASy site. Prosite profile scan was performed by ISREC server at Swiss Institute for Bioinformatics (SIB).

Example VII

Reactivity of Mtb Infected Rabbit Serum Pool with LFCFP and the SDS-CWP Preparations Studies with other intracellular bacterial pathogens suggest that the first crucial steps towards establishment of the infecting organism, adhesion and invasion, are likely to be mediated by extracellularly expressed or cell surface associated proteins of the pathogen (21, 22, 32). To determine if any antigens in the culture filtrates or cell-wall preparations of Mtb are recognized by antibodies from the infected rabbits at 5 weeks post-infection, a pool of sera from all 12 rabbits was used to probe the LFCFP and SDS-CWP preparations (FIG. 13), and the reactivity compared with a pool of sera from 3 uninfected rabbits. Three bands corresponding to ~27.5 kDa, 35.5 kDa and 56 kDa in LFCFP preparation were reactive only with the serum pool from the infected rabbits, as were two bands corresponding to ~27.5 kDa and 43 kDa in the SDS-CWP preparation (FIG. 13, lane 3 and 5). The serum pool from the infected rabbits was absorbed extensively against a lysate of E. coli Y1090 and used to screen the λgt11 expression library of Mtb H37Rv genomic DNA (47).

Example VIII

Screening of the λgt11 Library and Characterization of the Recombinant Proteins

To obtain the antigenic proteins that are recognized by antibodies in the sera from the Mtb infected rabbits, ~1.2×10$^5$ pfu from the library were screened with the serum pool. Seven clones were plaque purified, and designated AD1, AD2, AD4, AD7, AD9, AD10, and AD16.

Lysates prepared from cultures of single colonies of lysogens of all 7 AD clones were fractionated on 10% SDS-PAGE, and the western blots probed with the rabbit serum pools from infected or uninfected rabbits, or mouse anti-β-gal monoclonal antibody. As shown in FIG. 14, all 7 recombinant clones produced β-gal fusion proteins, with sizes ranging from 125 kDa to 170 kDa, which were recognized both the anti-β-gal mAb (FIG. 14 lanes 2-8) and with the rabbit serum pool from the infected rabbits (FIG. 14, lanes 20-26). The recombinant fusion proteins failed to react with the serum pool prepared from uninfected rabbits (FIG. 14, lanes 11-17).

DNA Sequence and Protein Analyses

Restriction digestion 5 of the 7 clones with EcoRI yielded single insert ranging from 3.7 kb to 5.6 kb. The remaining clones had multiple inserts. This manuscript reports the results obtained with the five clones with single EcoR1 inserts. Sequencing of the EcoR1 inserts of the 5 clones after subcloning into PGEMEX-1 resulted in sequencing of about 450-700 bp nucleotides from each end. Orientation of the insert in the AD clones were determined by restriction map analysis (data not shown).

Example IX

Sequence Analyses of Clones AD1 and AD2

Figure 15A:
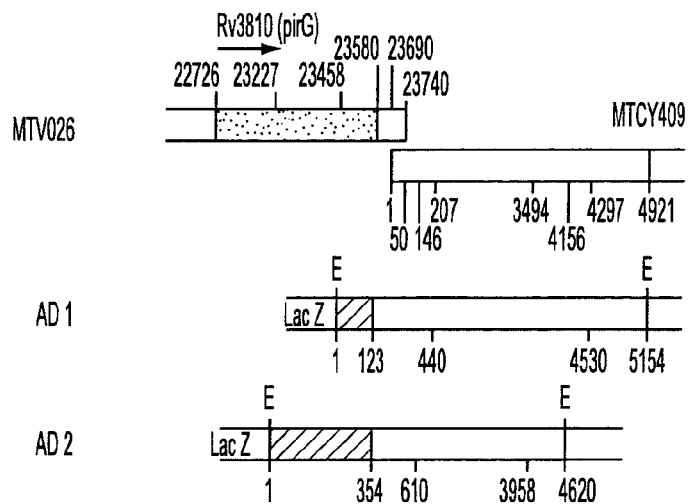

DNA sequence analyses of both ends of EcoR1 insert of clones AD1 (5.1 kb) and AD2 (4.6 kb) showed 98% identities to different regions of two overlapping cosmids MTV026 and MTCY409. One end of the insert of clone AD1 (nu 1-440) showed homology to nu 23458-23740 of cosmid MTV026 and nu 1-207 of overlapping cosmid MTCY409 while the other end (nu 4530-5154) showed homology to nu 4297-4921 of cosmid MTCY409 (FIG. 15A). Similarly, one end of the insert of clone AD2 (nu 1-610) showed homology to nu 23227-23740 of cosmid MTV026 and nu 1-146 of cosmid MTCY409 while the other end (nu 3958-4620) showed homology to nu 3494-4156 of cosmid MTCY 409 (FIG. 15A). Restriction map analysis showed that the ends of the inserts of clones AD1 and AD2 which showed homology with cosmid MTV026 was in correct reading frame with β-gal.

The peptide expressed in clones AD1 (nu 1-123) and AD-2 (nu 1-354) represents amino acids 245-284 and 168-284 respectively in the C-terminal region of Rv3810 (pirG) gene product. The protein encoded by the Rv3810 (pirG) is a 284 amino acid cell surface protein precursor, which is almost identical (99.3% identity in 284 aa overlap) to previously described cell surface protein ERP (exported repetitive protein) of Mtb (4) and secreted antigen p36/p34 (5) of M. bovis. This gene also shows 53.4% identity to a M. leprae gene for a 28 kDa protein (7). As reported earlier, the ERP protein has 12 tandem repeats of five amino acid PGLTS in the central region from position 92 to 173. The theoretical molecular weight and pI of the protein are 27.6 kDa and 4.34 respectively, although the molecular weight of the native molecule was reported to be 36 kDa (3). The protein has a typical N-terminal signal sequence with a possible signal peptidase cleavage site at position 22. The Kyte-Dolittle plot demonstrated hydrophobic regions in the N-terminal and C-terminal portion of the protein which have no repeat motifs and a hydrophilic central portion which contains all the repeat motifs.

Example X

Sequence Analyses of Clone AD9

Figure 15B:
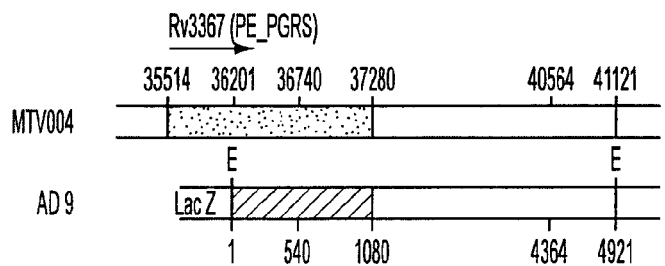

DNA sequence analyses of both ends of EcoR1 insert of clone AD9 (4.9 kb) showed 94% identities to different regions of cosmid MTV004. One end of the insert (nu 1-540) showed homology to nu 36201-36740 and other end (nu 4364-4921) to nu 40564-41121 of the cosmid (FIG. 15B). Restriction map analysis showed that the end of the insert of clone AD9 which is in correct reading frame with β-gal, starts within the gene Rv 3367 (PE-PGRS). The peptide expressed in clone AD9 (nu 1-1080) represents amino acids 230-588 in the C-terminal region of Rv3367 (PE-PGRS) gene product (FIG. 16).

The protein encoded by the Rv3367 (PE_PGRS) is a 588 amino acid protein, which is a member of recently described PE-PGRS family of glycine-rich Mtb proteins (9). This protein possesses the highly conserved N-terminal domain of ~110 residues and Pro-Glu (PE) motif near the N-terminus described to be characteristic of the PE protein family (9). The gene product of Rv3367 showed the presence of 39 tandem copies of motif Gly-Gly-Ala/Asn and 43 tandem copies of motif Gly-Gly-X (total 82 repeats) spanning the entire protein except the conserved N-terminal region (FIG. 16). The deduced amino acid sequence encoded by clone AD9 contains 61 repeats of the motifs. Amino acid analysis of Rv3367 by SAPS predicted five other possible repetitive motifs (which are segments of SEQ ID NO:3 as follows):

Gly-Asn-Gly-Gly-Asn-Gly-Gly (residues 188-194),
Gly-Asn-Gly-Gly-Ala-Gly-Gly (residues 207-213),
Asn-Gly-Gly-Ala-Gly-Gly-Asn (residues 279-285),
Gly-Gly-Ala-Gly-Gly-Ala (residues 317-322), and
Gly-Ala-Gly-Gly-Asn-Gly-Gly (residues 204-210)

in the region extending from aa 137-542. The theoretical molecular weight and pI of the protein are 49.7 kDa and 4.05 respectively. This protein has a high content of Gly (38.32%), Ala (16.26%) and Asn (8.97%). The homology search showed 50-55% homology to most of the members of PE-PGRS family of *Mycobacterium tuberculosis* H37Rv. This protein also displayed homology with a glycine rich cell-wall structural protein of *Phasiolus Vulgaris* (42% identity in 483 aa overlap). The Kyte-Dolittle plot demonstrated a hydrophobic region in N-terminal portion of the protein with no repeat motif clusters, and a hydrophilic C-terminal which has the majority of the repeat motifs. A N-terminal signal peptide with a putative signal peptidase cleavage site between aa 44 and 45, and two putative O-glycosylation sites at positions 221 and 438 are predicted to be present in the protein. TMpred analysis predicted five transmembrane helices at aa positions 24-43, 166-186, 194-218, 351-368 and 431-451.

Example XI

Sequence Analyses of Clone AD10

Figure 15C:
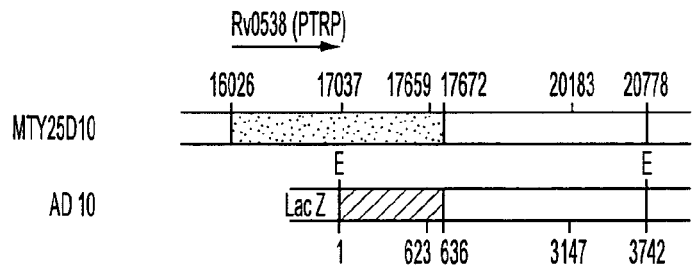

DNA sequence analyses of both ends of EcoR1 insert of clone AD10 (3.7 kb) showed 94% identities to different regions of cosmid MTY25D10. One end of the insert of clone AD10 (nu 1-623) showed homology to nu 17037-17659 and other end (nu 3147-3742) to nu 20183-20778 of cosmid MTY25D10 (FIG. 15C). Restriction map analysis showed that the end of the insert of clone AD10 which is in correct reading frame with β-gal, starts within the gene Rv0538. The peptide expressed in clone AD10 (nu 1-636) represents amino acids 338-548 in the C-terninal region of Rv0538 gene product (FIG. 17). The protein encoded by Rv0538 is a 548 amino acid hypothetical protein with a repetitive proline and threonine-rich region at C-terminal (proline threonine repetitive protein, PTRP). Amino acid analysis of Rv0538 (PTRP) gene product showed the presence of 23 tandem repeats of motif Pro-Pro-Thr-Thr in C-terminal region from position 415 to 495, with positions 2, 3 and 4 being better conserved as compared to position 1. The deduced amino acid sequences encoded by clone AD10 contains all 23 repeats of the motif (FIG. 17). SAPS amino acid analysis of Rv 0538 (PTRP) gene revealed 7 tandem repeats of motif Thr-Thr-Pro-Pro-Thr-Thr-Pro-Pro-Thr-Thr-Pro-Val from aa 413 to 489. The theoretical molecular weight and pI of the protein are 55 kDa and 4.44 respectively.

This protein has a high content of Proline (15.63%), Alanine (15.23%), Threonine (12.83%) and valine (11.42%) with two proline rich regions at aa positions 334-340 and 387-464. No signal peptide appears to be present but four transmembrane helices at aa positions 97-114, 198-218, 278-299 and 379-398 and 50 putative O-glycosylation sites, mostly at C-terminal, are predicted. The Kyte and Doolittle plot shows the presence of seven short hydrophobic regions in the protein. Homology searches showed 100% identity in C-terminal region to a 295 aa (29.4 kD) hypothetical *Mycobacterium bovis* protein and 40% identity in 226 aa overlap to a probable cell wall-plasma membrane linker protein of *Brassica napus*.

Example XII

Sequence Analyses of Clone AD16

Figure 15D:
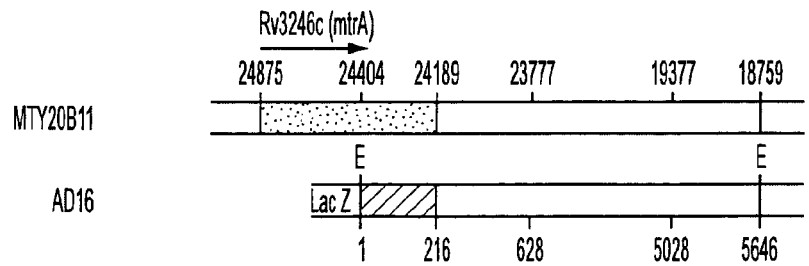

DNA sequence analyses of both ends of EcoR1 insert of clone AD16 (5.6 kb) showed 98% identities to different regions of cosmid MTY20B11. One end of the insert of clone AD16 (nu 1-628) showed homology to nu 24404-23777 and other end (nu5028-5646) showed homology to nu 19377-18759 of cosmid MTY20B11 (FIG. 15D). Restriction map analysis showed that the end of the insert of clone AD16 which is in correct reading frame with β-gal, starts within the gene Rv3246c (mtrA). The peptide expressed in clone AD16 (nu 1-216) represents amino acids 157-228 in the C-terminal region of Rv3246c (mtrA) gene product. The protein encoded by the Rv 3246c is a 228 amino acid MtrA response regulator protein, a putative transcriptional activator, which is identical (100% identity in 225 aa overlap) to previously described response regulator protein MtrA of a putative two-component system, mtrA-mtrB of Mtb H37Rv (44) and similar (55.2% identity in 221aa overlap) to *M. bovis* regX3 [#1838). A homolog of the Mtb MtrA protein was also identified in cell wall fraction of *M. leprae* (30). The theoretical molecular weight and pI of the protein are 25.2 kDa and 5.34 respectively. The Kyte and Doolittle plot showed presence of hydrophobic region in the N-terminal of the protein.

Example XIII

Figure 18A:
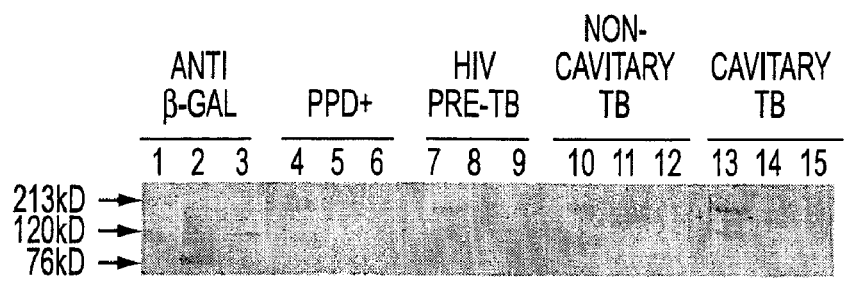
Figure 18B:
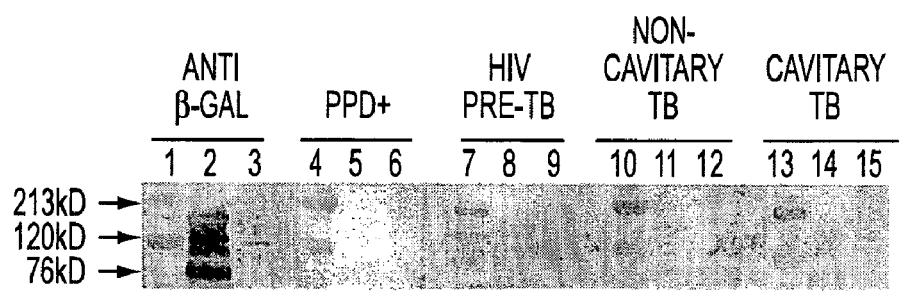
Figure 18C:
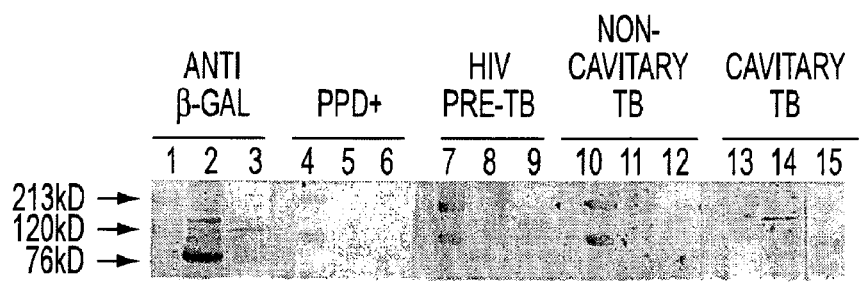
Figure 18D:
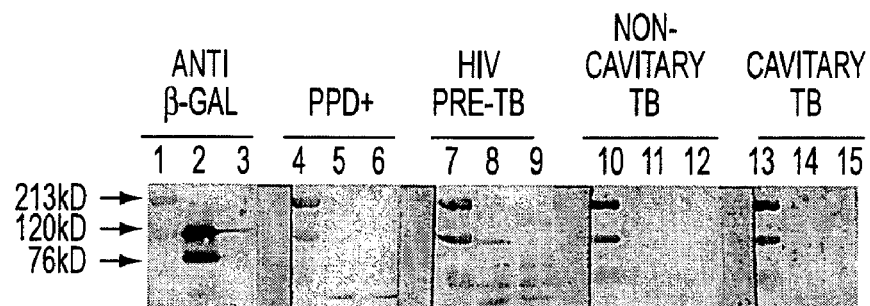

Reactivity of Recombinant Proteins with Sera from Individuals with TB at Different Stages of Disease Progression In order to determine if the antigens identified by sera from aerosol infected rabbits were expressed during human infection with Mtb, their reactivity with sera from TB patients was evaluated. Initially pooled sera from individuals at different stages of disease progression were used. The fusion proteins of PE-PGRS protein (FIG. 18A), the PTRP (FIG. 18B) and the MtrA (FIG. 18C) were strongly reactive with pooled sera from the pre-TB patients. The PE-PGRS protein was also well recognized by the serum pools from non cavitary and the cavitary TB patients (FIG. 18A), but the PTRP and the MtrA fusion proteins showed poorer reactivity with these serum pools (FIGS. 18B and D). In contrast, the pirG (ERP) fusion protein reacted only with the serum pool from the cavitary TB patients (FIG. 18C).

Figure 19C:
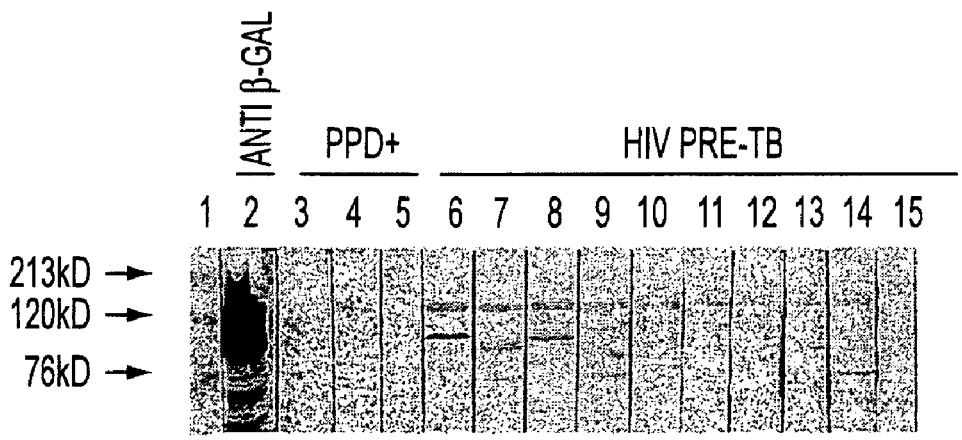

Since the pre-TB serum pools showed reactivity with fusion proteins of three of the four antigens, reactivity with pre-TB sera from 10 individual patients and 3 PPD positive controls was assessed. All 10 pre-TB sera recognized the PE-PGRS (FIG. 19A) and PTRP (FIG. 19B) fusion proteins, whereas 6 of the 10 patients had antibodies to the MtrA fusion protein (FIG. 19C). None of 10 patients showed reactivity with the pirG (ERP) fusion protein when tested individually (data not shown).

Discussion of Examples VI-XIII

The rabbit model of TB closely resembles TB in immunocompetent humans in that both species are outbred, both are relatively resistant to Mtb, and in both the infection may or may not progress to form liquified foci and cavities (6). The paucity of human material available for study of immunological events occurring after inhalation of virulent bacilli necessitates the use of animal models for these studies. The sera used in this study was obtained from rabbits at 5 weeks post-infection because earlier studies have shown that the logarithmic multiplication of inhaled Mtb within the lungs of infected rabbits slows down at about 3 weeks post-infection, and the 4$^{th}$ week onwards, the numbers of cultiviable bacilli decrease (11). Thus, immune responses that can inhibit the intracellular multiplication of inhaled Mtb are first recognized at 4-5 weeks post-infection. Using antibodies in these sera as markers of antigens expressed in vivo, 4 antigens from the Mtb expression library were recognized. Two of these are novel proteins, one is a member of PE-PGRS family of proteins and the other is a protein with proline threonine repeats (PTRP). The other proteins identified in this study, the pirg (ERP), and the MtrA were previously identified by other methodologies, although their role in natural infection and disease progression has not been explored (4, 44).

Interestingly, all four proteins identified by the use of early post-infection sera are either known to be, or have signatures of, surface or secreted proteins of Mtb. Thus, the pirG (ERP) protein has been shown to be a cell surface-exposed protein that is expressed by the bacteria during residence in the phagosomes of in vitro maintained macrophages (3). The cellular location of the Mtb MtrA is not known, but the homolog of MtrA was isolated from cell walls of M. leprae (30). This cell surface location of the Mtb MtrA is consistent with its proposed role as response regulator of a putative two component system mtrA-mtrB (44). The PE-PGRS protein has a hydrophobic N terminal, a putative N-terminal signal peptide and 5 transmembrane regions, suggesting that the protein is either secreted or cell surface associated. The prediction of four transmembrane domains and seven short hydrophobic regions suggests that the PTRP protein is also likely to be a cell surface protein.

Recent analysis of ~4000 open reading frames from the genome sequence to predict their subcellular location showed that in contrast to B. subtilis, Mtb has 4-fold more proteins with extremely basic pIs (42). In contrast, all 4 proteins identified in this study have acidic pIs ranging between 4-5. Since the ERP and the MtrA are known to be expressed during intracellular residence (3, 44), these observations raise the possibility that the PTRP and the PE-PGRS protein identified in this study may also be expressed (or upregulated) under similar conditions. This hypothesis is further strengthened by the observation that pre-TB sera had antibodies to both the proteins. Since the pre-TB sera were obtained from the patients ~6 months prior to clinical manifestation of TB, and since none of these patients had cavitary lesions even at the time of clinical confirmation of TB, the bacteria replication would be intracellular during the pre-TB stage in these patients.

It is also interesting that 3 of the 4 antigens identified in this study are repetitive proteins. Proteins with tandem repetitive motifs are found in several eukaryotic (1, 20, 23, 27, 35) and prokaryotic organisms (13, 16, 17). In fact, a vast majority of gram-positive cell wall associated proteins have tandem repeats of amino acid sequences, which are associated with binding domains for host cell ligands. In many instances, the ability to alter the numbers of the repetitive domains contributes to antigenic variation and to adapting to environmental changes (22). Many of the repetitive proteins are anchored on the cell-wall by the C terminal region containing the LPX-TGX motif, but others that may be anchored by charge and/or hydrophobic interactions have been reported (15). The C-terminal portion of another member of the PE-PGRS family (Rv1759c) of Mtb has recently been shown to bind fibronectin (14), and an M. leprae 21 kD surface protein with 11 repeats of XKKX motif at the C-terminal has been shown to bind the laminin-2 of peripheral nerves, thus facilitating the entry of the bacilli into Schwann cells. (38). In addition, the heparin binding hemagglutinin (HBHA) of Mtb that has been shown to be an adhesin which binds to epithelial cells via the Pro/lys repeats in the C-terminal region (31, 33). The PTRP (Rv 0538) is structurally similar to these proteins in having the repetitive regions clustered in the C-terminal region, suggesting that it may have a similar function.

The PE-PGRS (Rv3367) protein belongs to the PE family of proteins which is one of the two large, clustered multigene families of glycine-rich acidic proteins discovered when the genome sequence of Mtb was determined (9). Some information is now available regarding expression, subcellular location and function of the PE_PGRS family proteins (14, 34). Thus, the fibronectin-binding PE-PGRS protein encoded by Rv 1759c (described above) has been reported to be absent from antigen preparations made from bacteria grown in bacteriological media (14), although the presence of antibodies in patient sera confirm its in vivo expression. Also, PE-PGRS proteins of M. marinum, homologous to Mtb PE-PGRS proteins (Rv3812 and Rv1651c) have been shown to be induced in cultured macrophages as well as in frog granulomas (34). Although, no protein band of the molecular weight corresponding to the PE-PGRS (Rv3367) protein (49 kDa) was observed in the LFCFP and SDS-CW (FIG. 13), whether this protein is really not expressed during in vitro growth, or is expressed very poorly, or is destroyed during the preparation of the LFCFP and the SDS-CWP remains to be determined.

The presence of antibodies in sera from TB patients to all the four proteins identified, and their absence in the sera from PPD positive healthy individuals shows that these proteins are expressed by the in vivo Mtb only during active infection in humans. The mtrA promoter has earlier been shown to be upregulated/activated upon entry and incubation of Mtb in macrophages (44) and the presence of anti MtrA antibodies in pre-TB and non-cavitary TB sera suggests that it is expressed in vivo during intracellular bacterial replication. The β-gal fusion proteins of PE_PGRS and PTRP were also well recognized by the pre-TB sera. We have earlier shown that an 88 kDa culture filtrate protein is recognized by antibodies in the pre-TB sera of about 75% of the HIV-infected TB patients (24). Thus, along with the 88 kDa protein, these 3 proteins may be useful for developing surrogate markers for identifying HIV and Mtb co-infected individuals who are at a high risk of reactivating latent TB. Such markers have the potential to make significant contribution to tuberculosis control in countries with high incidence of co-infection.

Earlier studies have shown that antibodies to the ERP homologs are present in M. bovis infected cattle, and in leprosy patients (5). Our results show that cavitary TB patients have antibodies to β-gal fusion protein of the ERP, but the sera from non-cavitary TB patients and the pre-TB sera did not show reactivity even when individual patients were tested (data not shown). It is possible that in the human tissue environment, this protein is not well-expressed, and therefore is immunogenic only when the bacterial load is high.

In summary, we have identified 4 antigenic proteins of Mtb that are immunodominant during the early phase of an active Mtb infection. All the antigens appear to be surface proteins, and their involvement in bacillary adhesion and/or invasion is currently under investigation. Three of the 4 antigens are potential candidates for devising immunodiagnostic tests for identification of individuals with active, sub-clinical TB. Since many antigens of Mtb, including those that have provided some degree of protection in animal models, have been reported to elicit both cellular and humoral immune responses (2, 12, 19, 43), and since these antigens are expressed in rabbits at the time when cellular immune responses that restrict bacterial growth of the inhaled bacteria are elicited, they are also being studied for their inclusion as components of a subunit vaccine for TB.

References Cited in Examples VI-XIII

1. Allred, D. R., T. C. Mcguire, G. H. Palmer, S. R. Leib, T. M. Harkins, T. F. McElwain, and A. F. Barbet. 1990. Molecular basis for surface antigen size polymorphisms and conservation of a neutralization-sensitive epitope in *Anaplasma marginale*. Proc. Natl. Acad. Sci. 87:3220-3224.
2. Baldwin, S. L., C. d'Souza, A. D. Roberts, B. P. Kelly, A. A. Frank, M. A. Lui, J. B. Ulmer, K. Huygen, D. M. McMurray, and I. M. Orme. 1998. Evaluation of new vaccines in the mouse and guinea pig model of tuberculosis. Infect. Immun. 66:2951-2959.
3. Berthet, F.-X., M. Lagranderie, P. Gounon, C. Laurent-Winter, D. Ensergueix, P. Chavarot, F. Thouron, E. Maranghi, V. Pelicic, D. Portnoi, G. Marchal, and B. Gicquel. 1998. Attenuation of Virulence by Disuption of the *Mycobacterium tuberculosis* erp Gene. Science. 282:759-762.
4. Berthet, F.-X., J. Rauzier, E. M. Lim, W. Philipp, B. Gicquel, and D. Portnoi. 1995. Characterization of the *mycobacterium tuberculosis* erp gene encoding a potential cell surface protein with repetitive structures. Microbiology. 141:2123-2130.
5. Bigi, F., A. Alito, J. C. Fisanotti, M. I. Rornano, and A. Cataldi. 1995. Characterization of a novel *Mycobacterium bovis* secreted antigen containing PGLTS repeats. Infect. Immun. 63:2581-2586.
6. Bishai, W. R., A. M. Dannenberg Jr, N. Parrish, R. Ruiz, P. Chen, B. C. Zook, W. Johnson, J. W. Boles, and M. L. M. Pitt. 1999. Virulence of *Mycobacterium tuberculosis* CDC 1551 and H37RV in Rabbits Evaluated by Lurie's Pulmonary Tubercle Count Method. Infection and Immunity. 67:4931-4934.
7. Cherayil, B. J., and R. A. Young. 1988. A 28 kDa protein from *M. leprae* is the target of the human antibody response in lepromatous leprosy. J. Immunol. 141:4370.
8. Clark-Curtiss, J. E., and J. E. Graham. 1999. Unraveling the secrets of mycobacterial pathogenesis. Thirty-Fourth Tuberculosis-Leprosy Research Conference, San Francisco, Calif.
9. Cole, S. T., R. Brosch, J. Parkhill, T. Garnier, C. Churcher, D. Harris, S. V. Gordon, K. Eiglmeier, S. Gas, C. E. Barry III, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, A. Krogh, J. McLean, S. Moule, L. Murphy, K. Oliver, J. Osborne, M. A. Quail, M. A. Rajandream, J. Rogers, S. Rutter, K. Seegar, J. Skelton, R. Squares, S. squares, J. E. Sulston, K. Taylor, S. Whitehead, and B. G. Barell. 1998. Deciphering the biology of *Mycobacterium tuberculosis* from the complete genome sequence. Nature. 393:537-544.
10. Converse, P. J., J. Arthur M. Dannenberg, J. E. Estep, K. Sugisaki, Y. Abe, B. H. Schofield, and M. L. M. Pitt. 1996. Cavitary tuberculosis produced in rabbits by aerosolized virulent tubercle bacilli. Infect. Immun. 64:4776-4787.
11. Dannenberg, A. M., Jr. 1991. Delayed-type hypersensitivity and cell mediated immunity in the pathogenesis of immunity. Immunol. Today. 12:228-233.
12. Dillon, d. C., M. R. Alderson, C. H. Day, D. Lewinsohn, R. Coler, T. Bement, A. Campos-neto, Y. A. W. Sheiky, I. M. Orme, A. Roberts, S. Steen, W. Dalemans, R. Badaro, and S. G. Reed. 1999. Molecular Characterization and Human T-Cell Responses to a Member of a Novel *Mycobacterium tuberculosis* mtb39 Gene Family. Infect. Immun. 67:2941-2950.
13. Drmsi, S., P. Dehoux, and P. Cossart. 1993. Common features of Gram-positive proteins involved in cell recognition. Mol. Microbiol. 9:1119-1122.
14. Espitia, C., J. P. Laclette, M. Mondragon-Palomino, A. Amador, J. Campuzano, A. Martens, M. Singh, R. Cicero, Y. Zhang, and C. Moreno. 1999. The PE-PGRS glycine-rich proteins of *Mycobacterium tuberculosis*: a new family of fibronectin-binding proteins. Microbiology. 145:3487-3495.
15. Fischetti, V. A. 2000. Surface Proteins on Gram-Positive Bacteria, p. 11-24. In A. S. f. Microbiology (ed.), Gram-Positive Pathogens, Washinton, D.C.
16. Fischetti, V. A., M. Jarymowycz, K. Jones, and J. R. scott. 1986. Streptococcal M protein size mutants occur at high frequency within a single strain. J. Exp. Med. 164:971-980.
17. Gaillard, J. L., P. Berche, C. Frehel, E. Goulin, and P. Cossart. 1991. Entry of L. monocytogenes into cells is mediated by internalin, a repeat protein reminiscent of surface antigens from gram-positive cocci. Cell. 65:1127-1141.
18. Garbe, T. R., N. S. Hibler, and V. Deretic. 1999. Response to reactive nitrogen intermediates in *Mycobacterium tuberculosis*: induction of the 16 kilodalton alpha-crystallin homolog by exposure to nitric oxide donors. Infect. Immun. 67:460-465.
19. Horwitz, M. A., B. W. E. Lee, B. J. Dillon, and G. Harth. 1995. Protective immunity against tuberculosis induced by vaccination with major extracellular proteins of *Mycobacterium tuberculosis*. Proc. Natl. Acad. Sci. USA. 92:1530-1534.
20. Ibanez, C. F., J. L. Affranchino, R. A. Macina, M. B. Reyes, S. Leguizamon, M. E. Camargo, L. Aslund, U. Pettersson, and A. C. C. Frasch. 1988. Multiple *Trypanosoma cruzi* antigens containing tandemly repeated amino acid sequence motifs. Mol. Bio. Parasitol. 30:27-34.
21. Isberg, R. R., and G. Tran Van Nhieu. 1994. Two mammalian cell internalization strategies used by pathogenic bacteria. Annu. Rev. Genet. 27:395-422.
22. Kehoe, M. A. 1984. Cell-Wall-associated proteins in Gram-positve bacteria. In J.-M. Ghuysen and R. Hakenbeck (ed.), Bacterial Cell Wall, vol. Chapter 11. Elsevier Science B.V.
23. Kemp, D. J., R. L. Coppel, and R. F. Anders. 1987. Repetitive proteins and genes of malaria. Ann. Rev. Microbiol. 41:181-208.
24. Laal, S., K. M. Samanich, M. G. Sonnenberg, J. T. Belisle, J. O'Leary, M. S. Simberkoff, and S. Zolla-Pazner. 1997. Surrogate marker of preclinical tuberculosis in human immunodeficiency virus infection: antibodies to an 88 kDa secreted antigen of *Mycobacterium tuberculosis*. J. Infect. Dis. 176:133-143.
25. Laal, S., K. M. Samanich, M. G. Sonnenberg, S. Zolla-Pazner, J. M. Phadtare, and J. T. Belisle. 1996. Human humoral responses to antigens of *Mycobacterium tuberculosis*: immunodominance of high molecular weight antigens. Clin. Diag. Lab. Imunnol. 4:49-56.
26. Lee, B. Y., and M. A. Horwitz. 1995. Identification of macrophage and stress-induced proteins of *Mycobacterium tuberculosis*. J. Clin. Invest. 96:245-249.
27. Longacre, S., U. Hibner, A. Raibaud, H. Eisen, T. Baltz, C. Giroud, and D. Baltz. 1983. DNA rearrangements and antigenic variation in *Trypanosoma equiperdum*: multiple expression-linked sites in independent isolates of Trypanosomes expressing the same antigen. Mol. Cell. Biol. 3:399-409.

28. Lurie, M. Chapter VIII/Host-Parasite Relations in Natively Resistant and Susceptible Rabbits on Quantitive Inhalation of Human and Bovine Tubercle Bacilli, and Nature of Genetic Resistance to Tuberculosis., p. 192-222, Resistance to Tuberculosis; Experimental Studies in native and Acquired Defensive Mechanisms. Harvard University Press, Cambridge, Mass.
29. Lurie, M. B., and A. M. Dannenberg Jr. 1965. Macrophage finction in Infectious Disease with Inbred Rabbits. Bacterial Reviews. 29:466-475.
30. Marques, M. A. M., S. Chitale, P. J. Brennan, and M. C. V. Pessolani. 1998. Mapping and identification of the Major Cell Wall-associated components of *Mycobacterium laprae*. Infect. and Immunity. 66:2625-2631.
31. Menozzi, F. D., R. Bischoff, E. Fort, M. J. Brennan, and C. Locht. 1998. Molecular characterization of the mycobacterial heparin-binding hemagglutinin, a mycobacterial adhesin. Proc. Natl. Acad. Sci. USA. 95:12625-12630.
32. Patti, J. M., B. L. Allen, M. J. McGavin, and M. Hook. 1994. MSCRAMN-Mediated Adherence of Microorganisms to Host Tissues. Annu. Rev. Microbiol. 48:585-617.
33. Pethe, K., M. Aumercier, E. Fort, C. Gatot, C. Locht, and F. D. Menozzi. 2000. Characterization of the Heparin-binding site of the Mycobacterial Heparin-binding Hemagglutinin Adhesin. The Journal of Biological Chemistry. 275:14273-14273.
34. Ramakrishnan, L., N. A. Federspiel, and S. Falkow. 2000. Granuloma-Specific Expression of Mycobacterium Virulence proteins from the glycine-rich PE-PGRS family. Science. 288:1436-1439.
35. Richardson, J. P., R. P. Beecroft, D. L. Tolson, M. K. Liu, and T. W. Pearson. 1988. Procyclin: an unusual immunodominant glycoprotein surface antigen from the procyclic stage of African trypanosomes. Mol. Biochem. Parasitol. 31:203-216.
36. Samanich, K. M., J. T. Belisle, M. G. Sonnenberg, M. A. Keen, S. Zolla-Pazner, and S. Laal. 1998. Delineation of human antibody responses to culture filtrate antigens of *Mycobacterium tuberculosis*. J. Infect. Dis. 178:1534-1538.
37. Sambrook, J., E. F. Fritsch, and T. Maniatis. 1989. Molecular cloning: a laboratory manual. Cold Spring Harbor Laboratory Press, Cold Spring Harbor, N.Y.
38. Shimoji, Y., V. Ng, K. Matsumura, V. A. Fischetti, and A. Rambukkana. 1999. A 21-kDa surface protein of *Mycobacterium leprae* binds peripheral nerve laminin-2 and mediates Schwann cell invasion. Proc. Natl. Acad. Sci. 96:9857-9862.
39. Smith, I., J. Dubnau, R. Manganelli, G. M. Rodriguez, B. Gold, S. Walters, J. Chan, and W. Rom. 1999. Identification and Characterization of Potential Virulence genes of *Mycobacterium tuberculosis*, p. 108-112. US-Japan Cooperative Medical Science Program-Thirty-Fourth Tuberculosis-Leprosy Research Conference, San Francisco-Calif.
40. Smith, I., O. Duserget, M. Rodriquez, J. Timm, M. Gomez, J. Dubnau, B. Gold, and R. manganelli. 1998. Extra and intracellular expression of *Mycobacterium tuberculosis* genes. Tubercle and Lung Disease. 79:91-97.
41. Sonnenberg, M. G., and J. T. Belisle. 1997. Definition of *Mycobacterium tuberculosis* culture filtrate proteins by two-dimensional polyacrylamide gel electrophoresis, N-terminal amino acid sequencing and electrospray mass spectrometry. Infect. Immun. 65:4515-4524.
42. Tekaia, F., S. V. Gordon, T. Garnier, R. Brosch, B. G. Barrell, and S. T. Cole. 1999. Analysis of the proteome of *Mycobacterium tuberculosis* in silico. Tubercle and Lung Disease. 79:329-342.
43. van Vooren, J. P., A. Drowart, M. de Cock, A. van Onckelen, D. H. M. H, J. C. Yernault, C. Valcke, and K. Huygen. 1991. Humoral immune response of tuberculous patients against the three components of the *Mycobacterium bovis* BCG 85 complex separated by isoelectric focusing. J. Clin. Microbiol. 29:2348-2350.
44. Via, L., R. C. M. Mudd, S. Dhandayuthapani, R. Ulmer, and V. Deretic. 1996. Elements of signal transduction in *mycobacterium tuberculosis*: in vitro phosphorylation and in vitro expression of the response regulator MtrA. J. Bacteriology. 178:3314-21.
45. Wong, D. K., B.-Y. Lee, M. A. Horwitz, and B. W. Gibson. 1999. Identification of fur, aconitase, and other proteins expressed by *Mycobacteriurn tuberculosis* under conditions of low and high concentrations of iron by combined two-dimensional gel electrophoresis and mass spectrometry. Infect. Immun. 67:327-336.
46. Young, D. B., and K. Duncan. 1995. Prospects for new interventions in the treatment and prevention of mycobacterial diease. Annu. Rev. Microbiol. 49:641-673.
47. Young, R. A., B. R. Bloom, C. M. Grosskinsky, J. Ivannyi, D. Thomas, and R. W. Davis. 1985. Dissection of *Mycobacterium tuberculosis* antigens using recombinant DNA. Proc. Natl. Acad. Sci. USA. 82:2583-2587.

Example XIV

Definition of *M. tuberculosis* Culture Filtrate Proteins by 2-Dimensional Polyacrylamide Gel Electrophoresis Mapping, N-terminal Amino Acid Sequencing and Electrospray Mass Spectrometry This Example that describes various individual culture filtrate proteins of Mtb is taken from U.S. Pat. No. 6,245,331 (12 Jun. 2001) which, as indicated, is incorporated by reference in its entirety. (See Example V therein)

The combination of 2-D PAGE, western blot analysis, N-terminal amino acid sequencing and liquid chromatography-mass spectrometry-mass spectrometry (LC-MS-MS) was used to develop a detailed map of culture filtrate proteins and to obtained partial amino acid sequences for five previously undefined, relatively abundant proteins within this fraction which are found to be useful as early antigens for serodiagnosis of TB.

These proteins were shown to be early antigens of TB recognized by circulating antibodies in TB patients early in the disease process.

SDS-PAGE and 2-D PAGE of Culture Filtrate Proteins

SDS-PAGE was performed under reducing conditions by the method of Laemmli with gels (7.5×10 cm×0.75 mm) containing a 6% stack over a 15% resolving gel. Each gel was run at 10 mA for 15 min followed by 15 mA for 1.5 h.

2-D PAGE separation of proteins was achieved by the method of O'Farrell with minor modifications. Specifically, 70 µg of CFP was dried and suspended in 30 µl of isoelectric focusing (IEF) sample buffer [9 M urea, 2% Nonidet P-40, 5% βmercaptoethanol, and 5% ampholytes pH 3-10 (Pharmalytes; Pharmacia Biotech, Piscataway, N.J.)], and incubated for 3 h at 20° C. An aliquot of 25 µg of protein was applied to a 6% polyacrylamide IEF tube gel (1.5 mm by 6.5 cm) containing 5% Pharmalytes pH 3-10 and 4-6.5 in a ratio of 1:4. The proteins were focused for 3 h at 1 kV using 10 mM $H_3PO_4$ and 20 mM NaOH as the catholyte and anolyte, respectively. The tube gels were subsequently imbibed in sample transfer buffer for 30 min and placed on a preparative SDS-polyacrylamide gel (7.5×10 cm×1.5 mm) containing a 6% stack over a 15% resolving gel. Electrophoresis in the second dimension was carried out at 20 mA per gel for 0.3 h followed by 30 mA per gel for 1.8 h. Proteins were visualized by staining with silver nitrate.

Silver stained 2-D PAGE gels were imaged using a cooled CCD digitizing camera and analyzed with MicroScan 1000 2-D Gel Analysis Software for Windows 3.x (Technology Resources, Inc., Nashville, Tenn.). Protein peak localization and analysis was conducted with the spot filter on, a minimum allowable peak height of 1.0, and minimum allowable peak area of 2.0.

Proteins, subjected to 2-D or SDS-PAGE, were transferred to nitrocellulose membranes (Schleicher and Schuell, Keene, N.H.) which were blocked with 0.1% bovine serum albumin in 0.05 M Tris-HCl, pH 7.5, 0.15 M NaCl, and 0.05% Tween 80 (TBST). These membranes were incubated for 2 h with specific antibodies diluted with TBST to the proper working concentrations. After washing, the membranes were incubated for 1 h with goat anti-mouse or -rabbit alkaline phosphatase-conjugated antibody (Sigma) diluted in TBST. The substrates nitro-blue-tetrazolium and 5-bromo-4-chloro-3-indoyl phosphate (BCIP) were used for color development.

Mapping of proteins reactive to specific antibodies within the 2-D PAGE gel was accomplished using 0.1% India ink as a secondary stain for the total protein population after detection by immunoblotting. Alternatively, the Digoxigenin (DIG) Total Protein/Antigen Double Staining Kit (Boehringer Mannheim, Indianapolis, Ind.) was employed for those antibody-reactive proteins that could not be mapped using India ink as the secondary stain. Briefly, after electroblotting, the membranes were washed three times in 0.05 M $K_2HPO_4$, pH 8.5. The total protein population was conjugated to digoxigenin by incubating the membrane for one hour at room temperature in a solution of 0.05 M $K_2HPO_4$, pH 8.5 containing 0.3 ng/ml digoxigenin-3-0-methylcarbonyl-$\epsilon$-amino-caproic acid N-hydroxysuccinimide ester and 0.01% Nonidet-P40. The membranes were subsequently blocked with a solution of 3% bovine serum albumin in 0.05 M Tris-HCl, pH 7.5, 0.15 M NaCl (TBS) for 1 h followed by washing with TBS. Incubation with specific antibodies was performed as described, followed by incubation of the membranes with mouse anti-DIG-Fab fragments conjugated to alkaline phosphatase diluted 1:2000 in TBS, for 1 h. The membranes were washed three times with TBS and probed with goat anti-mouse or -rabbit horse radish peroxidase-conjugated antibody. Color development for the proteins reacting to the specific anti-Mtb protein antibodies was obtained with the substrates 4-(1,4,7,10-tetraoxadecyl)-1-naphthol and 1.8% $H_2O_2$. Secondary color development of the total protein population labeled with digoxigenin utilized BCIP and [2-(4-iodophenyl)-3-(4-nitrophenyl)-5-phenyl-tetrazolium chloride] as the substrates.

To obtain N-terminal amino acid sequence for selected proteins, CFPs (200 µg) were resolved by 2-D PAGE and transferred to polyvinylidene difluoride membrane (Millipore, Milford, Mass.) by electroblotting at 50 V for 1 h, using CAPS buffer with 10% methanol. The membrane was stained with 0.1% Coomassie brilliant blue in 10% acetic acid and destained with a solution of 50% methanol and 10% acetic acid. Immobilized proteins were subjected to automated Edman degradation on a gas phase sequencer equipped with a continuous-flow reactor. The phenylthiohydantoin amino acid derivatives were identified by on-line reversed-phase chromatography as described previously.

Selected CFP were subjected to LC-MS-MS to determine the sequence of internal peptide fragments. CFPs (200 mg) were resolved by 2-D PAGE and the gel stained with 0.1% Coomassie brilliant blue and destained as described for proteins immobilized to PVDF membranes. The protein of interest was excised from the gel, washed several times with distilled water to remove residual acetic acid and subjected to in-gel proteolytic digestion with trypsin. Peptides were eluted from the acrylamide and separated by C18 capillary RP-HPLC. The microcapillary RP-HPLC effluent was introduced directly into a Finnigan-MAT (San Jose, Calif.) TSQ-700 triple sector quadrupole mass spectrometer. Mass spectrometry and analysis of the data was performed as described by Blyn et al.

C. Results

1. Definition of Proteins Present in the Culture Filtrate of Mtb H37Rv.

Through the efforts of the World Health Organization (WHO) Scientific Working Groups (SWGs) on the Immunology of Leprosy (IMMLEP) and Immunology of Tuberculosis (IMMTUB) an extensive collection of mAbs against mycobacterial proteins has been established. This library as well as mAbs and polyclonal sera not included in these collections allowed for the identification of known mycobacterial proteins in the culture filtrate of Mt. A detailed search of the literature identified mAbs and/or polyclonal sera reactive against 35 individual Mtb CFP (Table 1). Initially, the presence or absence of these proteins in the culture filtrate of Mtb H37Rv, prepared for these studies, was determined by Western blot analyses. Of the antibodies and sera tested, all but one (IT-56) demonstrated reactivity to specific proteins of this preparation (Table 1). The mAb IT-56 is specific for the 65 kDa Mtb GroEL homologue; a protein primarily associated with the cytosol. Additionally the mAb IT-7 reacted with a 14 kDa and not a 40 kDa CFP.

2. 2-D PAGE Mapping of Known CFP of Mtb H37Rv

Using 2-D western blot analysis coupled with secondary staining (either India ink or Dig total protein/antigen double staining) the proteins reactive to specific mAbs or polyclonal sera were mapped within the 2-D PAGE profile of CFP of Mtb H37Rv. In all, 32 of the reactive antibodies detected specific proteins resolved by 2-D PAGE (Table 1). However, two antibodies (IT-1 and IT-46), that were reactive by conventional western blot analysis, failed to detect any protein within the 2-D profile (not shown; summarized in Tables). This lack of reactivity by 2-D western analysis, presumably, was due to the absence of linear epitopes exposed by the denaturing conditions used to resolve molecules for conventional Western blot analyses.

The majority of the antibodies recognized a single protein spot. However, several (IT-3, IT-4, IT-7, IT-20, IT-23, IT-41, IT-42, IT-44, IT-49, IT-57, IT-58, IT-61 and MPT 32) reacted with multiple proteins. Five of these, IT-23, IT-42, IT-44, IT-57 and IT-58 reacted with protein clusters centered at 36 kDa, 85 kDa, 31 kDa, 85 kDa and 50 kDa, respectively. Additionally the proteins in each of these clusters migrated within a narrow pI range; suggesting that the antibodies were reacting with multiple isoforms of their respective proteins. In the case of the protein cluster at 85 kDa (which is the "88 kDa" identified as malate synthase) detected by IT-57, the most dominant component of this cluster was also recognized by IT-42.

Polyclonal sera against MPT 32 recognized a 45 and 42 kDa protein of relatively similar pI. While defining sites of glycosylation on MPT 32 (see above) we observed that this protein was prone to autoproteolysis and formed a 42 kDa product. Thus, the 42 kDa protein detected with the anti-MPT 32 sera was a breakdown product of the 45 kDa MPT 32 glycoprotein. The mAb (T-49 specific for the Antigen 85 (Ag85) complex clearly identified the three gene products (Ag85A, B and C) of this complex. The greatest region of antibody cross-reactivity was at molecular masses below 16 kDa. The most prominent protein in this region reacted with mAb IT-3 specific for the 14 kDa GroES homolog. This mAb also recognized several adjacent proteins at approximately 14 kDa. Interestingly, various members of this same protein cluster reacted with anti-MPT 57 and anti-MPT 46 polyclonal sera, and the mAbs IT-4, IT-7, and IT-20.

3. N-terminal Amino Acid Sequencing of Selected CFPs

The N-terminal amino acid sequences or complete gene sequences and functions of several of the CFPs of Mt, mapped with the available antibodies, are known. However, such information is lacking for the proteins that reacted with IT-42 IT-43, IT-44, IT-45, IT-51, IT-52, IT-53, IT-57, IT-59 and IT-69, as well as several dominant proteins not identified by these means. Of these, the most abundant proteins (IT-52, IT-57, IT 42, IT-58 and proteins labeled A-K) were selected and subjected to N-terminal amino acid sequencing.

TABLE 1

Reactivity of CFPs of *M. tuberculosis* $H_{37}Rv$ to reported specific mAbs and polyclonal antisera

| Antibody[1] | MW (kDa) | Dilution Used | REACTIVITY 1-D | 2-D |
|---|---|---|---|---|
| IT-1 (F23-49-7) | 16 kDa | 1:2000 | + | − |
| IT-3 (SA-12) | 12 kDa | 1:8000 | + | + |
| IT-4 (F24-2-3) | 16 kDa | 1:2000 | + | + |
| IT-7 (F29-29-7) | 40 kDa | 1:1000 | + | + |
| IT-10 (F29-47-3) | 21 kDa | 1:1000 | + | + |
| IT-12 (HYT6) | 17-19 kDa | 1:50 | + | + |
| IT-17 (D2D) | 23 kDa | 1:8000 | + | + |
| IT-20 (WTB68-A1) | 14 kDa | 1:250 | + | + |
| IT-23 (WTB71-H3) | 38 kDa | 1:250 | + | + |
| IT-40 (HAT1) | 71 kDa | 1:50 | + | + |
| IT-41 (HAT3) | 71 kDa | 1:50 | + | + |
| IT-42 (HBT1) | 82 kDa | 1:50 | + | + |
| IT-43 (HBT3) | 56 kDa | 1:50 | + | + |
| IT-44 (HBT7) | 32 kDa | 1:50 | + | + |
| IT-45 (HBT8) | 96 kDa | 1:50 | + | + |
| IT-46 (HBT10) | 40 kDa | 1:50 | + | − |
| IT-49 (HYT27) | 32-33 kDa | 1:50 | + | + |
| IT-51 (HBT2) | 17 kDa | 1:50 | + | + |
| IT-52 (HBT4) | 25 kDa | 1:50 | + | + |
| IT-53 (HBT5) | 96 kDa | 1:50 | + | + |
| IT-56 (CBA1) | 65 kDa | 1:50 | − | ND* |
| IT-57 (CBA4) | 82 kDa | 1:50 | + | + |
| IT-58 (CBA5) | 47 kDa | 1:50 | + | + |
| IT-59 (F67-1) | 33 kDa | 1:100 | + | + |
| IT-61 (F116-5) | 30 (24) kDa | 1:100 | + | + |
| IT-67 (L24.b4) | 24 kDa | 1:50 | + | + |
| IT-69 (HBT 11) | 20 kDa | 1:6 | + | + |
| F126-2 | 30 kDa | 1:100 | + | + |
| A3h4 | 27 kDa | 1:50 | + | + |
| HYB 76-8 | 6 kDa | 1:100 | + | + |
| anti-MPT 32 | 50 kDa | 1:100 | + | + |
| anti-MPT 46 | 10 kDa | 1:100 | + | + |
| anti-MPT 53 | 15 kDa | 1:100 | + | + |
| anti-MPT 57 | 12 kDa | 1:100 | + | + |
| anti-MPT 63 - K64 | 18 kDa | 1:200 | + | + |

*ND: Not done
[1]Original designations for the World Health Organization cataloged Mab are given in parentheses.

Three of these proteins were found to correspond to previously defined products. The N-terminal amino acid sequence of the protein labeled D was identical to that of Ag85 B and C. This result was unexpected given that the IT-49 mAb failed to detect this protein and N-terminal amino acid analysis confirmed that those proteins reacting with IT-49 were members of the Ag85 complex. Second, the protein labeled E had an N-terminal sequence identical to that of glutamine synthetase. A third protein which reacted with IT-52 was found to be identical to MPT 51.

However, five of the proteins analyzed appeared to be novel. Three of these, those labeled B, C and IT-58 did not demonstrate significant homology to any known mycobacterial or prokaryotic sequences. The protein labeled I possessed an N-terminal sequence with 72% identity to the amino terminus of an α-hydroxysteroid dehydrogenase from a *Eubacterium* species, and the protein labeled F was homologous to a deduced amino acid sequence for an open reading frame identified in the Mtb cosmid MTCY1A11. Repeated attempts to sequence those proteins labeled as A, G, H, J, K, IT-43, IT-44, IT-49 and IT-57 were unsuccessful.

Reactivity of Tuberculosis Sera with the *M. tuberculosis* 88 kDa Antigen

A high molecular weight fraction of CFP of Mtb reacted with a preponderance of sera from TB patients and that this fraction was distinguished from other native fractions in that it possessed the product initially thought to be reactive to mAb IT-57. In view of this, the protein cluster (the 88 kDa protein) initially thought to be defined by IT-42 and IT-57 was excised from a 2-D polyacrylamide gel, digested with trypsin and the resulting peptides analyzed by LC-MS-MS. In order to confirm that *M. tuberculosis* also contains a seroreactive 88 kDa antigen which is not the catalase/peroxidase, a katG-negative strain of *M. tuberculosis* (ATCC 35822) was tested. Lysates from this strain failed to react with any of the anti-catalase/peroxidase antibodies However, when individual sera from healthy controls and TB patients of all three groups were tested with the same lysates, all the group III and group IV sera reacted with the 88 kDa protein Identification of the Amino Acid Sequence of the Sero-Reactive 88 kDa Protein The culture filtrate protein from a katG-negative strain of *M. tuberculosis* (ATCC 35822) was resolved as above by 2-D PAGE. The protein spot corresponding to the sero-reactive 88 kDa protein was cut out of the gel and subject to an in-gel digestion with trypsin. The resulting tryptic peptides were extracted, applied to a $C_{18}$ RP-HPLC column, and eluted with an increasing concentration of acetonitrile. The peptides eluted in this manner were introduced directly into a Finnigan LCQ Electrospray mass spectrometer. The molecular mass of each peptide was determined, as was the charge state, with a zoom-scan program. Identification of the 88 kDa protein was achieved by entering the mass spectroscopy date obtained above into the MS-Fit computer program and searching it against the *M. tuberculosis* database.

The protein was identified as GlcB (Z78020) of *M. tuberculosis*, which is believed to be the enzyme malate synthase based on sequence homology to known proteins of other bacteria This protein has the Accession number CAB01465 on the NCBI Genbank database (based on Cole, S. T. et al., Nature 393:537-544 (1998), which describes the complete genome sequence of *M. tuberculosis*). The sequence of this protein, SEQ ID NO: 13 is presented below.

C. Discussion

In contrast to Mtb cell wall, cell membrane and cytoplasmic proteins, the CFPs are well defined in terms of function, immunogenicity and composition. However, a detailed analysis of the total proteins, and the molecular definition and 2-D PAGE mapping of the majority of these CFPs has not been performed. Nagai and colleagues identified and mapped by 2-D PAGE the most abundant proteins filtrate harvested after five weeks of culture in Sauton medium. The present study used culture filtrates from mid- to late-logarithmic cultures of three Mtb type strains H37Ra, H37Rv, and Erdman to provide for the first time a detailed analysis understanding of this widely studied fraction.

Computer analysis of the 2-D gels of CFP resolved 205, 203 and 206 individual protein spots from filtrates of strains H37Rv, H37Ra and Erdman, respectively. Of the total spots, 37 were identified using a collection of mAb and polyclonal sera against CFPs. Several of these antibodies recognized more than one spot; several are believed to react with multiple isoforms of the same protein or were previously shown to recognize more then a single gene product. In all, partial or complete amino acid sequences have been reported for 17 of the proteins mapped with the available antibodies.

For greater molecular definition, a number of abundant products observed in the 2-D PAGE were subjected to N-terminal sequence analysis.

One such protein that migrated between Ag85B and Ag85C was found to have 16 residues (FSRPGLPVEYLQVPSP, [SEQ ID NO:12]) identical to the N-terminus of mature Ag85A and Ag85B, and different from Ag85C by a single residue (position 15). This protein spot was apparently merely a homologue of Ag85A or B. However, its complete lack of reactivity with an Ag85-specific mAb (IT-49), its weight greater than that of Ag85B and its shift in pI in relation to Ag85A suggested that this product may have resulted from post translational modifications. Alternatively, this protein may be a yet unrecognized fourth member of the Ag85 complex. However, members of the Ag85 complex appear to lack post-translational modifications in some reports whereas others report several bands corresponding to Ag85C after isoelectric focusing. However, no direct evidence supports the existence of a fourth Ag85 product.

A second product sequenced was a 25 kDa protein with a pI of 5.34. Its N-terminal sequence (XPVM/LVXPGXEXX-QDN, [SEQ ID NO:15]) showed homology to an internal fragment (DPVLVFPGMEIRQDN, [SEQ ID NO: 16]) corresponding to open reading frame 28c of the Mtb cosmid MTCY1A11. Analysis of that deduced sequence revealed a signal peptidase I consensus sequence (Ala-Xaa-Ala) and an apparent signal peptide preceding the N-terminus of the 25 kDa protein sequenced above N-terminal sequencing of selected CFPs identified three novel products:

(I) protein with 72% identity to the N-terminus of a 42 kDa α-hydroxysteroid dehydrogenase of *Eubacterium* sp. VPI 12708;

(2) 27 kDa protein previously defined as MPT-51; and (3) 56 kDa protein previously identified as glutamine synthetase.

Three proteins showed no significant homology between their N-termini and any known peptides. For these proteins and for others that were refractory to N-group analysis, more advanced methods of protein sequencing (e.g., LC-MS-MS) will permit acquisition of extended sequence information.

This type of broad survey of virulent Mtb strains has led to, and will continue to allow, the identification of immunologically important proteins and will lead to identification of novel virulence factors leading to improved approaches to chemotherapy. Thus, not only does the present invention enhance the overall knowledge in the art of the physiology of Mtb, but it also provides immediate tools for early serodiagnosis.

TABLE 2

Summary of certain protein spots detected by computer aided analysis of silver nitrate stained 2-D gels.

| Ref #. | H37Rv | H37Ra | Erdman | MW(kDa) | pI | Antibody Reactivity | Function/ Designation | N-terminal Sequence | SEQ ID NO |
|---|---|---|---|---|---|---|---|---|---|
| 11 | 11 | 11 | 11 | 38.90 | 4.31 | anti-MPT 32 | MPT 32 | DPAPAPPVPT | 9 |
| 14 | 14 | 14 | 14 | 42.17 | 4.51 | anti-MPT 32 | MPT 32 | DPAPAPPVPT | 9 |
| 24 | 24 | 24 | 24 | 48.70 | 4.79 | | | | |
| 59 | 59 | 59 | 59 | 29.68 | 5.08 | | | | |
| 66 | 66 | 66 | 66 | 35.69 | 5.09 | IT-23 | PstS | CGSKPPSPET | 10 |
| 68 | 68 | 68 | 68 | 42.41 | 5.10 | | | | |
| 69 | 69 | 69 | 69 | 30.20 | 5.10 | | | | |
| 77 | 77 | 77 | 77 | 28.18 | 5.10 | | | | |
| 80 | 80 | 80 | 80 | 42.17 | 5.10 | | C | XXAVXVT | 11 |
| 103 | 103 | 103 | 103 | 31.08 | 5.12 | | D: Antigen 85 Homolog? | FSRPGLPVEYLQVPSP | 12 |
| 111 | 111 | 111 | 111 | 104.71 | 5.13 | | | | |
| 124 | 124 | 124 | 124 | 85.11 (88) | 5.19 | | Malate synthase | See below for full sequencel | 13 |
| 170 | 170 | 170 | 170 | 26.92 | 5.91 | IT-52 | MPT 51 | See below for full sequence | 14 |

Amino Acid Sequence of 88 kDa Malate Synthase (SEQ ID NO: 13):

```
MTDRVSVGNL RIARVLYDFV NNEALPGTDI DPDSFWAGVD KVVADLTPQN QALLNARDEL QAQIDKWHRR RVIEPIDMDA

YRQFLTEIGY LLPEPDDFTI TTSGVDAEIT TTAGPQLVVP VLNARFALNA ANARWGSLYD ALYGTDVIPE TDGAEKGPTY

NKVRGDKVIA YARKFLDDSV PLSSGSFGDA TGFTVQDGQL VVALPDKSTG LANPGQFAGY TGAAESPTSV LLINHGLHIE

ILIDPESQVG TTDRAGVKDV ILESAITTIM DFEDSVAAVD AADKVLGYRN WLGLNKGDLA AAVDKDGTAF LRVLNRDRNY

TAPGGGQFTL PGRSLMFVRN VGHLMTNDAI VDTDGSEVFE GIMDALFTGL IAIHGLKASD VNGPLINSRT GSIYIVKPKM

HGPAEVAFTC ELFSRVEDVL GLPQNTMKIG IMDEERRTTV NLKACIKAAA DRVVFINTGF LDRTGDEIHT SMEAGPMVRK

GTMKSQPWIL AYEDHNVDAG LAAGFSGRAQ VGKGMWTMTE LMADMVETKI AQPRAGASTA WVPSPTAATL HALHYHQVDV

AAVQQGLAGK RRATIEQLLT IPLAKELAWA PDEIREEVDN NCQSILGYVV RWVDQGVGCS KVPDIHDVAL MEDRATLRIS
```

```
SQLLANWLRH  GVITSADVRA  SLERMAPLVD  RQNAGDVAYR  PMAPNFDDSI  AFLAAQELIL  SGAQQPNGYT  EPILHRRRRE

FKARAAEKPA  PSDRAGDDAA  R
```

Amino Acid Sequence of Secreted Form of MPT 51 (SEQ ID NO:14):

```
APYENLMVPS  PSMGRDIPVA  FLAGGPHAVY  LLDAFNAGPD  VSNWVTAGNA  NTLAGKGIS  VVAPAGGAYS  MYTNWEQDGS

KQWDTFLSAE  LPDWLAANRG  AAQGGYGAMA  AAFHPDRFG   FAGSMSGFLY  PSNTTTNGAI  AAGMQQFGGV  DTNGMWGAPQ

LGRWKWHDPW  HASLLAQNN   TRVWVWSPTN  PGASDPAAMI  GQTAEAMGNS  RMFYNQYRSV  GGHNGHFDFP  SGDNGWGSW

APQLGAMSGD  IVGAIR.
```

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

---

SEQUENCE LISTING

```
<160> NUMBER OF SEQ ID NOS: 16

<210> SEQ ID NO 1
<211> LENGTH: 450
<212> TYPE: PRT
<213> ORGANISM: Mycobacterium tuberculosis

<400> SEQUENCE: 1

Met Asn Phe Pro Val Leu Pro Pro Glu Ile Asn Ser Val Leu Met Tyr
1               5                   10                  15

Ser Gly Ala Gly Ser Ser Pro Leu Leu Ala Ala Ala Ala Trp Asp
            20                  25                  30

Gly Leu Ala Glu Glu Leu Gly Ser Ala Ala Val Ser Phe Gly Gln Val
            35                  40                  45

Thr Ser Gly Leu Thr Ala Gly Val Trp Gln Gly Ala Ala Ala Ala
        50                  55                  60

Met Ala Ala Ala Ala Pro Tyr Ala Gly Trp Leu Gly Ser Val Ala
65                  70                  75                  80

Ala Gln Ala Val Ala Val Ala Gly Gln Ala Arg Ala Ala Val Ala Ala
                85                  90                  95

Phe Glu Ala Ala Leu Ala Ala Thr Val Asp Pro Ala Ala Val Ala Val
                100                 105                 110

Asn Arg Met Ala Met Arg Ala Leu Ala Met Ser Asn Leu Leu Gly Gln
            115                 120                 125

Asn Ala Ala Ala Ile Ala Ala Val Glu Ala Glu Tyr Glu Leu Met Trp
        130                 135                 140

Ala Ala Asp Val Ala Ala Met Ala Gly Tyr His Ser Gly Ala Ser Ala
145                 150                 155                 160

Ala Ala Ala Ala Leu Pro Ala Phe Ser Pro Pro Ala Gln Ala Leu Gly
                165                 170                 175
```

-continued

```
Gly Gly Val Gly Ala Phe Leu Asn Ala Leu Phe Ala Gly Pro Ala Lys
            180                 185                 190

Met Leu Arg Leu Asn Ala Gly Leu Gly Asn Val Gly Asn Tyr Asn Val
        195                 200                 205

Gly Leu Gly Asn Val Gly Ile Phe Asn Leu Gly Ala Ala Asn Val Gly
    210                 215                 220

Ala Gln Asn Leu Gly Ala Ala Asn Ala Gly Ser Gly Asn Phe Gly Phe
225                 230                 235                 240

Gly Asn Ile Gly Asn Ala Asn Phe Gly Phe Gly Asn Ser Gly Leu Gly
                245                 250                 255

Leu Pro Pro Gly Met Gly Asn Ile Gly Leu Gly Asn Ala Gly Ser Ser
            260                 265                 270

Asn Tyr Gly Leu Ala Asn Leu Gly Val Gly Asn Ile Gly Phe Ala Asn
        275                 280                 285

Thr Gly Ser Asn Asn Ile Gly Ile Gly Leu Thr Gly Asp Asn Leu Thr
    290                 295                 300

Gly Ile Gly Gly Leu Asn Ser Gly Thr Gly Asn Leu Gly Leu Phe Asn
305                 310                 315                 320

Ser Gly Thr Gly Asn Ile Gly Phe Phe Asn Ser Gly Thr Gly Asn Phe
                325                 330                 335

Gly Val Phe Asn Ser Gly Ser Tyr Asn Thr Gly Val Gly Asn Ala Gly
            340                 345                 350

Thr Ala Ser Thr Gly Leu Phe Asn Val Gly Gly Phe Asn Thr Gly Val
        355                 360                 365

Ala Asn Val Gly Ser Tyr Asn Thr Gly Ser Phe Asn Ala Gly Asn Thr
    370                 375                 380

Asn Thr Gly Gly Phe Asn Pro Gly Asn Val Asn Thr Gly Trp Leu Asn
385                 390                 395                 400

Thr Gly Asn Thr Asn Thr Gly Ile Ala Asn Ser Gly Asn Val Asn Thr
                405                 410                 415

Gly Ala Phe Ile Ser Gly Asn Phe Ser Asn Gly Val Leu Trp Arg Gly
            420                 425                 430

Asp Tyr Glu Gly Leu Trp Gly Leu Ser Gly Gly Ser Thr Ile Pro Ala
        435                 440                 445

Ile Pro
    450

<210> SEQ ID NO 2
<211> LENGTH: 857
<212> TYPE: PRT
<213> ORGANISM: Mycobacterium tuberculosis

<400> SEQUENCE: 2

Ser Val Thr Ile Pro Ala Leu Thr Ala Ala Arg Ala Val Leu Asp Met
1               5                   10                  15

Ala Ala Ser Val Gly Ala Thr Ser Glu Ile Glu Pro Phe Ile Val Trp
            20                  25                  30

Thr Ser Ser Gly Ala Ile Gly Pro Thr Trp Tyr Ser Val Gly Arg Ile
        35                  40                  45

Tyr Asn Ala Gly Asp Leu Phe Val Gly Gly Asn Ile Ile Ser Gly Ile
    50                  55                  60

Pro Thr Leu Ser Thr Thr Gly Pro Val His Ala Val Phe Asn Ala Ala
65                  70                  75                  80

Ser Gln Ala Phe Asn Thr Pro Ala Leu Asn Ile His Gln Ile Pro Leu
```

-continued

```
                 85                  90                  95
Gly Phe Gln Val Pro Gly Ser Ile Asp Ala Ile Thr Leu Phe Pro Gly
            100                 105                 110
Gly Leu Thr Phe Pro Ala Asn Ser Leu Leu Asn Leu Asp Val Phe Val
            115                 120                 125
Gly Thr Pro Gly Ala Thr Ile Pro Ala Ile Thr Phe Pro Glu Ile Pro
            130                 135                 140
Ala Asn Ala Asp Gly Glu Leu Tyr Val Ile Ala Gly Asp Ile Pro Leu
145                 150                 155                 160
Ile Asn Ile Pro Pro Thr Pro Gly Ile Gly Asn Thr Thr Val Pro
                165                 170                 175
Ser Ser Gly Phe Phe Asn Thr Gly Ala Gly Gly Ser Gly Phe Gly
            180                 185                 190
Asn Phe Gly Ala Asn Met Ser Gly Trp Trp Asn Gln Ala His Thr Ala
            195                 200                 205
Leu Ala Gly Ala Gly Ser Gly Ile Ala Asn Val Gly Thr Leu His Ser
            210                 215                 220
Gly Val Leu Asn Leu Gly Ser Gly Leu Ser Gly Ile Tyr Asn Thr Ser
225                 230                 235                 240
Thr Leu Pro Leu Gly Thr Pro Ala Leu Val Ser Gly Leu Gly Asn Val
                245                 250                 255
Gly Asp His Leu Ser Gly Leu Leu Ala Ser Asn Val Gly Gln Asn Pro
            260                 265                 270
Ile Thr Ile Val Asn Ile Gly Leu Ala Asn Val Gly Asn Gly Asn Val
            275                 280                 285
Gly Leu Gly Asn Ile Gly Asn Leu Asn Leu Gly Ala Ala Asn Ile Gly
            290                 295                 300
Asp Val Asn Leu Gly Phe Gly Asn Ile Gly Asp Val Asn Leu Gly Phe
305                 310                 315                 320
Gly Asn Ile Gly Gly Asn Val Gly Phe Gly Asn Ile Gly Asp Ala
            325                 330                 335
Asn Phe Gly Phe Gly Asn Ser Gly Leu Ala Ala Gly Leu Ala Gly Met
            340                 345                 350
Gly Asn Ile Gly Leu Gly Asn Ala Gly Ser Gly Asn Val Gly Trp Ala
            355                 360                 365
Asn Met Gly Leu Gly Asn Ile Gly Phe Gly Asn Thr Gly Thr Asn Asn
            370                 375                 380
Leu Gly Ile Gly Leu Thr Gly Asp Asn Gln Ser Gly Ile Gly Gly Leu
385                 390                 395                 400
Asn Ser Gly Thr Gly Asn Ile Gly Leu Phe Asn Ser Gly Thr Gly Asn
                405                 410                 415
Ile Gly Phe Phe Asn Ser Gly Thr Ala Asn Phe Gly Leu Phe Asn Ser
            420                 425                 430
Gly Ser Tyr Asn Thr Gly Ile Gly Asn Ser Gly Val Ala Ser Thr Gly
            435                 440                 445
Leu Val Asn Ala Gly Gly Phe Asn Thr Gly Val Ala Asn Ala Gly Ser
            450                 455                 460
Tyr Asn Thr Gly Ser Phe Asn Ala Gly Asp Thr Asn Thr Gly Gly Phe
465                 470                 475                 480
Asn Pro Gly Ser Thr Asn Thr Gly Trp Phe Asn Thr Gly Asn Ala Asn
                485                 490                 495
Thr Gly Val Ala Asn Ala Gly Asn Val Asn Thr Gly Ala Leu Ile Thr
            500                 505                 510
```

Gly Asn Phe Ser Asn Gly Ile Leu Trp Arg Gly Asn Tyr Glu Gly Leu
            515                 520                 525

Ala Gly Phe Ser Phe Gly Tyr Pro Ile Pro Leu Phe Pro Ala Val Gly
        530                 535                 540

Ala Asp Val Thr Gly Asp Ile Gly Pro Ala Thr Ile Ile Pro Pro Ile
545                 550                 555                 560

His Ile Pro Ser Ile Pro Leu Gly Phe Ala Ala Ile Gly His Ile Gly
            565                 570                 575

Pro Ile Ser Ile Pro Asn Ile Ala Ile Pro Ser Ile His Leu Gly Ile
        580                 585                 590

Asp Pro Thr Phe Asp Val Gly Pro Ile Thr Val Asp Pro Ile Thr Leu
            595                 600                 605

Thr Ile Pro Gly Leu Ser Leu Asp Ala Ala Val Ser Glu Ile Arg Met
        610                 615                 620

Thr Ser Gly Ser Ser Gly Phe Lys Val Arg Pro Ser Phe Ser Phe
625                 630                 635                 640

Phe Ala Val Gly Pro Asp Gly Met Pro Gly Gly Glu Val Ser Ile Leu
            645                 650                 655

Gln Pro Phe Thr Val Ala Pro Ile Asn Leu Asn Pro Thr Thr Leu His
        660                 665                 670

Phe Pro Gly Phe Thr Ile Pro Thr Gly Pro Ile His Ile Gly Leu Pro
            675                 680                 685

Leu Ser Leu Thr Ile Pro Gly Phe Thr Ile Pro Gly Gly Thr Leu Ile
        690                 695                 700

Pro Gln Leu Pro Leu Gly Leu Gly Leu Ser Gly Gly Thr Pro Pro Phe
705                 710                 715                 720

Asp Leu Pro Thr Val Val Ile Asp Arg Ile Pro Val Glu Leu His Ala
            725                 730                 735

Ser Thr Thr Ile Gly Pro Val Ser Leu Pro Ile Phe Gly Phe Gly Gly
        740                 745                 750

Ala Pro Gly Phe Gly Asn Asp Thr Thr Ala Pro Ser Ser Gly Phe Phe
            755                 760                 765

Asn Thr Gly Gly Gly Gly Ser Gly Phe Ser Asn Ser Gly Ser Gly
        770                 775                 780

Met Ser Gly Val Leu Asn Ala Ile Ser Asp Pro Leu Leu Gly Ser Ala
785                 790                 795                 800

Ser Gly Phe Ala Asn Phe Gly Thr Gln Leu Ser Gly Ile Leu Asn Arg
            805                 810                 815

Gly Ala Gly Ile Ser Gly Val Tyr Asn Thr Gly Thr Leu Gly Leu Val
        820                 825                 830

Thr Ser Ala Phe Val Ser Gly Phe Met Asn Val Gly Gln Gln Leu Ser
            835                 840                 845

Gly Leu Leu Phe Ala Gly Thr Gly Pro
        850                 855

<210> SEQ ID NO 3
<211> LENGTH: 1767
<212> TYPE: DNA
<213> ORGANISM: Mycobacterium tuberculosis
<220> FEATURE:
<221> NAME/KEY: CDS
<222> LOCATION: (1)..(1764)
<223> OTHER INFORMATION:

<400> SEQUENCE: 3

-continued

| | |
|---|---|
| atg tcg ttt gtc gta gca gtc ccg gag gca ttg gcg gcg gcc gcg tcg<br>Met Ser Phe Val Val Ala Val Pro Glu Ala Leu Ala Ala Ala Ala Ser<br>1               5                   10                  15 | 48 |
| gat gtg gcg aac atc ggt tct gcg cta agt gcc gcg aat gca gcg gca<br>Asp Val Ala Asn Ile Gly Ser Ala Leu Ser Ala Ala Asn Ala Ala Ala<br>        20                  25                  30 | 96 |
| gcc gcc ggc aca acg ggg cta ctg gca gcc ggt gcc gac gag gtc tcg<br>Ala Ala Gly Thr Thr Gly Leu Leu Ala Ala Gly Ala Asp Glu Val Ser<br>    35                  40                  45 | 144 |
| gcc gcc ctg gcg tcg ctg ttt tcc ggg cac gct gtg agc tac caa cag<br>Ala Ala Leu Ala Ser Leu Phe Ser Gly His Ala Val Ser Tyr Gln Gln<br>50                  55                  60 | 192 |
| gtc gcg gcc cag gcg acg gcg tta cac gat cag ttt gtc cag gcc ttg<br>Val Ala Ala Gln Ala Thr Ala Leu His Asp Gln Phe Val Gln Ala Leu<br>65                  70                  75                  80 | 240 |
| acc ggt gcc ggc gga tcg tac gcc ctc acc gag gcc gcc aac gtc cag<br>Thr Gly Ala Gly Gly Ser Tyr Ala Leu Thr Glu Ala Ala Asn Val Gln<br>                85                  90                  95 | 288 |
| cag aat ctg ctg aac gca att aac gcg ccc act cag gcg ctg ttg ggg<br>Gln Asn Leu Leu Asn Ala Ile Asn Ala Pro Thr Gln Ala Leu Leu Gly<br>            100                 105                 110 | 336 |
| cgc ccg tta att ggc gac ggg gct gtc ggc acc gcc agc agc ccc gac<br>Arg Pro Leu Ile Gly Asp Gly Ala Val Gly Thr Ala Ser Ser Pro Asp<br>        115                 120                 125 | 384 |
| ggg caa gat ggc ggt ctg ctg ttc ggc aac ggg ggc gcc ggc tac aac<br>Gly Gln Asp Gly Gly Leu Leu Phe Gly Asn Gly Gly Ala Gly Tyr Asn<br>    130                 135                 140 | 432 |
| agc gcc gcc acg ccc gga atg gcc ggc ggc aac ggc ggc aac gcc gga<br>Ser Ala Ala Thr Pro Gly Met Ala Gly Gly Asn Gly Gly Asn Ala Gly<br>145                 150                 155                 160 | 480 |
| ttg atc ggc aac ggc ggt act ggc ggg tcg ggc ggt gcc ggc gcg gcc<br>Leu Ile Gly Asn Gly Gly Thr Gly Gly Ser Gly Gly Ala Gly Ala Ala<br>                165                 170                 175 | 528 |
| ggt ggc gcc ggc ggc agc ggc ggc tgg ttg tac ggc aac ggc gga aac<br>Gly Gly Ala Gly Gly Ser Gly Gly Trp Leu Tyr Gly Asn Gly Gly Asn<br>            180                 185                 190 | 576 |
| ggc ggc atc ggc ggg aat gcg atc gtc gcg ggc ggt gcc ggc ggc aat<br>Gly Gly Ile Gly Gly Asn Ala Ile Val Ala Gly Gly Ala Gly Gly Asn<br>        195                 200                 205 | 624 |
| ggg ggc gct ggc ggc gcc gcc gga ttg tgg ggc agt ggc ggc agc ggc<br>Gly Gly Ala Gly Gly Ala Gly Leu Trp Gly Ser Gly Gly Ser Gly<br>    210                 215                 220 | 672 |
| ggc caa ggc ggc aac ggt ctg acc ggc aac gac ggc gtg aat ccg gcc<br>Gly Gln Gly Gly Asn Gly Leu Thr Gly Asn Asp Gly Val Asn Pro Ala<br>225                 230                 235                 240 | 720 |
| ccc gtc aca aac ccc gcg cta aat ggc gcc gcc ggc gac agc aat atc<br>Pro Val Thr Asn Pro Ala Leu Asn Gly Ala Ala Gly Asp Ser Asn Ile<br>                245                 250                 255 | 768 |
| gag ccg caa acc agc gtc ctg atc ggc acc caa ggc ggt gac ggc acg<br>Glu Pro Gln Thr Ser Val Leu Ile Gly Thr Gln Gly Gly Asp Gly Thr<br>            260                 265                 270 | 816 |
| ccc ggg ggt gct ggc gtc aac ggc ggc aac ggt ggc gcg ggc gga gac<br>Pro Gly Gly Ala Gly Val Asn Gly Gly Asn Gly Gly Ala Gly Gly Asp<br>        275                 280                 285 | 864 |
| gcc aat ggc aac ccc gca aac acc tcg atc gcc aac gca ggc gcc ggc<br>Ala Asn Gly Asn Pro Ala Asn Thr Ser Ile Ala Asn Ala Gly Ala Gly<br>    290                 295                 300 | 912 |
| ggg aac ggc gcc gcc ggc ggt gac ggc ggt gcc aat ggc ggt gcg ggc<br>Gly Asn Gly Ala Ala Gly Gly Asp Gly Gly Ala Asn Gly Gly Ala Gly<br>305                 310                 315                 320 | 960 |

```
ggc gcc ggc ggg cag gcc gcg tcc gcc ggt agt tcc gtc ggc ggt gac      1008
Gly Ala Gly Gly Gln Ala Ala Ser Ala Gly Ser Ser Val Gly Gly Asp
                325                 330                 335 ggc ggc aac ggc ggt gcc ggc ggt acg ggc acg aac ggg cac gcc ggc      1056
Gly Gly Asn Gly Gly Ala Gly Gly Thr Gly Thr Asn Gly His Ala Gly
            340                 345                 350 ggt gcg ggc ggc gcc ggc ggt gcc ggt ggt cgc ggc ggg tgg ctg gtc      1104
Gly Ala Gly Gly Ala Gly Gly Ala Gly Gly Arg Gly Gly Trp Leu Val
        355                 360                 365 ggc aac ggt ggc aac ggt ggc aac ggt gcc gcc ggc ggc aac ggc gcc      1152
Gly Asn Gly Gly Asn Gly Gly Asn Gly Ala Ala Gly Gly Asn Gly Ala
    370                 375                 380 atc ggc ggt acc ggt ggt gcc ggc ggt gtc ccc gcc aac cag ggc ggt      1200
Ile Gly Gly Thr Gly Gly Ala Gly Gly Val Pro Ala Asn Gln Gly Gly
385                 390                 395                 400 aac agc gcc cta ggc acc cag ccg gtc ggc ggc gac ggc ggc gac ggc      1248
Asn Ser Ala Leu Gly Thr Gln Pro Val Gly Gly Asp Gly Gly Asp Gly
                405                 410                 415 ggc aac ggg ggc acc gga ggc acc ggg cgt ggc ggc gac ggc gga          1296
Gly Asn Gly Gly Thr Gly Gly Thr Gly Gly Arg Gly Gly Asp Gly Gly
            420                 425                 430 tcc ggc ggc gcg ggc ggc gcg agc ggt tgg ttg atg ggc aac ggc ggc      1344
Ser Gly Gly Ala Gly Gly Ala Ser Gly Trp Leu Met Gly Asn Gly Gly
        435                 440                 445 aac ggc ggc aac ggc ggc acc ggc ggc tca ggc ggt gtc ggc ggc aat      1392
Asn Gly Gly Asn Gly Gly Thr Gly Gly Ser Gly Gly Val Gly Gly Asn
    450                 455                 460 ggc ggc atc ggc ggt gac ggc gcc ggc ggc gga aac gcc acg agc acg      1440
Gly Gly Ile Gly Gly Asp Gly Ala Gly Gly Asn Ala Thr Ser Thr
465                 470                 475                 480 tcg agc atc ccc ttc gac gcc cac ggg ggt aac ggc ggc gct ggt ggc      1488
Ser Ser Ile Pro Phe Asp Ala His Gly Gly Asn Gly Gly Ala Gly Gly
                485                 490                 495 gac gct ggt cac ggc gga acg ggc ggc gac ggc ggt gac ggg ggg cat      1536
Asp Ala Gly His Gly Gly Thr Gly Gly Asp Gly Gly Asp Gly Gly His
            500                 505                 510 gcc ggc acc ggt gga cgt ggc ggg tta ctg gcc ggc cag cac gcc aac      1584
Ala Gly Thr Gly Gly Arg Gly Gly Leu Leu Ala Gly Gln His Ala Asn
        515                 520                 525 tcc ggc aat ggc ggt ggc ggc ggt acc ggc ggt gcc ggg ggc acc cat      1632
Ser Gly Asn Gly Gly Gly Gly Gly Thr Gly Gly Ala Gly Gly Thr His
    530                 535                 540 ggc acc ccc ggc agc ggc aac gca ggc ggc acc ggc acc ggt aac gct      1680
Gly Thr Pro Gly Ser Gly Asn Ala Gly Gly Thr Gly Thr Gly Asn Ala
545                 550                 555                 560 gac agc aca aac ggc ggg cca ggc agc gac ggc ctc ggc ggg gac gcg      1728
Asp Ser Thr Asn Gly Gly Pro Gly Ser Asp Gly Leu Gly Gly Asp Ala
                565                 570                 575 ttt aac ggc agt cgc ggc acc gac ggc aac ccc ggc taa                  1767
Phe Asn Gly Ser Arg Gly Thr Asp Gly Asn Pro Gly
            580                 585

<210> SEQ ID NO 4
<211> LENGTH: 588
<212> TYPE: PRT
<213> ORGANISM: Mycobacterium tuberculosis

<400> SEQUENCE: 4

Met Ser Phe Val Val Ala Val Pro Glu Ala Leu Ala Ala Ala Ala Ser
1               5                   10                  15
```

```
Asp Val Ala Asn Ile Gly Ser Ala Leu Ser Ala Asn Ala Ala
             20                  25                  30

Ala Ala Gly Thr Thr Gly Leu Leu Ala Ala Gly Ala Asp Glu Val Ser
         35                  40                  45

Ala Ala Leu Ala Ser Leu Phe Ser Gly His Ala Val Ser Tyr Gln Gln
 50                  55                  60

Val Ala Ala Gln Ala Thr Ala Leu His Asp Gln Phe Val Gln Ala Leu
 65                  70                  75                  80

Thr Gly Ala Gly Gly Ser Tyr Ala Leu Thr Glu Ala Ala Asn Val Gln
                 85                  90                  95

Gln Asn Leu Leu Asn Ala Ile Asn Ala Pro Thr Gln Ala Leu Leu Gly
             100                 105                 110

Arg Pro Leu Ile Gly Asp Gly Ala Val Gly Thr Ala Ser Ser Pro Asp
         115                 120                 125

Gly Gln Asp Gly Gly Leu Leu Phe Gly Asn Gly Ala Gly Tyr Asn
     130                 135                 140

Ser Ala Ala Thr Pro Gly Met Ala Gly Gly Asn Gly Gly Asn Ala Gly
145                 150                 155                 160

Leu Ile Gly Asn Gly Gly Thr Gly Gly Ser Gly Gly Ala Gly Ala Ala
                 165                 170                 175

Gly Gly Ala Gly Gly Ser Gly Gly Trp Leu Tyr Gly Asn Gly Gly Asn
         180                 185                 190

Gly Gly Ile Gly Gly Asn Ala Ile Val Ala Gly Gly Ala Gly Gly Asn
         195                 200                 205

Gly Gly Ala Gly Gly Ala Ala Gly Leu Trp Gly Ser Gly Gly Ser Gly
         210                 215                 220

Gly Gln Gly Gly Asn Gly Leu Thr Gly Asn Asp Gly Val Asn Pro Ala
225                 230                 235                 240

Pro Val Thr Asn Pro Ala Leu Asn Gly Ala Ala Gly Asp Ser Asn Ile
                 245                 250                 255

Glu Pro Gln Thr Ser Val Leu Ile Gly Thr Gln Gly Gly Asp Gly Thr
             260                 265                 270

Pro Gly Gly Ala Gly Val Asn Gly Gly Asn Gly Gly Ala Gly Gly Asp
         275                 280                 285

Ala Asn Gly Asn Pro Ala Asn Thr Ser Ile Ala Asn Ala Gly Ala Gly
         290                 295                 300

Gly Asn Gly Ala Ala Gly Gly Asp Gly Gly Ala Asn Gly Gly Ala Gly
305                 310                 315                 320

Gly Ala Gly Gly Gln Ala Ala Ser Ala Gly Ser Ser Val Gly Gly Asp
             325                 330                 335

Gly Gly Asn Gly Gly Ala Gly Gly Thr Gly Thr Asn Gly His Ala Gly
         340                 345                 350

Gly Ala Gly Gly Ala Gly Gly Ala Gly Gly Arg Gly Gly Trp Leu Val
         355                 360                 365

Gly Asn Gly Gly Asn Gly Gly Asn Gly Ala Ala Gly Gly Asn Gly Ala
         370                 375                 380

Ile Gly Gly Thr Gly Gly Ala Gly Gly Val Pro Ala Asn Gln Gly Gly
385                 390                 395                 400

Asn Ser Ala Leu Gly Thr Gln Pro Val Gly Gly Asp Gly Gly Asp Gly
                 405                 410                 415

Gly Asn Gly Gly Thr Gly Gly Thr Gly Gly Arg Gly Gly Asp Gly Gly
             420                 425                 430
```

```
Ser Gly Gly Ala Gly Gly Ala Ser Gly Trp Leu Met Gly Asn Gly Gly
        435                 440                 445

Asn Gly Gly Asn Gly Gly Thr Gly Gly Ser Gly Gly Val Gly Gly Asn
    450                 455                 460

Gly Gly Ile Gly Gly Asp Gly Ala Gly Gly Asn Ala Thr Ser Thr
465                 470                 475                 480

Ser Ser Ile Pro Phe Asp Ala His Gly Asn Gly Gly Ala Gly Gly
                485                 490                 495

Asp Ala Gly His Gly Gly Thr Gly Gly Asp Gly Gly Asp Gly Gly His
            500                 505                 510

Ala Gly Thr Gly Gly Arg Gly Gly Leu Leu Ala Gly Gln His Ala Asn
        515                 520                 525

Ser Gly Asn Gly Gly Gly Gly Thr Gly Gly Ala Gly Gly Thr His
    530                 535                 540

Gly Thr Pro Gly Ser Gly Asn Ala Gly Gly Thr Gly Thr Gly Asn Ala
545                 550                 555                 560

Asp Ser Thr Asn Gly Gly Pro Gly Ser Asp Gly Leu Gly Gly Asp Ala
                565                 570                 575

Phe Asn Gly Ser Arg Gly Thr Asp Gly Asn Pro Gly
            580                 585

<210> SEQ ID NO 5
<211> LENGTH: 1647
<212> TYPE: DNA
<213> ORGANISM: Mycobacterium tuberculosis
<220> FEATURE:
<221> NAME/KEY: CDS
<222> LOCATION: (1)..(1644)
<223> OTHER INFORMATION:

<400> SEQUENCE: 5 atg gac gtc gct ttg ggg gtt gcg gtc acg gat cgg gtc gcg cgt ctg      48
Met Asp Val Ala Leu Gly Val Ala Val Thr Asp Arg Val Ala Arg Leu
1               5                   10                  15 gcg ctg gtc gac tcg gct gcg ccc ggc acc gtg atc gac cag ttc gtg      96
Ala Leu Val Asp Ser Ala Ala Pro Gly Thr Val Ile Asp Gln Phe Val
                20                  25                  30 ctc gat gtg gcc gag cac ccg gtc gag gtg tta acc gag acc gtg gtg     144
Leu Asp Val Ala Glu His Pro Val Glu Val Leu Thr Glu Thr Val Val
            35                  40                  45 ggc acg gat cgg tca ttg gcc ggc gaa aac cac cgg ctg gtc gct acc     192
Gly Thr Asp Arg Ser Leu Ala Gly Glu Asn His Arg Leu Val Ala Thr
        50                  55                  60 cgg ctg tgt tgg ccg gat cag gcc aaa gct gac gag ctg cag cac gca     240
Arg Leu Cys Trp Pro Asp Gln Ala Lys Ala Asp Glu Leu Gln His Ala
65                  70                  75                  80 ctg cag gac tcc ggg gtc cac gac gtt gcc gtg ata tcc gag gcg cag     288
Leu Gln Asp Ser Gly Val His Asp Val Ala Val Ile Ser Glu Ala Gln
                85                  90                  95 gcc gcc acg gcg ctg gtc ggg gcg gca cat gcc ggc tct gcc gtg ctg     336
Ala Ala Thr Ala Leu Val Gly Ala Ala His Ala Gly Ser Ala Val Leu
            100                 105                 110 ttg gtg ggt gat gag acg gca acc tta tcg gtg gtt ggt gac ccg gac     384
Leu Val Gly Asp Glu Thr Ala Thr Leu Ser Val Val Gly Asp Pro Asp
        115                 120                 125 gcg ccg ccg acg atg gtg gcc gtc gcg ccg gtg gcg ggc gcc gac gcc     432
Ala Pro Pro Thr Met Val Ala Val Ala Pro Val Ala Gly Ala Asp Ala
    130                 135                 140 aca tcg acc gtc gat acc ctg atg gcc cgg ctc ggc gac cag gcc ctc     480
```

```
                Thr Ser Thr Val Asp Thr Leu Met Ala Arg Leu Gly Asp Gln Ala Leu
                145                 150                 155                 160 gcc ccg ggg gat gtc ttc ctg gtg ggt agg tcc gcc gag cac acc acg           528
Ala Pro Gly Asp Val Phe Leu Val Gly Arg Ser Ala Glu His Thr Thr
                    165                 170                 175 gtt ctt gcc gac cag ctg cgc gcg tcg acg atg cgc gtg cag act               576
Val Leu Ala Asp Gln Leu Arg Ala Ser Thr Met Arg Val Gln Thr
            180                 185                 190 ccc gac gac ccc acg ttc gcg ctg gcc cgt ggc gcg gcg atg gcg gcc           624
Pro Asp Asp Pro Thr Phe Ala Leu Ala Arg Gly Ala Ala Met Ala Ala
            195                 200                 205 ggc gcc gct acg atg gcg cac ccg gcc ctg gtc gcg gat gcg acc act           672
Gly Ala Ala Thr Met Ala His Pro Ala Leu Val Ala Asp Ala Thr Thr
        210                 215                 220 tcg ctc ccc cgg gcc gag gcg ggg caa tcg ggt tct gaa ggc gag cag           720
Ser Leu Pro Arg Ala Glu Ala Gly Gln Ser Gly Ser Glu Gly Glu Gln
225                 230                 235                 240 ctg gcg tac tcg cag gcc agc gat tac gag ctg ctt ccg gtc gac gaa           768
Leu Ala Tyr Ser Gln Ala Ser Asp Tyr Glu Leu Leu Pro Val Asp Glu
                245                 250                 255 tat gag gaa cac gac gaa tac ggg gca gcc gcg gat cgc tcg gcg ccg           816
Tyr Glu Glu His Asp Glu Tyr Gly Ala Ala Ala Asp Arg Ser Ala Pro
            260                 265                 270 ttg agc cga cgg tcg ctg ctg atc ggc aac gct gtc gtg gcc ttt gcg           864
Leu Ser Arg Arg Ser Leu Leu Ile Gly Asn Ala Val Val Ala Phe Ala
            275                 280                 285 gtg atc ggt ttc gcc tcg ctg gcg gtg gcg gtg gcg gtc acc atc cga           912
Val Ile Gly Phe Ala Ser Leu Ala Val Ala Val Ala Val Thr Ile Arg
290                 295                 300 ccg acc gcg gcc tca aaa ccg gta gag gga cac caa aac gcc cag cca           960
Pro Thr Ala Ala Ser Lys Pro Val Glu Gly His Gln Asn Ala Gln Pro
305                 310                 315                 320 ggg aag ttc atg ccg ttg ttg ccg acg caa cag cag gcg ccg gtc ccg          1008
Gly Lys Phe Met Pro Leu Leu Pro Thr Gln Gln Gln Ala Pro Val Pro
                325                 330                 335 ccg cct ccg ccc gat gat ccc acc gct gga ttc cag ggc ggc acc att          1056
Pro Pro Pro Pro Asp Asp Pro Thr Ala Gly Phe Gln Gly Gly Thr Ile
            340                 345                 350 ccg gct gta cag aac gtg gtg ccg cgg ccg ggt acc tca ccc ggg gtg          1104
Pro Ala Val Gln Asn Val Val Pro Arg Pro Gly Thr Ser Pro Gly Val
        355                 360                 365 ggt ggg acg ccg gct tcg cct gcg ccg gaa gcg ccg gcc gtg ccc ggt          1152
Gly Gly Thr Pro Ala Ser Pro Ala Pro Glu Ala Pro Ala Val Pro Gly
    370                 375                 380 gtt gtg cct gcc ccg gtg cca atc ccg gtc ccg atc atc att ccc ccg          1200
Val Val Pro Ala Pro Val Pro Ile Pro Val Pro Ile Ile Ile Pro Pro
385                 390                 395                 400 ttc ccg ggt tgg cag cct gga atg ccg acc atc ccc acc gca ccg ccg          1248
Phe Pro Gly Trp Gln Pro Gly Met Pro Thr Ile Pro Thr Ala Pro Pro
                405                 410                 415 acg acg ccg gtg acc acg tcg gcg acg acg ccg acc acg ccg ccg              1296
Thr Thr Pro Val Thr Thr Ser Ala Thr Thr Pro Thr Thr Pro Pro
            420                 425                 430 acc acg ccg gtg acc acg ccg cca acg acg ccg acc acg ccg gtg              1344
Thr Thr Pro Val Thr Thr Pro Pro Thr Thr Pro Thr Thr Pro Val
        435                 440                 445 acc acg ccg cca acg acg ccg ccg acc acg ccg gtg acc acg cca cca          1392
Thr Thr Pro Pro Thr Thr Pro Pro Thr Thr Pro Val Thr Thr Pro Pro
    450                 455                 460
```

```
acg acc gtc gcc ccg acg acc gtc gcc ccg acg acg gtc gct ccg acc    1440
Thr Thr Val Ala Pro Thr Thr Val Ala Pro Thr Thr Val Ala Pro Thr
465                 470                 475                 480 acc gtc gcc ccg acc acg gtc gct cca gcc acc gcc acg ccg acg acc    1488
Thr Val Ala Pro Thr Thr Val Ala Pro Ala Thr Ala Thr Pro Thr Thr
            485                 490                 495 gtc gct ccg cag ccg acg cag cag ccc acg caa caa cca acc caa cag    1536
Val Ala Pro Gln Pro Thr Gln Gln Pro Thr Gln Gln Pro Thr Gln Gln
500                 505                 510 atg cca acc cag cag cag acc gtg gcc ccg cag acg gtg gcg ccg gct    1584
Met Pro Thr Gln Gln Gln Thr Val Ala Pro Gln Thr Val Ala Pro Ala
        515                 520                 525 ccg cag ccg ccg tcc ggt ggc cgc aac ggc agc ggc ggg ggc gac tta    1632
Pro Gln Pro Pro Ser Gly Gly Arg Asn Gly Ser Gly Gly Gly Asp Leu
    530                 535                 540 ttc ggc ggg ttc tga                                                1647
Phe Gly Gly Phe
545

<210> SEQ ID NO 6
<211> LENGTH: 548
<212> TYPE: PRT
<213> ORGANISM: Mycobacterium tuberculosis

<400> SEQUENCE: 6

Met Asp Val Ala Leu Gly Val Ala Val Thr Asp Arg Val Ala Arg Leu
1               5                   10                  15

Ala Leu Val Asp Ser Ala Ala Pro Gly Thr Val Ile Asp Gln Phe Val
            20                  25                  30

Leu Asp Val Ala Glu His Pro Val Glu Val Leu Thr Glu Thr Val Val
        35                  40                  45

Gly Thr Asp Arg Ser Leu Ala Gly Glu Asn His Arg Leu Val Ala Thr
    50                  55                  60

Arg Leu Cys Trp Pro Asp Gln Ala Lys Ala Asp Glu Leu Gln His Ala
65                  70                  75                  80

Leu Gln Asp Ser Gly Val His Asp Val Ala Val Ile Ser Glu Ala Gln
            85                  90                  95

Ala Ala Thr Ala Leu Val Gly Ala Ala His Ala Gly Ser Ala Val Leu
        100                 105                 110

Leu Val Gly Asp Glu Thr Ala Thr Leu Ser Val Val Gly Asp Pro Asp
    115                 120                 125

Ala Pro Pro Thr Met Val Ala Val Ala Pro Val Ala Gly Ala Asp Ala
130                 135                 140

Thr Ser Thr Val Asp Thr Leu Met Ala Arg Leu Gly Asp Gln Ala Leu
145                 150                 155                 160

Ala Pro Gly Asp Val Phe Leu Val Gly Arg Ser Ala Glu His Thr Thr
            165                 170                 175

Val Leu Ala Asp Gln Leu Arg Ala Ala Ser Thr Met Arg Val Gln Thr
        180                 185                 190

Pro Asp Asp Pro Thr Phe Ala Leu Ala Arg Gly Ala Ala Met Ala Ala
    195                 200                 205

Gly Ala Ala Thr Met Ala His Pro Ala Leu Val Ala Asp Ala Thr Thr
210                 215                 220

Ser Leu Pro Arg Ala Glu Ala Gly Gln Ser Gly Ser Glu Gly Glu Gln
225                 230                 235                 240

Leu Ala Tyr Ser Gln Ala Ser Asp Tyr Glu Leu Leu Pro Val Asp Glu
            245                 250                 255
```

```
Tyr Glu Glu His Asp Glu Tyr Gly Ala Ala Ala Asp Arg Ser Ala Pro
            260                 265                 270

Leu Ser Arg Arg Ser Leu Leu Ile Gly Asn Ala Val Val Ala Phe Ala
        275                 280                 285

Val Ile Gly Phe Ala Ser Leu Ala Val Ala Val Ala Val Thr Ile Arg
    290                 295                 300

Pro Thr Ala Ala Ser Lys Pro Val Glu Gly His Gln Asn Ala Gln Pro
305                 310                 315                 320

Gly Lys Phe Met Pro Leu Leu Pro Thr Gln Gln Gln Ala Pro Val Pro
                325                 330                 335

Pro Pro Pro Pro Asp Asp Pro Thr Ala Gly Phe Gln Gly Gly Thr Ile
                340                 345                 350

Pro Ala Val Gln Asn Val Val Pro Arg Pro Gly Thr Ser Pro Gly Val
                355                 360                 365

Gly Gly Thr Pro Ala Ser Pro Ala Pro Glu Ala Pro Ala Val Pro Gly
            370                 375                 380

Val Val Pro Ala Pro Val Pro Ile Pro Val Pro Ile Ile Ile Pro Pro
385                 390                 395                 400

Phe Pro Gly Trp Gln Pro Gly Met Pro Thr Ile Pro Thr Ala Pro Pro
                405                 410                 415

Thr Thr Pro Val Thr Thr Ser Ala Thr Thr Pro Thr Thr Pro Pro
            420                 425                 430

Thr Thr Pro Val Thr Thr Pro Pro Thr Thr Pro Pro Thr Thr Pro Val
            435                 440                 445

Thr Thr Pro Pro Thr Thr Pro Pro Thr Thr Pro Val Thr Thr Pro Pro
450                 455                 460

Thr Thr Val Ala Pro Thr Thr Val Ala Pro Thr Thr Val Ala Pro Thr
465                 470                 475                 480

Thr Val Ala Pro Thr Thr Val Ala Pro Ala Thr Ala Thr Pro Thr Thr
                485                 490                 495

Val Ala Pro Gln Pro Thr Gln Gln Pro Thr Gln Gln Pro Thr Gln Gln
                500                 505                 510

Met Pro Thr Gln Gln Thr Val Ala Pro Gln Thr Val Ala Pro Ala
            515                 520                 525

Pro Gln Pro Pro Ser Gly Gly Arg Asn Gly Ser Gly Gly Asp Leu
            530                 535                 540

Phe Gly Gly Phe
545

<210> SEQ ID NO 7
<211> LENGTH: 9
<212> TYPE: PRT
<213> ORGANISM: Mycobacterium tuberculosis
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
```

<400> SEQUENCE: 7

Asn Xaa Gly Xaa Gly Xaa Asn Xaa Gly
1               5

<210> SEQ ID NO 8
<211> LENGTH: 473
<212> TYPE: PRT
<213> ORGANISM: Mycobacterium tuberculosis

<400> SEQUENCE: 8

Met Thr Glu Phe Asp Asp Ile Lys Asn Leu Ser Leu Pro Glu Thr Arg
1               5                   10                  15

Asp Ala Ala Lys Gln Leu Leu Asp Ser Val Ala Gly Asp Leu Thr Gly
            20                  25                  30

Glu Ala Ala Gln Arg Phe Gln Ala Leu Thr Arg His Ala Glu Glu Leu
        35                  40                  45

Arg Ala Glu Gln Arg Arg Gly Arg Glu Ala Glu Ala Leu Arg
    50                  55                  60

Arg Tyr Arg Ala Gly Glu Leu Arg Val Val Pro Gly Ala Pro Thr Gly
65                  70                  75                  80

Gly Asp Asp Gly Asp Ala Pro Pro Gly Asn Ser Leu Arg Asp Thr Ala
                85                  90                  95

Phe Arg Thr Leu Asp Ser Cys Val Arg Asp Gly Leu Met Ser Ser Arg
            100                 105                 110

Ala Ala Glu Thr Ala Glu Thr Leu Cys Arg Thr Gly Pro Pro Gln Ser
        115                 120                 125

Thr Ser Trp Ala Gln Arg Trp Leu Ala Ala Thr Gly Ser Arg Asp Tyr
    130                 135                 140

Leu Gly Ala Phe Val Lys Arg Val Ser Asn Pro Val Ala Gly His Thr
145                 150                 155                 160

Val Trp Thr Asp Arg Glu Ala Ala Trp Arg Glu Ala Ala Ala Val
                165                 170                 175

Ala Ala Glu Gln Arg Ala Met Gly Leu Val Asp Thr Gln Gly Gly Phe
        180                 185                 190

Leu Ile Pro Ala Ala Leu Asp Pro Ala Ile Leu Leu Ser Gly Asp Gly
    195                 200                 205

Ser Thr Asn Pro Ile Arg Gln Val Ala Arg Val Gln Thr Thr Ser
210                 215                 220

Glu Ile Trp Arg Gly Val Thr Ser Glu Gly Ala Glu Ala Arg Trp Tyr
225                 230                 235                 240

Ser Glu Ala Gln Glu Val Ser Asp Asp Ser Pro Ala Leu Ala Gln Pro
                245                 250                 255

Ala Val Pro Asn Tyr Arg Gly Ser Cys Trp Ile Pro Phe Ser Ile Glu
            260                 265                 270

Leu Glu Gly Asp Ala Ala Ser Phe Val Gly Glu Ile Gly Lys Ile Leu
        275                 280                 285

Ala Asp Ser Val Glu Gln Leu Gln Ala Ala Phe Val Asn Gly Ser
    290                 295                 300

Gly Asn Gly Glu Pro Thr Gly Phe Val Ser Ala Leu Thr Gly Thr Ser
305                 310                 315                 320

Asp Gln Val Val Val Gly Ala Gly Ser Glu Ala Ile Val Ala Ala Asp
                325                 330                 335

Val Tyr Ala Leu Gln Ser Ala Leu Pro Pro Arg Phe Gln Ala Ser Ala
            340                 345                 350

```
Ala Phe Ala Ala Asn Leu Ser Thr Ile Asn Thr Leu Arg Gln Ala Glu
        355                 360                 365

Thr Ser Asn Gly Ala Leu Lys Phe Pro Ser Leu His Asp Ser Pro Pro
    370                 375                 380

Met Leu Ala Gly Lys Ser Val Leu Glu Val Ser His Met Asp Thr Val
385                 390                 395                 400

Asp Ser Ala Val Thr Ala Thr Asn His Pro Leu Val Leu Gly Asp Trp
                405                 410                 415

Lys Gln Phe Leu Ile Gly Asp Arg Val Gly Ser Met Val Glu Leu Val
            420                 425                 430

Pro His Leu Phe Gly Pro Asn Arg Arg Pro Thr Gly Gln Arg Gly Phe
        435                 440                 445

Phe Ala Trp Phe Arg Val Gly Ser Asp Val Leu Val Arg Asn Ala Phe
    450                 455                 460

Arg Val Leu Lys Val Glu Thr Thr Ala
465                 470

<210> SEQ ID NO 9
<211> LENGTH: 10
<212> TYPE: PRT
<213> ORGANISM: Mycobacterium tuberculosis

<400> SEQUENCE: 9

Asp Pro Ala Pro Ala Pro Pro Val Pro Thr
1               5                   10

<210> SEQ ID NO 10
<211> LENGTH: 10
<212> TYPE: PRT
<213> ORGANISM: Mycobacterium tuberculosis

<400> SEQUENCE: 10

Cys Gly Ser Lys Pro Pro Ser Pro Glu Thr
1               5                   10

<210> SEQ ID NO 11
<211> LENGTH: 7
<212> TYPE: PRT
<213> ORGANISM: Mycobacterium tuberculosis
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 11

Xaa Xaa Ala Val Xaa Val Thr
1               5

<210> SEQ ID NO 12
<211> LENGTH: 16
<212> TYPE: PRT
<213> ORGANISM: Mycobacterium tuberculosis

<400> SEQUENCE: 12

Phe Ser Arg Pro Gly Leu Pro Val Glu Tyr Leu Gln Val Pro Ser Pro
1               5                   10                  15

<210> SEQ ID NO 13
```

<211> LENGTH: 741
<212> TYPE: PRT
<213> ORGANISM: Mycobacterium tuberculosis

<400> SEQUENCE: 13

```
Met Thr Asp Arg Val Ser Val Gly Asn Leu Arg Ile Ala Arg Val Leu
1               5                   10                  15

Tyr Asp Phe Val Asn Asn Glu Ala Leu Pro Gly Thr Asp Ile Asp Pro
            20                  25                  30

Asp Ser Phe Trp Ala Gly Val Asp Lys Val Val Ala Asp Leu Thr Pro
        35                  40                  45

Gln Asn Gln Ala Leu Leu Asn Ala Arg Asp Glu Leu Gln Ala Gln Ile
    50                  55                  60

Asp Lys Trp His Arg Arg Val Ile Glu Pro Ile Asp Met Asp Ala
65                  70                  75                  80

Tyr Arg Gln Phe Leu Thr Glu Ile Gly Tyr Leu Leu Pro Glu Pro Asp
                85                  90                  95

Asp Phe Thr Ile Thr Thr Ser Gly Val Asp Ala Glu Ile Thr Thr Thr
            100                 105                 110

Ala Gly Pro Gln Leu Val Val Pro Val Leu Asn Ala Arg Phe Ala Leu
        115                 120                 125

Asn Ala Ala Asn Ala Arg Trp Gly Ser Leu Tyr Asp Ala Leu Tyr Gly
    130                 135                 140

Thr Asp Val Ile Pro Glu Thr Asp Gly Ala Glu Lys Gly Pro Thr Tyr
145                 150                 155                 160

Asn Lys Val Arg Gly Asp Lys Val Ile Ala Tyr Ala Arg Lys Phe Leu
                165                 170                 175

Asp Asp Ser Val Pro Leu Ser Ser Gly Ser Phe Gly Asp Ala Thr Gly
            180                 185                 190

Phe Thr Val Gln Asp Gly Gln Leu Val Val Ala Leu Pro Asp Lys Ser
        195                 200                 205

Thr Gly Leu Ala Asn Pro Gly Gln Phe Ala Gly Tyr Thr Gly Ala Ala
    210                 215                 220

Glu Ser Pro Thr Ser Val Leu Leu Ile Asn His Gly Leu His Ile Glu
225                 230                 235                 240

Ile Leu Ile Asp Pro Glu Ser Gln Val Gly Thr Thr Asp Arg Ala Gly
                245                 250                 255

Val Lys Asp Val Ile Leu Glu Ser Ala Ile Thr Thr Ile Met Asp Phe
            260                 265                 270

Glu Asp Ser Val Ala Ala Val Asp Ala Ala Asp Lys Val Leu Gly Tyr
        275                 280                 285

Arg Asn Trp Leu Gly Leu Asn Lys Gly Asp Leu Ala Ala Ala Val Asp
    290                 295                 300

Lys Asp Gly Thr Ala Phe Leu Arg Val Leu Asn Arg Asp Arg Asn Tyr
305                 310                 315                 320

Thr Ala Pro Gly Gly Gly Gln Phe Thr Leu Pro Gly Arg Ser Leu Met
                325                 330                 335

Phe Val Arg Asn Val Gly His Leu Met Thr Asn Asp Ala Ile Val Asp
            340                 345                 350

Thr Asp Gly Ser Glu Val Phe Glu Gly Ile Met Asp Ala Leu Phe Thr
        355                 360                 365

Gly Leu Ile Ala Ile His Gly Leu Lys Ala Ser Asp Val Asn Gly Pro
    370                 375                 380

Leu Ile Asn Ser Arg Thr Gly Ser Ile Tyr Ile Val Lys Pro Lys Met
```

```
                385                 390                 395                 400
His Gly Pro Ala Glu Val Ala Phe Thr Cys Glu Leu Phe Ser Arg Val
                405                 410                 415

Glu Asp Val Leu Gly Leu Pro Gln Asn Thr Met Lys Ile Gly Ile Met
                420                 425                 430

Asp Glu Glu Arg Arg Thr Thr Val Asn Leu Lys Ala Cys Ile Lys Ala
                435                 440                 445

Ala Ala Asp Arg Val Val Phe Ile Asn Thr Gly Phe Leu Asp Arg Thr
            450                 455                 460

Gly Asp Glu Ile His Thr Ser Met Glu Ala Gly Pro Met Val Arg Lys
465                 470                 475                 480

Gly Thr Met Lys Ser Gln Pro Trp Ile Leu Ala Tyr Glu Asp His Asn
                485                 490                 495

Val Asp Ala Gly Leu Ala Ala Gly Phe Ser Gly Arg Ala Gln Val Gly
                500                 505                 510

Lys Gly Met Trp Thr Met Thr Glu Leu Met Ala Asp Met Val Glu Thr
                515                 520                 525

Lys Ile Ala Gln Pro Arg Ala Gly Ala Ser Thr Ala Trp Val Pro Ser
            530                 535                 540

Pro Thr Ala Ala Thr Leu His Ala Leu His Tyr His Gln Val Asp Val
545                 550                 555                 560

Ala Ala Val Gln Gln Gly Leu Ala Gly Lys Arg Arg Ala Thr Ile Glu
                565                 570                 575

Gln Leu Leu Thr Ile Pro Leu Ala Lys Glu Leu Ala Trp Ala Pro Asp
                580                 585                 590

Glu Ile Arg Glu Glu Val Asp Asn Asn Cys Gln Ser Ile Leu Gly Tyr
                595                 600                 605

Val Val Arg Trp Val Asp Gln Gly Val Gly Cys Ser Lys Val Pro Asp
                610                 615                 620

Ile His Asp Val Ala Leu Met Glu Asp Arg Ala Thr Leu Arg Ile Ser
625                 630                 635                 640

Ser Gln Leu Leu Ala Asn Trp Leu Arg His Gly Val Ile Thr Ser Ala
                645                 650                 655

Asp Val Arg Ala Ser Leu Glu Arg Met Ala Pro Leu Val Asp Arg Gln
                660                 665                 670

Asn Ala Gly Asp Val Ala Tyr Arg Pro Met Ala Pro Asn Phe Asp Asp
                675                 680                 685

Ser Ile Ala Phe Leu Ala Ala Gln Glu Leu Ile Leu Ser Gly Ala Gln
                690                 695                 700

Gln Pro Asn Gly Tyr Thr Glu Pro Ile Leu His Arg Arg Arg Arg Glu
705                 710                 715                 720

Phe Lys Ala Arg Ala Ala Glu Lys Pro Ala Pro Ser Asp Arg Ala Gly
                725                 730                 735

Asp Asp Ala Ala Arg
                740

<210> SEQ ID NO 14
<211> LENGTH: 252
<212> TYPE: PRT
<213> ORGANISM: Mycobacterium tuberculosis

<400> SEQUENCE: 14

Ala Pro Tyr Glu Asn Leu Met Val Pro Ser Pro Ser Met Gly Arg Asp
1               5                   10                  15
```

```
Ile Pro Val Ala Phe Leu Ala Gly Gly Pro His Ala Val Tyr Leu Leu
        20                  25                  30

Asp Ala Phe Asn Ala Gly Pro Asp Val Ser Asn Trp Val Thr Ala Gly
        35                  40                  45

Asn Ala Asn Thr Leu Ala Gly Lys Gly Ile Ser Val Val Ala Pro Ala
        50                  55                  60

Gly Gly Ala Tyr Ser Met Tyr Thr Asn Trp Glu Gln Asp Gly Ser Lys
65                  70                  75                  80

Gln Trp Asp Thr Phe Leu Ser Ala Glu Leu Pro Asp Trp Leu Ala Ala
                85                  90                  95

Asn Arg Gly Ala Ala Gln Gly Gly Tyr Gly Ala Met Ala Ala Ala Phe
                100                 105                 110

His Pro Asp Arg Phe Gly Phe Ala Gly Ser Met Ser Gly Phe Leu Tyr
                115                 120                 125

Pro Ser Asn Thr Thr Asn Gly Ala Ile Ala Ala Gly Met Gln Gln
130                 135                 140

Phe Gly Gly Val Asp Thr Asn Gly Met Trp Gly Ala Pro Gln Leu Gly
145                 150                 155                 160

Arg Trp Lys Trp His Asp Pro Trp His Ala Ser Leu Leu Ala Gln Asn
                165                 170                 175

Asn Thr Arg Val Trp Val Trp Ser Pro Thr Asn Pro Gly Ala Ser Asp
                180                 185                 190

Pro Ala Ala Met Ile Gly Gln Thr Ala Glu Ala Met Gly Asn Ser Arg
                195                 200                 205

Met Phe Tyr Asn Gln Tyr Arg Ser Val Gly Gly His Asn Gly His Phe
                210                 215                 220

Asp Phe Pro Ser Gly Asp Asn Gly Trp Gly Ser Trp Ala Pro Gln Leu
225                 230                 235                 240

Gly Ala Met Ser Gly Asp Ile Val Gly Ala Ile Arg
                245                 250

<210> SEQ ID NO 15
<211> LENGTH: 15
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa can be Met or Leu
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid

<400> SEQUENCE: 15

Xaa Pro Val Xaa Val Xaa Pro Gly Xaa Glu Xaa Xaa Gln Asp Asn
1               5                   10                  15

<210> SEQ ID NO 16
<211> LENGTH: 15
```

```
<212> TYPE: PRT
<213> ORGANISM: Mycobacterium tuberculosis

<400> SEQUENCE: 16

Asp Pro Val Leu Val Phe Pro Gly Met Glu Ile Arg Gln Asp Asn
1               5                   10                  15
```

The invention claimed is:

1. A method for the early detection of active *Mycobacterium tuberculosis* (Mtb) disease or infection in a subject, comprising assaying a biological fluid sample from an asymptomatic subject or a subject having constitutional symptoms of tuberculosis, but before the onset of specific symptoms identifiable as advanced tuberculosis, for the presence of early antibodies specific for one or more early Mtb antigens which antigens are characterized as being surface or secreted proteins that are
   (i) bound by antibodies found in tuberculosis patients who are in a stage of disease prior to the onset of (a) smear-positivity of sputum or other pulmonary associated fluid for acid-fast bacilli and (b) cavitary pulmonary lesions, and
   (ii) non-reactive with sera from healthy control subjects or healthy subjects with latent inactive tuberculosis
   and which antibodies are specific for an antigen selected from the group consisting of
   (a) PirG protein encoded by the Mtb gene Rv3810;
   (b) PE-PGRS protein encoded by the Mtb gene Rv3367;
   (c) PTRP protein encoded by the Mtb gene Rv0538;
   (d) MtrA protein encoded by the Mtb gene Rv3246c; and
   (e) an epitope of any one of (a)-(d),
   wherein the presence of said early antibodies specific for said early antigens is indicative of the presence of said disease or infection.

2. A method for the early detection of active Mtb disease or infection in a subject, comprising assaying a biological fluid sample from an asymptomatic subject or a subject having constitutional symptoms of tuberculosis, but before the onset of specific symptoms identifiable as advanced tuberculosis, for the presence of T lymphocytes reactive with an early Mtb antigen selected from the group consisting of
   (a) PirG protein encoded by the Mtb gene Rv3810;
   (b) PE-PGRS protein encoded by the Mtb gene Rv3367;
   (c) PTRP protein encoded by the Mtb gene Rv0538;
   (d) MtrA protein encoded by the Mtb gene Rv3246c; and
   (e) a T cell epitope of any one of (a)-(d).

3. A method for the early detection of active Mtb disease or infection in a subject, comprising assaying a biological fluid or cell or tissue sample from an asymptomatic subject or a subject having constitutional symptoms of tuberculosis, but before the onset of specific symptoms identifiable as advanced tuberculosis, for the presence of one or more early *M. tuberculosis* early antigens selected from the group consisting of
   (a) PirG protein encoded by the Mtb gene Rv3810;
   (b) PE-PGRS protein encoded by the Mtb gene Rv3367;
   (c) PTRP protein encoded by the Mtb gene Rv0538;
   (d) MtrA protein encoded by the Mtb gene Rv3246c; and
   (e) an epitope of any one of (a)-(d),
   using an antiserum or a monoclonal antibody specific for an epitope of said an antigen, wherein the presence of said one or more antigens in said fluid, cell or tissue sample is indicative of the presence of said disease or infection in the subject.

4. A method for the early detection of active Mtb disease or infection in a subject, comprising assaying a biological fluid sample from an asymptomatic subject or a subject having constitutional symptoms of tuberculosis, but before the onset of specific symptoms identifiable as advanced tuberculosis, for the presence of immune complexes consisting of one or more early *M. tuberculosis* antigens complexed with an antibody specific for said antigen, which antigen is selected from the group consisting of
   (a) PirG protein encoded by the Mtb gene Rv3810;
   (b) PE-PGRS protein encoded by the Mtb gene Rv3367;
   (c) PTRP protein encoded by the Mtb gene Rv0538; and
   (d) MtrA protein encoded by the Mtb gene Rv3246c,
   (e) an epitope of any one of (a)-(d),
   wherein the presence of said immune complexes in said sample is indicative of the presence of said disease or infection in the subject.

5. The method of any one of claims 1-4 that further includes performance of a test that detects Mtb bacilli in a sample of sputum or other body fluid of said subject.

6. The method of any of claims 1-4 wherein said biological fluid sample is serum, urine or saliva.

7. The method of any of claims 1-4 comprising, prior to said assaying step, the step of removing from said sample antibodies specific for cross-reactive epitopes or antigens of proteins present in *M. tuberculosis* and in other bacterial genera.

8. The method of claim 7 wherein said removing is performed by immunoadsorption of said sample with *E. coli* antigens.

9. The method of any of claims 1-4, wherein said subject is a human.

10. The method of claim 9 wherein said subject is infected with HIV-1 or is at high risk for tuberculosis.

11. The method of any of claims 1-4 which includes assaying said sample for antibodies specific for one or more additional early antigens of *M. tuberculosis* selected from the group consisting of:
    (a) an 88 kDa *M. tuberculosis* protein having the an amino acid sequence SEQ ID NO:13:

```
MTDRVSVGNL  RIARVLYDFV  NNEALPGTDI  DPDSFWAGVD  KVVADLTPQN  QALLNARDEL

QAQIDKWHRR  RVIEPIDMDA  YRQFLTEIGY  LLPEPDDFTI  TTSGVDAEIT  TTAGPQLVVP

VLNARFALNA  ANARWGSLYD  ALYGTDVIPE  TDGAEKGPTV  NKVRGDKVIA  YARKFLDDSV
```

```
PLSSGSFGDA  TGFTVQDGQL  VVALPDKSTG  LANPGQFAGY  TGAAESPTSV  LLINHGLHIE

ILIDPESQVG  TTDRAGVKDV  ILESAITTIM  DFEDSVAAVD  AADKVLGYRN  WLGLNKGDLA

AAVDKDGTAF  LRVLNRDRNY  TAPGGGQFTL  PGRSLMFVRN  VGHLMTNDAI  VDTDGSEVFE

GIMDALFTGL  IAIHGLKASD  VNGPLINSRT  GSIYIVKPKM  HGPAEVAFTC  ELFSRVEDVL

GLPQNTMKIG  IMDEERRTTV  NLKACIKAAA  DRVVFINTGF  LDRTGDEIHT  SMEAGPMVRK

GTMKSQPWIL  AYEDHNVDAG  LAAGFSGRAQ  VGKGMWTMTE  LMADMVETKI  AQPRAGASTA

WVPSPTAATL  HALHYHQVDV  AAVQQGLAGK  RRATIEQLLT  IPLAKELAWA  PDEIREEVDN

NCQSILGYVV  RWVDQGVGCS  KVPDIHDVAL  MEDRATLRIS  SQLLANWLRH  GVITSADVRA

SLERMAPLVD  RQNAGDVAYR  PMAPNFDDSI  AFLAAQELIL  SGAQQPNGYT  EPILHRRRRE

FKARAAEKPA  PSDRAGDDAA  R
```

(b) a 27 kDa *M. tuberculosis* protein named MPT51 having the amino acid sequence SEQ ID NO:14:

```
APYENLMVPS  PSMGRDIPVA  FLAGGPHAVY  LLDAFNAGPD  VSNWVTAGNA  NTLAGKGIS

VVAPAGGAYS  MYTNWEQDGS  KQWDTFLSAE  LPDWLAANRG  AAQGGYGAMA  AAFHPDRFG

FAGSMSGFLY  PSNTTTNGAI  AAGMQQFGGV  DTNGMWGAPQ  LGRWKWHDPW  HASLLAQNN

TRVWVWSPTN  PGASDPAAMI  GQTAEAMGNS  RMFYNQYRSV  GGHNGHFDFP  SGDNGWGSW

APQLGAMSGD  IVGAIR
```

(c) a protein characterized as *M. tuberculosis* antigen 85C; or (d) a glycoprotein characterized as *M. tuberculosis* antigen MPT32.

12. A kit useful for early detection of *M. tuberculosis* disease comprising:
(a) an antigenic composition comprising one or more proteins selected from the group consisting of
   (i) PirG protein encoded by the Mtb gene Rv3810;
   (ii) PE-PGRS protein encoded by the Mtb gene Rv3367;
   (iii) PTRP protein encoded by the Mtb gene Rv0538; and
   (iv) MtrA protein encoded by the Mtb gene Rv3246c,
   or an epitope of any of (i)-(iv), in combination with
(b) reagents for detection of antibodies which bind to said *M. tuberculosis* protein or proteins.

13. The kit according of claim 12 wherein at least one of said *M. tuberculosis* proteins is recombinant.

14. An antigenic composition useful for early detection of *M. tuberculosis* disease or infection comprising one or a mixture of two or more early *M. tuberculosis* antigens which antigens are selected from the group consisting of
(a) PirG protein encoded by the Mtb gene Rv3810;
(b) PE-PGRS protein encoded by the Mtb gene Rv3367;
(c) PTRP protein encoded by the Mtb gene Rv0538;
(d) MtrA protein encoded by the Mtb gene Rv3246c; and
(e) an epitope of any of (a)-(d),
said composition being substantially free of other *M. tuberculosis* proteins with which said *M. tuberculosis* proteins are natively admixed in a culture of *M. tuberculosis*.

15. The composition of claim 14, further comprising one or more of:
(a) an 88 kDa *M. tuberculosis* protein having the an amino acid sequence SEQ ID NO:13:

```
MTDRVSVGNL  RIARVLYDFV  NNEALPGTDI  DPDSFWAGVD  KVVADLTPQN  QALLNARDEL

QAQIDKWHRR  RVIEPIDMDA  YRQFLTEIGY  LLPEPDDFTI  TTSGVDAEIT  TTAGPQLVVP

VLNARFALNA  ANARWGSLYD  ALYGTDVIPE  TDGAEKGPTY  NKVRGDKVIA  YARKFLDDSV

PLSSGSFGDA  TGFTVQDGQL  VVALPDKSTG  LANPGQFAGY  TGAAESPTSV  LLINHGLHIE

ILIDPESQVG  TTDRAGVKDV  ILESAITTIM  DFEDSVAAVD  AADKVLGYRN  WLGLNKGDLA

AAVDKDGTAF  LRVLNRDRNY  TAPGGGQFTL  PGRSLMFVRN  VGHLMTNDAI  VDTDGSEVFE

GIMDALFTGL  IAIHGLKASD  VNGPLINSRT  GSIYIVKPKM  HGPAEVAFTC  ELFSRVEDVL

GLPQNTMKIG  IMDEERRTTV  NLKACIKAAA  DRVVFINTGF  LDRTGDEIHT  SMEAGPMVRK
```

-continued

```
GTMKSQPWIL AYEDHNVDAG LAAGFSGRAQ VGKGMWTMTE LMADMVETKI AQPRAGASTA

WVPSPTAATL HALHVHQVDV AAVQQGLAGK RRATIEQLLT IPLAKELAWA PDEIREEVDN

NCQSILGYVV RWVDQGVGCS KVPDIHDVAL MEDRATLRIS SQLLANWLRH GVITSADVRA

SLERMAPLVD RQNAGDVAYR PMAPNFDDSI AFLAAQELIL SGAQQPNGYT EPILHRRRRE

FKARAAEKPA PSDRAGDDAA R;
```

(b) a 27 kDa *M. tuberculosis* protein named MPT51 having the amino acid sequence SEQ ID NO:14

```
APYENLMVPS PSMGRDIPVA FLAGGPHAVY LLDAFNAGPD VSNWVTAGNA

NTLAGKGIS VVAPAGGAYS MYTNWEQDGS KQWDTFLSAE LPDWLAANRG

AAQGGYGAMA AAFHPDRFG FAGSMSGFLY PSNTTTNGAI AAGMQQFGGV

DTNGMWGAPQ LGRWKWHDPW HASLLAQNN TRVWVWSPTN PGASDPAAMI

GQTAEAMGNS RMFYNQYRSV GGHNGHFDFP SGDNGWGSW APQLGAMSGD

IVGAIR
```

(c) a protein characterized as *M. tuberculosis* antigen 85C; or (d) a glycoprotein characterized as *M. tuberculosis* antigen MPT32.

16. The antigenic composition of claim 15, further comprising one or more of:

(a) an 88 kDa *M. tuberculosis* protein having the an amino acid sequence SEQ ID NO:13:

```
MTDRVSVGNL RIARVLYDFV NNEALPGTDI DPDSFWAGVD KVVADLTPQN QALLNARDEL

QAQIDKWHRR RVIEPIDMDA YRQFLTEIGY LLPEPDDFTI TTSGVDAEIT TTAGPQLVVP

VLNARFALNA ANARWGSLYD ALYGTDVIPE TDGAEKGPTY NKVRGDKVIA YARKFLDDSV

PLSSGSFGDA TGFTVQDGQL VVALPDKSTG LANPGQFAGY TGAAESPTSV LLINHGLHIE

ILIDPESQVG TTDRAGVKDV ILESAITTIM DFEDSVAAVD AADKVLGYRN WLGLNKGDLA

AAVDKDGTAF LRVLNRDRNY TAPGGGQFTL PGRSLMFVRN VGHLMTNDAI VDTDGSEVFE

GIMDALFTGL IAIHGLKASD VNGPLINSRT GSIYIVKPKM HGPAEVAFTC ELFSRVEDVL

GLPQNTMKIG IMDEERRTTV NLKACIKAAA DRVVFINTGF LDRTGDEIHT SMEAGPMVRK

GTMKSQPWIL AYEDHNVDAG LAAGFSGRAQ VGKGMWTMTE LMADMVETKI AQPRAGASTA

WVPSPTAATL HALHYHQVDV AAVQQGLAGK RRATIEQLLT IPLAKELAWA PDEIREEVDN

NCQSILGYVV RWVDQGVGCS KVPDIHDVAL MEDRATLRIS SQLLANWLRH GVITSADVRA

SLERMAPLVD RQNAGDVAYR PMAPNFDDSI AFLAAQELIL SGAQQPNGYT EPILHRRRRE

FKARAAEKPA PSDRAGDDAA R;
```

(b) a 27 kDa *M. tuberculosis* protein named MPT51 having the amino acid sequence SEQ ID NO:14:

```
APYENLMVPS PSMGRDIPVA FLAGGPHAVY LLDAFNAGPD VSNWVTAGNA

NTLAGKGIS VVAPAGGAYS MYTNWEQDGS KQWDTFLSAE LPDWLAANRG

AAQGGYGAMA AAFHPDRFG FAGSMSGFLY PSNTTTNGAI AAGMQQFGGV

DTNGMWGAPQ LGRWKWHDPW HASLLAQNN TRVWVWSPTN PGASDPAAMI

GQTAEAMGNS RMFYNQYRSV GGHNGHFDFP SGDNGWGSW APQLGAMSGD

IVGAIR;
```

(c) a protein characterized as *M. tuberculosis* antigen 85C; or
(d) a glycoprotein characterized as *M. tuberculosis* antigen MPT32.

17. The antigenic composition of any of claim 15 or 16 further comprising one or more of the following *M. tuberculosis* antigenic proteins having an approximate molecular weight as indicated:
   (i) a 28 kDa protein corresponding to the spot identified as Ref. No. 77 in Table 2;
   (ii) a 29/30 kDa protein corresponding to the spot identified as Ref. No. 69 or 59 in Table 2;
   (iii) a 31 kDa protein corresponding to the spot identified as Ref. No. 103 in Table 2;
   (iv) a 35 kDa protein corresponding to the spot identified as Ref. No. 66 in Table 2 and reacting with monoclonal antibody IT-23;
   (v) a 42 kDa protein corresponding to the spot identified as Ref. No. 68 or 80 in Table 2;
   (vi) a 48 kDa protein corresponding to the spot identified as Ref. No. 24 in Table 2; and
   (vii) a 104 kDa protein corresponding to the spot identified as Ref. No. 111 in Table 2, which spots are obtained by 2-dimensional electrophoretic separation of *M. tuberculosis* lipoarabinomannan-free culture filtrate proteins as follows:
   (A) incubating 3 hours at 20° C. in 9M urea, 2% Nonidet P-40, 5% β-mercaptoethanol, and 5% ampholytes at pH 3-10;
   (B) isoelectric focusing on 6% polyacrylamide isoelectric focusing tube gel of 1.5 mm×6.5 cm, said gel containing 5% ampholytes in a 1:4 ratio of pH 3-10 ampholytes to pH 4-6.5 ampholytes for 3 hours at 1 kV using 10mM $H_3PO_4$ as catholyte and 20 mM NaOH as anolyte, to obtain a focused gel;
   (C) subjecting the focused gel to SDS PAGE in the second dimension by placement on a preparative SDS-polyacrylamide gel of 7.5×10 cm×1.5 mm containing a 6% stack over a 15% resolving gel and electrophoresing at 20 mA per gel for 0.3 hours followed by 30 mA per gel for 1.8 hours.

* * * * *